United States Patent
Wang et al.

(10) Patent No.: US 9,603,850 B2
(45) Date of Patent: Mar. 28, 2017

(54) MERTK-SPECIFIC PYRAZOLOPYRIMIDINE COMPOUNDS

(71) Applicant: The University of North Carolina at Chapel Hill, Chapel Hill, NC (US)

(72) Inventors: Xiaodong Wang, Chapel Hill, NC (US); Stephen Frye, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/678,678

(22) Filed: Apr. 3, 2015

(65) Prior Publication Data

US 2015/0291605 A1    Oct. 15, 2015

Related U.S. Application Data

(60) Provisional application No. 61/978,268, filed on Apr. 11, 2014, provisional application No. 61/978,281, filed on Apr. 11, 2014, provisional application No. 61/978,290, filed on Apr. 11, 2014, provisional application No. 61/978,443, filed on Apr. 11, 2014, provisional application No. 61/978,485, filed on Apr. 11, 2014, provisional application No. 61/978,513, filed on Apr. 11, 2014, provisional application No. 61/978,321, filed on Apr. 11, 2014, provisional application No. 61/994,384, filed on May 16, 2014, provisional application No. 62/088,159, filed on Dec. 5, 2014.

(51) Int. Cl.

| | |
|---|---|
| *A01N 43/90* | (2006.01) |
| *A61K 31/519* | (2006.01) |
| *C07D 487/00* | (2006.01) |
| *A61K 31/506* | (2006.01) |
| *A61K 31/5377* | (2006.01) |
| *A61K 31/505* | (2006.01) |
| *A61K 31/551* | (2006.01) |
| *A61K 31/55* | (2006.01) |
| *A61K 31/5513* | (2006.01) |
| *A61K 45/06* | (2006.01) |
| *C07D 487/04* | (2006.01) |
| *C07D 401/04* | (2006.01) |
| *C07D 401/14* | (2006.01) |
| *C07D 487/08* | (2006.01) |

(52) U.S. Cl.
CPC .......... *A61K 31/506* (2013.01); *A61K 31/505* (2013.01); *A61K 31/519* (2013.01); *A61K 31/5377* (2013.01); *A61K 31/55* (2013.01); *A61K 31/551* (2013.01); *A61K 31/5513* (2013.01); *A61K 45/06* (2013.01); *C07D 401/04* (2013.01); *C07D 401/14* (2013.01); *C07D 487/04* (2013.01); *C07D 487/08* (2013.01)

(58) Field of Classification Search
None
See application file for complete search history.

(56) References Cited

U.S. PATENT DOCUMENTS

| | | |
|---|---|---|
| 5,958,930 A | 9/1999 | Gangjee |
| 7,217,710 B2 | 5/2007 | Adams et al. |
| 7,589,086 B2 | 9/2009 | Bondavalli et al. |
| 7,897,607 B2 | 3/2011 | Gyorkos et al. |
| 7,956,060 B2 | 6/2011 | Arai et al. |
| 7,998,978 B2 | 8/2011 | Huang et al. |
| 8,324,225 B2 | 12/2012 | Brain et al. |
| 8,362,023 B2 | 1/2013 | Liu et al. |
| 8,415,361 B2 | 4/2013 | Lemke et al. |
| 8,513,242 B2 | 8/2013 | Chiang et al. |
| 2004/0209895 A1 | 10/2004 | Luecking et al. |
| 2006/0025383 A1 | 2/2006 | Wishart et al. |
| 2007/0078140 A1 | 4/2007 | Borzilleri et al. |
| 2007/0105874 A1 | 5/2007 | Zhang et al. |
| 2007/0225306 A1 | 9/2007 | Choi et al. |
| 2007/0275984 A1 | 11/2007 | Imogai et al. |
| 2008/0248046 A1 | 10/2008 | Ni et al. |
| 2008/0267887 A1 | 10/2008 | Yuan et al. |
| 2009/0012060 A1 | 1/2009 | Arai et al. |
| 2010/0137313 A1 | 6/2010 | Boriack-Sjodin et al. |
| 2010/0247554 A1 | 9/2010 | Lemke et al. |
| 2010/0266604 A1 | 10/2010 | Rothlin et al. |
| 2011/0281867 A1 | 11/2011 | Kalman et al. |
| 2011/0319267 A1 | 12/2011 | Ekwuribe et al. |

(Continued)

FOREIGN PATENT DOCUMENTS

| | | |
|---|---|---|
| CA | 2492319 | 4/2004 |
| EP | 1710246 A1 | 10/2006 |

(Continued)

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
U.S. Appl. No. 13/641,729, filed Nov. 9, 2012, The University of North Carolina at Chapel Hill.
U.S. Appl. No. 14/348,805, filed Mar. 31, 2014, The University of North Carolina at Chapel Hill.
U.S. Appl. No. 14/384,789, filed Sep. 12, 2014, The University of North Carolina at Chapel Hill.
U.S. Appl. No. 14/436,356, filed Apr. 16, 2015, The University of North Carolina at Chapel Hill.
U.S. Appl. No. 14/647,733, filed May 27, 2015, The University of North Carolina at Chapel Hill.
U.S. Appl. No. 14/678,905, filed Apr. 3, 2015, The University of North Carolina at Chapel Hill.
U.S. Appl. No. 14/678,830, filed Apr. 3, 2015, The University of North Carolina at Chapel Hill.
U.S. Appl. No. 14/678,879, filed Apr. 3, 2015, The University of North Carolina at Chapel Hill.
U.S. Appl. No. 14/678,898, filed Apr. 3, 2015, The University of North Carolina at Chapel Hill.

(Continued)

*Primary Examiner* — Jeffrey H Murray
(74) *Attorney, Agent, or Firm* — Alston & Bird LLP

(57) ABSTRACT

The present invention includes pyrazolopyrimidine compounds of Formula I that selectively inhibit Mer tyrosine kinase (MerTK) activity and/or Tyro3 tyrosine kinase activity, and use of these pyrazolopyrimidine compounds as anti-cancer agents, immunostimulatory and immunomodulatory agents, anti-platelet agents, anti-infective agents, and as adjunctive agents in combination with chemotherapeutic, radiation or other standard of care for neoplasms.

8 Claims, No Drawings

(56) References Cited

U.S. PATENT DOCUMENTS

| | | |
|---|---|---|
| 2012/0035194 A1 | 2/2012 | Huang et al. |
| 2012/0207763 A1 | 8/2012 | Brain et al. |
| 2012/0207764 A1 | 8/2012 | Terrett et al. |
| 2012/0219559 A1 | 8/2012 | Chen et al. |
| 2012/0230991 A1 | 9/2012 | Graham et al. |
| 2013/0029993 A1 | 1/2013 | Stadtmueller |
| 2013/0034862 A1 | 2/2013 | Fantl |
| 2013/0059836 A1 | 3/2013 | Wang et al. |
| 2013/0072382 A1 | 3/2013 | Trullinger et al. |
| 2013/0102587 A1 | 4/2013 | Evans et al. |
| 2013/0137708 A1 | 5/2013 | Garske et al. |
| 2013/0150368 A1 | 6/2013 | Ashcraft et al. |
| 2013/0266563 A1 | 10/2013 | Gokaraju et al. |

FOREIGN PATENT DOCUMENTS

| | | |
|---|---|---|
| EP | 1803723 A1 | 7/2007 |
| EP | 2133095 A1 | 12/2009 |
| EP | 2489663 A1 | 8/2012 |
| EP | 2840080 A1 | 2/2015 |
| WO | WO 97/49706 A1 | 12/1997 |
| WO | WO 03/029209 A2 | 4/2003 |
| WO | WO 2005/009443 A1 | 2/2005 |
| WO | WO 2005/028434 A2 | 3/2005 |
| WO | WO 2005/095382 A1 | 10/2005 |
| WO | WO 2006/035067 A2 | 4/2006 |
| WO | WO 2006/071819 A1 | 7/2006 |
| WO | WO 2007/032445 A1 | 3/2007 |
| WO | WO 2007/035963 A2 | 3/2007 |
| WO | WO 2007/041379 A1 | 4/2007 |
| WO | WO 2007/044426 A2 | 4/2007 |
| WO | WO 2007/075554 A2 | 7/2007 |
| WO | WO 2007/113254 A1 | 10/2007 |
| WO | WO 2007/134828 A1 | 11/2007 |
| WO | WO 2009/032694 A1 | 3/2009 |
| WO | WO 2009/047359 A1 | 4/2009 |
| WO | WO 2010/043865 A1 | 4/2010 |
| WO | WO 2010/085597 A1 | 7/2010 |
| WO | WO 2010/117425 A1 | 10/2010 |
| WO | WO 2010/129802 A1 | 11/2010 |
| WO | WO 2011/029915 A1 | 3/2011 |
| WO | WO 2011/065800 A2 | 6/2011 |
| WO | WO 2011/090760 A1 | 7/2011 |
| WO | WO 2011/103441 A1 | 8/2011 |
| WO | WO 2011/146313 A1 | 11/2011 |
| WO | WO 2012/053606 A1 | 4/2012 |
| WO | WO 2012/158795 A1 | 11/2012 |
| WO | WO 2013/032591 A1 | 3/2013 |
| WO | WO 2013/042006 A1 | 3/2013 |
| WO | WO 2013/052417 A1 | 4/2013 |
| WO | WO 2013/124324 A1 | 8/2013 |
| WO | WO 2013/157022 A1 | 10/2013 |
| WO | WO 2013/177168 A1 | 11/2013 |
| WO | WO 2014/062774 A1 | 4/2014 |
| WO | WO 2014/085225 A1 | 6/2014 |

OTHER PUBLICATIONS

U.S. Appl. No. 14/678,540, filed Apr. 3, 2015, The University of North Carolina at Chapel Hill.
PCT/US2011/036215, The University of North Carolina at Chapel Hill, May 12, 2011.
PCT/US2013/042033, The University of North Carolina at Chapel Hill, May 21, 2013.
PCT/US2013/065192, The University of North Carolina at Chapel Hill, Oct. 16, 2013.
PCT/US2013/071409, The University of North Carolina at Chapel Hill, Nov. 22, 2013.
PCT/US2015/024381, The University of North Carolina at Chapel Hill, Apr. 3, 2015.
PCT/US2015/024393, The University of North Carolina at Chapel Hill, Apr. 4, 2015.
PCT/US2015/024395, The University of North Carolina at Chapel Hill, Apr. 3, 2015.
PCT/US2015/024395, The University of North Carolina at Chapel Hill, Apr. 4, 2015.
PCT/US2015/024328, The University of North Carolina at Chapel Hill, Apr. 3, 2015.
PCT/US2015/024258, The University of North Carolina at Chapel Hill, Apr. 3, 2015.
PCT/US2015/024396, The University of North Carolina at Chapel Hill, Apr. 4, 2015.
PCT/US2015/024380, The University of North Carolina at Chapel Hill, Apr. 3, 2015.
PCT/US2015/024301, The University of North Carolina at Chapel Hill, Apr. 3, 2015.
Aly et al. "Heteroannelations with o-amino aldehyde and o-amino cyano of some pyrazole derivatives" Afinidad, Barcelona, ES (2004) 61:510-515.
Angelillo-Scherrer et al. "Role of Gas6 receptors in platelet signaling during thrombus stabilization and implications for antithrombotic therapy", J. Clin. Invest. (2005) 115(2):237-246.
Bernsmeier, et al. "Patients with Acute-on-Chronic Liver Failure Have Increased Numbers of Regulatory Immune Cells Expressing the Receptor Tyrosine Kinase MERTK", Gastroenterology (2015), 1-13.
Bhattacharayya, et al. "Enveloped viruses disable innate immune responses in dendritic cells by direct activation of TAM receptors", Cell Host & Microbe (2013) 14:136-147.
Brindley, et al. "Tyrosine kinase receptor Axl enhances entry of Zaire ebolavirus without direct interactions with the viral glycoprotein", Virology (2011) 415:83-84.
Cavasotto et al. "In silico identification of novel EGFR inhibitors with antiproliferative activity against cancer cells" Bioorg. Med. Chem. Lett. (2006) 16:1969-1974.
Chen, et al. "Identification of Gas6 as a ligand for Mer, a neural cell adhesion molecule related receptor tyrosine kinase implicated in cellular transformation", Oncogene (1997) 14:2033-2039.
Chen, et al, "Mer Receptor tyrosine Kinase Signaling Participates in Platelet Function", Arterioscler. Thromv Vasc. Biol. (2004) 24:1118-1123.
Christoph, S. et al. "UNC569, a novel small-molecule Mer inhibitor with efficacy against acute lymphoblastic leukemia in vitro and in vivo", Mol Cancer Ther. (2013) 12(11):2367-77.
Cook, et al. "MerTK inhibition in tumor leukocytes decreases tumor growth and metastasis" J. Clin. Invest. (2013) 123:3231-3242.
Earp, S. "Chemical Biology Consortium: Mer Kinase Inhibitor Studies" Presentation at the Chemical Biology Consortium, Jan. 26, 2012.
Frye, S. "Academic Drug Discovery: US Perspective and Examples" Presentation at the NCI Translational Science Meeting, Washington DC, Jul. 29, 2011.
Frye, S. "Academic Drug Discovery and Chemical Biology", Presentation at the Northwestern 18th Annual Drug Discovery Symposium. Nov. 13, 2013.
Graham, et al. "Cloning and mRNA expression analysis of a novel human protooncogene, c-mer", Cell Growth Differ. (1994) 5:647-657.
Lee-Sherick, et al. "Efficacy of a Mer and Flt3 tyrosine kinase small molecule inhibitor, UNC1666, in acute myeloid leukemia", Oncotarget, Advance Publications, Feb. 10, 2015.
Linger et al. "Mer receptor tyrosine kinase is a therapeutic target in pre-B-cell acute lymphoblastic leukemia" Blood (2013) 122(9):1599-1609.
Liu, J. et al. "Discovery of Novel Small Molecule Mer Kinase Inhibitors for the Treatment of Pediatric Acute Lymphoblastic Leukemia" ACS Med. Chem. Lett. (2012) 3(2):129-134.
Liu, J, et al. "UNC1062, a new and potent Mer inhibitor", Eur J Med Chem. (2013) 65:83-93.
Meertens, L. et al. "The TIM and TAM families of phosphatidylserine receptors mediate dengue virus entry", Cell Host Microbe (2012) 12:544-557.
Mercer, J. & Helenius, A. "Vaccinia virus uses macropinocytosis and apoptotic mimicry to enter host cells", Science (2008) 320: 531-535.

(56) References Cited

OTHER PUBLICATIONS

Morizono, et al, "The Soluble Serum Protein Gas6 Bridges Virion Envelope Phosphatidylserine to the TAM Receptor Tyrosine Kinase Axl to mediate Viral Entry", *Cell Host & Microbe* (2011) 9:286-298.
Morizono and Chen, "Role of Phosphatidyl Receptors in Enveloped Virus Infection", *J. Virology* (2014) 88(8):4275-4290.
Paolino, M., et al. "The E3 ligase Cbl-b and TAM receptors regulate cancer metastasis via natural killer cells", *Nature* (2014) 507:508-512.
Powell et al. "Highly selective 2,4-diaminopyridine-5-carboxamide inhibitors of Sky kinase", *Bioorg. Med. Chem. Lett.* (2013) 23:1046-1050.
Powell et al. "Optimization of highly selective 2,4-diaminopyridine-5-carboxamide inhibitors of Sky kinase", *Bioorg. Med. Chem. Lett.* (2013) 23:1051-1055.
Sather, et al. "A soluble form of the Mer receptor tyrosine kinase inhibits macrophage clearance of apoptotic cells and platelet aggregation", *Blood* (2007) 109(3):1026-1033.
Schlegel et al. "MER receptor tyrosine kinase is a therapeutic target in melanoma" *J. Clin. Invest.* (2013) 123(5): 2257-67.
Shimojima, et al. "Tyro3 Family-mediated Cell Entry of Ebola and Marburg Viruses", *Journal of Virology* (2006) 80(20):10109-10116.
Zhang, W., et al. "Discovery of Mer specific tyrosine kinase inhibitors for the treatment and prevention of thrombosis", *J. Med. Chem.* (2013) 56:9693-9700.
Zhang, W., et al. "Pseudo-cyclization through intramolecular hydrogen bond enables discovery of pyridine substituted pyrimidines as new Mer kinase inhibitors", *J. Med. Chem.* (2013) 56:9683-9692.
Extended European Search Report, EP 11783985.2, mailed Oct. 15, 2013.
Extended European Search Report, EP 12839069.7, mailed May 4, 2015.
International Search Report and Written Opinion, PCT/US2011/036215, mailed Aug. 16, 2011.
International Preliminary Report on Patentability, PCT/US2011/036215, mailed Nov. 29, 2012.
International Search Report and Written Opinion, PCT/US2012/058298, mailed Dec. 7, 2012.
International Search Report and Written Opinion, PCT/US2013/042033, mailed Aug. 27, 2013.
International Preliminary Report on Patentability, PCT/US2013/042033, mailed Dec. 4, 2014.
International Search Report and Written Opinion, PCT/US2013/065192, mailed Jan. 24, 2014.
International Preliminary Report on Patentability, PCT/US2013/065192, Apr. 30, 2015.
International Search Report and Written Opinion, PCT/US2013/071409, mailed Mar. 31, 2014.
International Preliminary Report on Patentability, PCT/US2013/071409, mailed Jun. 11, 2015.
International Search Report and Written Opinion, PCT/US2015/24258, mailed Jun. 24, 2015.
International Search Report and Written Opinion, PCT/US2015/24301, mailed Jun. 25, 2015.
International Search Report and Written Opinion, PCT/US2015/24328, mailed Jun. 25, 2015.
International Search Report and Written Opinion, PCT/US2015/24362, mailed Jun. 26, 2015.
International Search Report and Written Opinion, PCT/US2015/24373, mailed Jul. 7, 2015.
International Search Report and Written Opinion, PCT/US2015/24380, mailed Jul. 1, 2015.
International Search Report and Written Opinion, PCT/US2015/24381, mailed Jul. 1, 2015.
Examination Report corresponding to European Application No. 13793925.2 dated Nov. 30, 2015.
Database Caplus [Online]—Chemical Abstracts Service, Columbus, Ohio, US; 2004, Ismail, M.A.: "Efficient synthesis of 5-(5-aryl-2-furyl)pyrimidine derivatives", Database accession No. 2004:551368; & Ismail, M.A.: "Efficient synthesis of 5-(5-aryl-2-furyl)pyrimidine derivatives", Mansoura Science Bulletin, A: Chemistry, vol. 30, No. 2, 2003, pp. 157-172 (Abstract Only).
Database Caplus in STN, Acc. No. 2007:1144983, Guillemont et al., WO 2007/113254 A 1 (Oct. 11, 2007) (abstract).
Ishida et al. "Novel and orally active 5-(1,3,4-oxadiazol-2-yl)pyrimidine derivatives as selective FLT3 inhibitors", *Bioorganic & Medicinal Chemistry Letters* 18:5472-5477 (2008).
Kiyoi et al. "A Novel FLT3 Inhibitor FI-700 Selectively Suppresses the Growth of Leukemia Cells with FLT3 Mutations", *Clin Cancer Res* 13(15):4575-4582 (2007).
Pawar et al. "Synthesis of 2,4,5-Trisubstituted Pyrimidines", *Indian Journal of Heterocyclic Chemistry* 20(12):133-136 (2010).
Aso et al. "Discovery of pyrrolo[2,3-d]pyrimidin-4-ones as corticotropin-releasing factor 1 receptor antagonists with a carbonyl-based hydrogen bonding acceptor", *Bioorganic & Medicinal Chemistry Letters* 21(8):2365-2371 (2011) (Abstract Only).
Verma et al. "Targeting Axl and Mer Kinases in Cancer", *Mol Cancer Ther* 10(10) 1763-73 (2011).
Cancer Drug Design and Discovery Neidle, Stephen, ed. (Elsevier/Academic Press, 2008) pp. 427-431.
Notification Concerning Transmittal of International Preliminary Report on Patentability corresponding to International Application No. PCT/US2015/024381 mailed Oct. 20, 2016.
Notification Concerning Transmittal of International Preliminary Report on Patentability corresponding to International Application No. PCT/US2015/024362 mailed Oct. 20, 2016.
Notification Concerning Transmittal of International Preliminary Report on Patentability corresponding to International Application No. PCT/US2015/024328 mailed Oct. 20, 2016.
Notification Concerning Transmittal of International Preliminary Report on Patentability corresponding to International Application No. PCT/US2015/024258 mailed Oct. 13, 2016.
Notification Concerning Transmittal of International Preliminary Report on Patentability corresponding to International Application No. PCT/US2015/024373 mailed Oct. 20, 2016.
Notification Concerning Transmittal of International Preliminary Report on Patentability corresponding to International Application No. PCT/US2015/024380 mailed Oct. 20, 2016.
Notification Concerning Transmittal of International Preliminary Report on Patentability corresponding to International Application No. PCT/US2015/024301 mailed Oct. 20, 2016.

* cited by examiner

MERTK-SPECIFIC PYRAZOLOPYRIMIDINE COMPOUNDS

CROSS-REFERENCE TO RELATED APPLICATIONS

This application claims the benefit of U.S. Provisional Application No. 61/978,268 filed Apr. 11, 2014, U.S. Provisional Application No. 61/978,281 filed Apr. 11, 2014, U.S. Provisional Application No. 61/978,290 filed Apr. 11, 2014, U.S. Provisional Application No. 61/978,321 filed Apr. 11, 2014, U.S. Provisional Application No. 61/978,443 filed Apr. 11, 2014, U.S. Provisional Application No. 61/978,485 filed Apr. 11, 2014, U.S. Provisional Application No. 61/978,513 filed Apr. 11, 2014, U.S. Provisional Application No. 61/994,384 filed May 16, 2014, and U.S. Provisional Application No. 62/088,159 filed Dec. 5, 2014. The entirety of each of these applications is hereby incorporated by reference for all purposes.

GOVERNMENT INTEREST

The U.S. Government has rights in this invention by virtue of support under Contract No. HHSN261200800001E awarded by the National Cancer Institute, National Institute of Health.

FIELD OF THE INVENTION

The present invention includes pyrazolopyrimidine compounds that selectively inhibit Mer tyrosine kinase (MerTK) activity and/or Tyro3 tyrosine kinase activity, and use of these pyrazolopyrimidine compounds as anti-cancer agents, immunostimulatory and immunomodulatory agents, anti-platelet agents, anti-infective agents, and as adjunctive agents in combination with chemotherapeutic, radiation or other standard of care for neoplasms.

BACKGROUND OF THE INVENTION

MerTK is a member of a receptor tyrosine kinase (RTK) family known as TAM, which also includes AXL and TYRO3. Each member of the TAM family contains an extracellular domain, a transmembrane domain and a conserved intracellular kinase domain. MerTK was first discovered in the laboratory of H. Shelton Earp at the University of North Carolina in 1994 (Graham et al., Cloning and mRNA expression analysis of a novel human protooncogene, c-mer. *Cell Growth Differ* 5, 647-657 (1994)). The TAM family members undergo ligand-induced homodimerization, followed by catalytic tyrosine kinase activation and intracellular signaling. Cross-phosphorylation has also been demonstrated within this RTK family, suggesting heterodimerization can occur also. These RTKs are widely expressed in many epithelial tissues and in cells of the immune, nervous, and reproductive systems. MerTK was given its name by the Earp laboratory because it was found to be expressed in monocytes and in tissues of epithelial and reproductive tissue.

As described in more detail below, ligand-bound MerTK can complex with phosphatidyl serine and it binds apoptotic cells which triggers ingestion and suppresses inflammatory cytokines. It is aberrantly expressed in certain cancers (for example, acute leukemia (ALL and AML) and some solid tumors (for example melanoma, breast cancer, colon cancer, non-small cell lung carcinoma, glioblastoma and others).

The MerTK ligands include growth arrest-specific 6 protein (GAS6; Chen, et al; *Oncogene* (1997) 14, 2033-2039), protein-S, tubby and tubbylike protein-1 (TULP1), and galectin-3. Several of these ligands are present in serum and expressed locally in a number of tissues. These ligands bind to the extracellular domain of MerTK, resulting in tyrosine kinase activation.

Since the discovery of MerTK in the Earp laboratory in 1994, there has been a growing body of literature and patents that suggest the possibility of MerTK as a drugable target for a number of indications.

MerTK is ectopically expressed or overexpressed in a number of hematologic and epithelial malignant cells. Expression of MerTK and GAS6 correlates with poor prognosis and/or chemoresistance in these tumor types. The mechanisms by which increased MerTK signaling in tumor cells contributes to tumor malignancy, however, remain unclear.

WO2013/052417 titled "Pyrrolopyrimidine Compounds for the Treatment of Cancer" filed by Wang, et al., and assigned to the University of North Carolina describe pyrrolopyrimidines with MerTK inhibitory activity for the treatment of tumors such as myeloid leukemia, lymphoblastic leukemia, melanoma, breast, lung, colon, liver, gastric, kidney, ovarian, uterine and brain cancer, wherein the pyrrolopyrimidines have the general structures below, with R substituents as defined in the those applications:

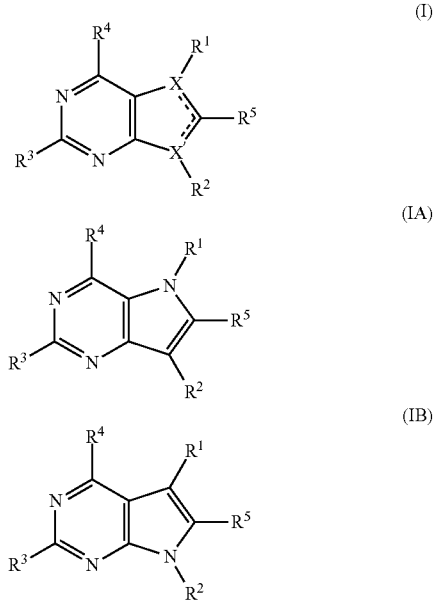

In November 2013, Dr. Stephen Frye presented data showing the inhibitory effects of a pyrrolopyrimidine compound (UNC2025) in non-small cell lung cancer cell lines, MerTK-expressing AML cell lines, and MerTK-negative AML cell lines. In addition, the effects of UNC2025 was analyzed in an ALL 697 cell line xenograft model and a FLT3-ITD AML patient xenograft model. Frye, S. "Academic Drug Discovery and Chemical Biology", Presentation at Northwestern's 18th Annual Drug Discovery Symposium. November 2013. The structure of the pyrrolopyrimidine compound UNC2025 is:

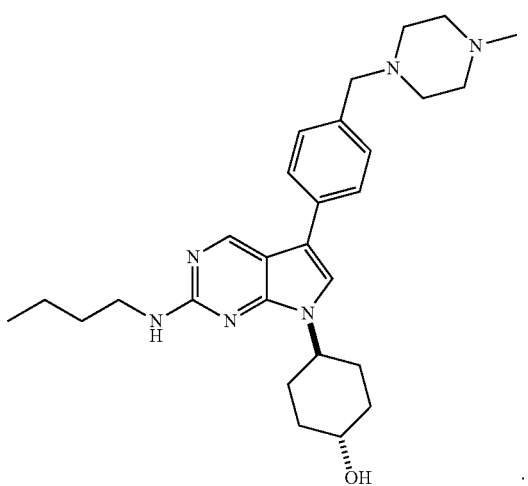

WO2011/146313 and WO2014/062774, both titled "Pyrazolopyrimidine Compounds for the Treatment of Cancer" filed by Wang, et al., and assigned to the University of North Carolina describe pyrazolopyrimidines with MerTK inhibitory activity for the treatment of tumors such as myeloid leukemia, lymphoblastic leukemia, melanoma, breast, lung, colon, liver, gastric, kidney, ovarian, uterine and brain cancer, wherein the pyrazolopyrimidines have the general structures below, with R substituents as defined in the those applications:

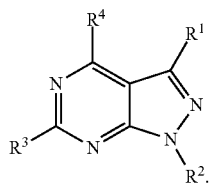

WO2014/062774 further discloses pyrazolopyrimidine compounds for use in a method of treating or inhibiting blood clot formation.

In January 2012, Liu, J, et al., published a comparison of the activity of forty four pyrazolopyrimidine compounds against MerTK, Axl and Tyro3 kinases. One of these compounds (UNC569) was tested for inhibition of MerTK autophosphorylation in human B-ALL cells ("Discovery of Novel Small Molecule MerTK Kinase Inhibitors for the Treatment of Pediatric Acute Lymphoblastic Leukemia." *ACS Med Chem Lett.* 2012 Feb. 9; 3(2):129-134.). In May 2013, *Schlegel*, et al., published results on the pyrazolopyrimidine compound UNC1062, which reduced activation of MERTK-mediated downstream signaling, induced apoptosis in culture, reduced colony formation in soft agar, and inhibited invasion of melanoma cells ("MERTK receptor tyrosine kinase is a therapeutic target in melanoma." *J Clin Invest.* 2013 May; 123(5):2257-67).

In December 2013, Zhang, W., et al., also published a comparison of the activity of forty six 5-arylpyrimidine based compounds for treatment of tumors ("Pseudo-cyclization through intramolecular hydrogen bond enables discovery of pyridine substituted pyrimidines as new MerTK kinase inhibitors." *J. Med. Chem., vol.* 56:9683-9692, 2013). These pyrimidine compounds were identified using a pseudo-ring replacement strategy based on the previously identified pyrazolopyrimidine MerTK inhibitor, UNC569.

In July 2013, Liu, J, et al. published the first evidence of anti-tumor activity mediated by a member of this novel class of inhibitors. Specifically, the pyrazolopyrimidine compound UNC1062 inhibited MerTK phosphorylation and colony formation in soft agar ("UNC1062, a new and potent MerTK inhibitor." *Eur J Med Chem.* 2013 July; 65:83-93).

In November 2013, Christoph, S. et al., published effects of a pyrazolopyrimidine (UNC569) in ALL and ATRT (atypical teratoid/rhabdoid tumors (ATRT) ("UNC569, a novel small-molecule MerTK inhibitor with efficacy against acute lymphoblastic leukemia in vitro and in vivo." *Mol Cancer Ther.* 2013 November; 12(11):2367-77). The MerTK inhibitors UNC569 and UNC1062 have the following structures:

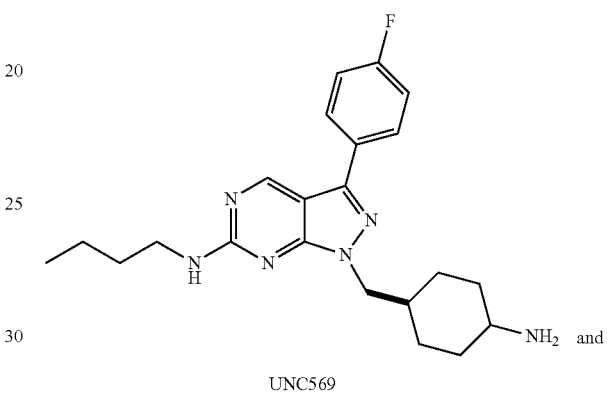

UNC569 and

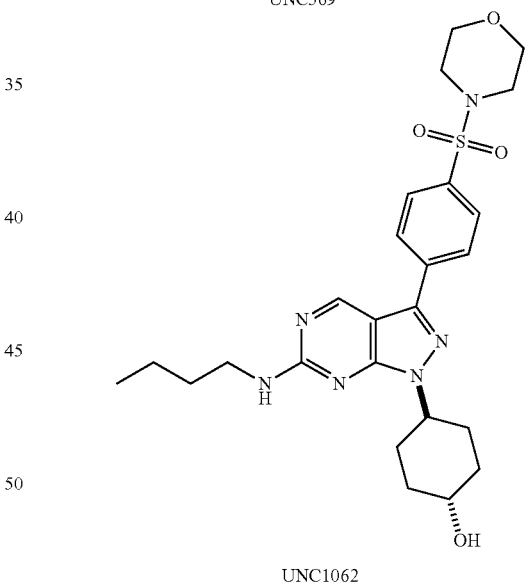

UNC1062

An important observation was made in 2013 that MerTK−/− knock-out mice are less susceptible to tumor growth than normal mice. MerTK is normally expressed in myeloid lineage cells where it acts to suppress pro-inflammatory cytokines following ingestion of apoptotic material. It was found that MerKT−/− leukocytes exhibit lower tumor cell-induced expression of wound healing cytokines (IL-10 and GAS6) and enhanced expression of acute inflammatory cytokines (IL-12 and IL-6). Further, intratumoral CD8+ lymphocytes are increased. The loss of MerTK in the tumor microenvironment in MerTK−/− mice slowed the establishment, growth, and metastasis of mammary tumors and melanomas in immune competent, syngeneic mice. Cook, R. S. et al., MerTK inhibition in tumor leukocytes decreases tumor growth and metastasis, *J Clin Invest* 123, 3231-3242 (2013).

Linger et al. have also presented data demonstrating increased MerTK expression in E2A-PBX11 and other cytogenetic subgroups of B-acute lymphoblastic leukemia (B-ALL), and that MerTK inhibition may attenuate prosurvival and proliferation signaling. Linger et al., MerTK receptor tyrosine kinase is a therapeutic target in pre-B-cell acute lymphoblastic leukemia, *Blood*, vol. 122(9):1599-1609, 2013.

Lee-Sherick, et al. ("Efficacy of a Mer and Flt3 tyrosine kinase small molecule inhibitor, UNC1666, in acute myeloid leukemia", *Oncotarget*, Advance Publications 2015 Feb. 10, 2015) have reported that UNC 1666 (a pyrrolopyrimidine) decreases oncogenic signaling and myeloid survival in AML.

Paolino et al. have reported on the treatment of wild-type NK cells with a newly developed small molecule TAM kinase inhibitor, LDC1267, that conferred therapeutic potential and efficiently enhancing anti-metastatic NK cell activity in vivo. Oral or intraperitoneal administration using this TAM inhibitor markedly reduced murine mammary cancer and melanoma metastases dependent on NK cells. See, Paolino, M., et al., The E3 ligase Cbl-b and TAM receptors regulate cancer metastasis via natural killer cells, Nature, vol. 507:508-512, 2014. LDC1267 is a highly selective TAM kinase inhibitor with $IC_{50}$ of <5 nM, 8 nM, and 29 nM for MerTK, Tyro3, and Axl, respectively, and has the chemical structure:

LDC1267

TAM receptor tyrosine kinases have been investigated for their involvement in certain infectious diseases. Shimojima, et al., reported the involvement of members of the Tyro3 receptor tyrosine kinase family, Axl, Dkt and MerTK, in the cell entry of filoviruses Ebolavirus and Marburgvirus, and concluded that each Tyro3 family member is likely a cell entry factor in the infection ("Tyro3 Family-mediated Cell Entry of Ebola and Marburg Viruses" *Journal of Virology*, October 2006 p. 10109-10116).

U.S. Pat. No. 8,415,361 to Lemke, et al. (claiming priority to a Nov. 9, 2007 provisional application), assigned to The Salk Institute for Biological Studies, describes the use of TAM receptor inhibitors as antimicrobials. In particular, the '361 patent reports that inhibition of the TAM pathway in virally infected macrophages from TAM triple knock-out mice leads to reduced levels of infection with a variety of pseudotyped viruses with either filoviral, retroviral or rhabdoviral glycoproteins. Brindley, et al., reported that in a bioinformatics-based screen for cellular genes that enhance Zaire ebolavirus (ZEBOV) transduction, AXL mRNA expression strongly correlated with ZEBOV infection ("Tyrosine kinase receptor Axl enhances entry of Zaire ebolavirus without direct interactions with the viral glycoprotein" *Virology*, 415 (2011) 83-84).

Morizono, et al, published that Gas6 mediates binding of the virus to target cells by bridging virion envelope phosphatidyl serine to Axl on the target cells. Replication of vaccinia virus, which was previously reported to use apoptotic mimicry to enter cells, is enhanced by Gas6, and Morizono asserts that these results reveal an alternative molecular mechanism of viral entry that can broaden host range and enhance infectivity of enveloped viruses ("The Soluble Serum Protein Gas6 Bridges Virion Envelope Phosphatidylserine to the TAM Receptor Tyrosine Kinase Axl to mediate Viral Entry" *Cell Host & Microbe* 9, 286-298, 2011). In 2014, Morizono and Chen reported that virus binding by viral envelope phosphatidyl serine is a viral entry mechanism generalized to a number of families of viruses (Morizono and Chen, "Role of Phosphatidyl Receptors in Enveloped Virus Infection", *J. Virology* Vol 88(8), 4275-4290 (Jan. 29, 2014)).

WO2013/124324 filed by Amara et al. (priority date Feb. 21, 2012), and assigned to Institut National De La Sante et De La Recherche Medicale, reports that Dengue virus is mediated by the interaction between phosphatidylserine at the surface of the Dengue viral envelope and TAM receptors present at the surface of the host cell, and that such interaction can be blocked, thereby inhibiting entry of Dengue into host cells. They also report that the interaction between phosphatidyl serine and TAM receptors is used by other flaviviruses such as Yellow Fever, West Nile and perhaps Chikungunya. Amara focuses on antisense, siRNA and antibody approaches.

Similarly, Bhattacharayya et al., reports that several human viruses, for example Ebola, Dengue, and HIV, externalize PtdSer on their capsid during budding and use phosphatidylserine to bind to and activate TAM RTKs in the presence of TAM ligands, allowing entry of the virus into cells and furthermore, activation of MerTK in macrophages in response to viral particles expressing PtdSer stimulates an anti-inflammatory cytokine profile as if apoptotic material was being ingested, thereby inhibiting the anti-viral immune response. Bhattacharayya et al observe that TAM receptors are engaged by viruses to attenuate type 1 interferon signaling ("Enveloped viruses disable innate immune responses in dendritic cells by direct activation of TAM receptors", *Cell Host & Microbe* 14, 136,-147 (2013)). See also Meertens, L. et al. The TIM and TAM families of phosphatidylserine receptors mediate dengue virus entry. *Cell Host Microbe* 12, 544-557, doi:10.1016/j.chom.2012.08.009 (2012). Mercer, J. & Helenius, A. Vaccinia virus uses macropinocytosis and apoptotic mimicry to enter host cells. *Science* 320, 531-535, doi:10.1126/science.1155164 (2008).

Bernsmeier, et al., have noted that characteristics of decompensated cirrhosis and acute-on-chronic liver failure (ACLF) include susceptibility to infection, immune paresis and monocyte dysfunction. The authors found that the number of monocytes and macrophages that expressed MerTK was greatly increased in circulation, livers and lymph nodes of patients with ACLF. They found that addition of a substituted pyrrazolopyrimidine UNC569 (see WO 2011/146313 filed by Wang, et al., and assigned to University of North Carolina at Chapel Hill, page 25) restored production of inflammatory cytokines. Bernsmeier, et al., "Patients with Acute-on-Chronic Liver Failure Have Increased Numbers of Regulatory Immune Cells Expressing the Receptor Tyrosine Kinase MERTK", Gastroenterology 2015; 1-13.

TAM (Tyro3-Axl-MerTK) receptor tyrosine kinases have also been investigated for their involvement in platelet aggregation. In 2004, Chen et al, from the Johnson & Johnson Pharmaceutical Research and Development, published that MerTK, presumably through activation by its ligand Gas6, participates in the regulation of platelet function in vitro and platelet-dependent thrombosis in vivo. Chen, et al, "*Mer Receptor tyrosine Kinase Signaling Participates in Platelet Function*", Arterioscler. Thromv Vasc. Biol. 1118-1123 June 2004. Chen reported that PtdSer on aggregating platelets activates MerTK, helping to stabilize clot formation. MerTK knockout mice have decreased platelet aggregation while maintaining normal bleeding times and coagulation parameters. Consequently, these mice appear to be protected from thrombosis without concomitant increased spontaneous bleeding (see also Angelillo-Scherrer A et al., Role of Gas6 receptors in platelet signaling during thrombus stabilization and implications for antithrombotic therapy. J. Clin. Invest. 2005, 115 (2), 237-246).

In 2007, Sather, et al., reported that membrane-bound MerTK is cleaved in the extracellular domain via a metalloproteinase to produce a soluble MerTK that decreased platelet aggregation in vitro and prevented fatal collagen/epinephrine-induced thromboembolism. "A soluble form of the MerTK receptor tyrosine kinase inhibits macrophage clearance of apoptotic cells and platelet aggregation", *Blood*, Vol 109(3): 1026-1033).

It is an object of the invention to identify new compounds, compositions and methods for the treatment of a tumor, cancer or other neoplasm. It is another object of the invention to identify new compositions with improved selectivity for MerTK.

It is another object of the invention to identify new compounds, compositions and methods for the treatment of disorders that can be treated with immunosuppression, or which would benefit from immunostimulatory therapy.

It is another object of the invention to identify new compounds, compositions and methods for the treatment of infectious diseases.

It is yet another object of the invention to identify new compounds, compositions and methods for the treatment of thrombosis.

SUMMARY OF THE INVENTION

It has been discovered that a compound of Formula I as described herein is a superior inhibitor of the Mer tyrosine kinase. Surprisingly, substituents at the $R^7$ and $R^8$ positions of a compound of Formula I as described herein play a significant role in a compound's ability to inhibit MerTK and improve the selectivity index for inhibition of MerTK over Flt3 and Axl. In one embodiment, $R^7$ is alkyl. In one embodiment, $R^7$ is methyl. In another embodiment, $R^7$ is ethyl.

It has also been discovered that the stereochemistry of the carbon attached to the $R^7$ and $R^8$ substituents plays an important role in a compound's ability to inhibit MerTK and improve the selectivity index for inhibition of MerTK over Flt3 and Axl. In one embodiment, the carbon attached to the $R^7$ and $R^8$ substituents is in the S configuration. In one embodiment, the carbon attached to the $R^7$ and $R^8$ substituents is in the R configuration.

A first aspect of the present invention provides active compounds of Formula I:

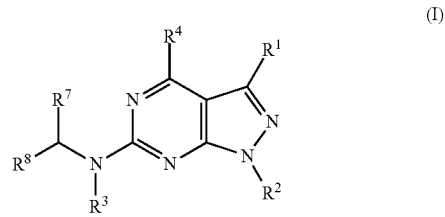

wherein:

$R^1$ is aryl such as phenyl or heteroaryl (in some embodiments substituted 1, 2 or 3 times with heterocycloalkylalkyl, which heterocycloalkylalkyl is substituted or unsubstituted, for example substituted from 1 to 3 times with halo or alkyl).

$R^2$ is $-R^5R^6$, where $R^5$ is a covalent bond or $C_1$ to $C_3$ alkyl and $R^6$ is cycloalkyl, heterocycloalkyl, aryl, heteroaryl or alkyl, and wherein $R^6$ is optionally substituted from one to two times with independently selected polar groups from the group consisting of halo, hydroxy, alkoxy, carboxy, nitro, cyano; secondary and tertiary amino; amido, ureido, sulfonamido, sulfinyl, sulfhydryl, silyl, S-sulfonamido, N-sulfonamido, C-carboxy, O-carboxy, C-amido, N-amido, sulfonyl, N-tert-butoxycarbonyl, phosphono, morpholino, piperazinyl, tetrazolo, alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates) and the polar group can be an ionic group, for example, an anionic or cationic group, including but not limited to carboxylate, sulfonate, phosphate, N-oxide, quaternized heterocyclic amine, for example, imidazolium and pyridinium; uronic acids, carboxylic acid, sulfonic acid, guanidinium, phosphoric acid, phosphonic acid, phosphatidyl choline, phosphonium, borate, and sulfate;

$R^3$ is H, alkyl, arylalkyl; cycloalkylalkyl, heterocycloalkylalkyl, heteroarylalkyl, and alkoxyalkyl, each of which is optionally substituted one, two or three times with independently selected polar groups (typically $R^3$ is H);

$R^4$ is H, loweralkyl, halo, or loweralkoxy;

$R^7$ is alkyl, arylalkyl; cycloalkylalkyl, heterocycloalkylalkyl, heteroarylalkyl, and alkoxyalkyl, each of which is optionally substituted one, two or three times with independently selected polar groups (in some embodiments $R^7$ is preferably methyl, ethyl, propyl, fluoromethyl, difluoromethyl, hydroxymethyl, fluoroethyl, difluoroethyl, hydroxymethyl, hydroxyethyl, $CD_2H$, $CDH_2$, $CF_3$, $CD_3$, etc.);

$R^8$ is alkyl, arylalkyl; cycloalkylalkyl, heterocycloalkylalkyl, heteroarylalkyl, and alkoxyalkyl, preferably alkyl or cycloalkyl, each of which is optionally substituted one, two or three times with independently selected polar groups (e.g., halo such as fluoro; hydroxyl, etc.);

or a pharmaceutically acceptable composition, salt, isotopic analog, or prodrug thereof.

In another aspect of the invention, the present invention provides active compounds of Formula I":

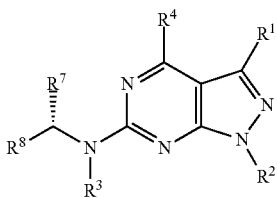

(I')

wherein:
$R^1$, $R^2$, $R^3$, $R^4$, $R^7$ and $R^8$ are as defined herein.

In another aspect of the invention, the present invention provides active compounds of Formula I":

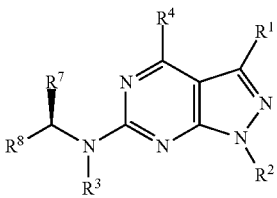

(I")

wherein:
$R^1$, $R^2$, $R^3$, $R^4$, $R^7$ and $R^8$ are as defined herein.

It has been discovered that a compound of Formula II as described herein is a superior inhibitor of the Mer tyrosine kinase. Surprisingly, substituents at the $R^{17}$ and $R^{18}$ positions of a compound of Formula I as described herein play a significant role in a compound's ability to inhibit MerTK and improve the selectivity index for inhibition of MerTK over Flt3 and Axl. In one embodiment, $R^{17}$ is alkyl. In one embodiment, $R^{17}$ is methyl. In another embodiment, $R^{17}$ is ethyl.

It has also been discovered that the stereochemistry of the carbon attached to the $R^{17}$ and $R^{18}$ substituents plays an important role in a compound's ability to inhibit MerTK and improve the selectivity index for inhibition of MerTK over Flt3 and Axl. In one embodiment, the carbon attached to the $R^{17}$ and $R^{18}$ substituents is in the S configuration. In one embodiment, the carbon attached to the $R^{17}$ and $R^{18}$ substituents is in the R configuration.

In another aspect of the invention, the present invention provides active compounds of Formula II:

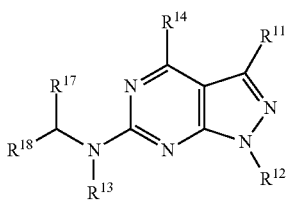

II wherein:
$R^{11}$ is $-R^9(R^{10})_n$, where $R^9$ is alkyl, alkenyl, -alkylaryl, heterocyclo, aryl, heteroaryl is $-R^9$ and $R^{10}$ is hydrogen, alkyl, haloalkyl, alkoxyalkyl, —O-alkylaryl, hydroxyalkyl, alkenyl, alkenyloxy, alkynyl, alkynyloxy, cycloalkyl, cycloalkylalkyl, cycloalkoxy, cycloalkylalkyloxy, heterocyclo, heterocycloalkyl, alkylheterocycloalkyl, heterocyclooxy, heterocyclolalkyloxy, aryl, arylalkyl, aryloxy, aryl- alkyloxy, heteroaryl, alkylheteroaryl, halo, hydroxyl, alkoxy, haloalkoxy, mercapto, alkyl-S(O)$_m$—, haloalkyl-S(O)$_m$—, alkenyl-S(O)$_m$—, alkynyl-S(O)$_m$—, cycloalkyl-S(O)$_m$—, cycloalkylalkyl-S(O)$_m$—, aryl-S(O)$_m$—, arylalkyl-S(O)$_m$—, heterocyclo-S(O)$_m$, heterocycloalkyl-S(O)$_m$—, amino, carboxy, alkylamino, —(CH$_2$)$_m$—NHalkyl, —(CH$_2$)$_m$—N(alkyl)$_2$, —(CH$_2$)$_m$—NH(CH$_2$)$_m$OH, —(CH$_2$)$_m$—NH(CH$_2$)$_m$cycloalkyl, —(CH$_2$)$_m$—NH(CH$_2$)$_{2-3}$heterocyclo, —(CH$_2$)$_m$—NH(CH$_2$)$_m$aryl, —(CH$_2$)$_m$—NH(CH$_2$)$_{2-3}$heteroaryl, —(CH$_2$)$_m$NH(CH$_2$)$_{2-3}$N(alkyl)$_2$, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, S(O)$_2$OR$^{19}$, —CONHNH$_2$, cyano, nitro, aminosulfonyl, COOH, sulfonamide, urea, alkoxyacylamino, aminoacyloxy, —C(CH$_2$)$_2$R$^{19}$, and wherein $R^{10}$ is optionally substituted one two or three times;

m=0, 1, 2 or 3;
n=0, 1 or 2;
$R^{12}$ is —$R^{15}R^{16}$, where $R^{15}$ is a covalent bond or $C_1$ to $C_3$ alkyl and $R^{16}$ is cycloalkyl, heterocycloalkyl, aryl, heteroaryl or alkyl, and wherein $R^{16}$ is optionally substituted one, two or three times from the group consisting of halo, hydroxy, alkoxy, carboxy, nitro, cyano; secondary and tertiary amino; amido, ureido, sulfonamido, sulfinyl, sulfhydryl, silyl, S-sulfonamido, N-sulfonamido, C-carboxy, O-carboxy, C-amido, N-amido, sulfonyl, N-tert-butoxycarbonyl, phosphono, morpholino, piperazinyl, tetrazolo, alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates) and the polar group can be an ionic group, for example, an anionic or cationic group, including but not limited to carboxylate, sulfonate, phosphate, N-oxide, quaternized heterocyclic amine, for example, imidazolium and pyridinium; uronic acids, carboxylic acid, sulfonic acid, guanidinium, phosphoric acid, phosphonic acid, phosphatidyl choline, phosphonium, borate, and sulfate;

$R^{13}$ is selected from the group consisting of hydrogen, deuterium, alkyl, alkenyl, alkynyl, aryl, arylalkyl, cycloalkyl, cycloalkylalkyl, heterocyclo, heterocycloalkyl, alkylheterocycloalkyl, heteroaryl, heteroarylalkyl, and alkoxyalkyl, each of which is optionally substituted one, two or three times (typically $R^{13}$ is H);

$R^{14}$ is H, loweralkyl, halo, or loweralkoxy;

$R^{17}$ is alkyl, haloalkyl, hydroxyalkyl, alkenyl, alkynyl, aryl, arylalkyl, cycloalkyl, cycloalkylalkyl, alkylheterocycloalkyl, heterocyclo, heterocycloalkyl, heteroaryl, heteroarylalkyl, and alkoxyalkyl, each of which is optionally substituted one, two or three times (in some embodiments $R^{17}$ is typically methyl, ethyl, propyl, fluoromethyl, difluoromethyl, trifluoromethyl, fluoroethyl, difluoroethyl, hydroxymethyl, hydroxyethyl, CD$_2$H, CDH$_2$, CF$_3$, CD$_3$, etc.);

$R^{18}$ is alkyl, haloalkyl, hydroxyalkyl, alkenyl, alkynyl, aryl, arylalkyl; cycloalkyl, cycloalkylalkyl, alkylheterocycloalkyl, heterocyclo, heterocycloalkyl, heteroaryl, heteroarylalkyl, and alkoxyalkyl, typically alkyl or cycloalkyl, each of which is optionally substituted one, two or three times; or $R^{17}$ and $R^{18}$ can form a cycloalkyl group that can be optionally substituted one, two or three times;

$R^{19}$ is selected from hydrogen, alkyl, alkenyl, alkynyl, aryl, arylalkyl, cycloalkyl, cycloalkylalkyl, heterocyclo, heterocycloalkyl, heteroaryl, or heteroarylalkyl;

or a pharmaceutically acceptable composition, salt, isotopic analog, or prodrug thereof.

In another aspect of the invention, the present invention provides active compounds of Formula IIa:

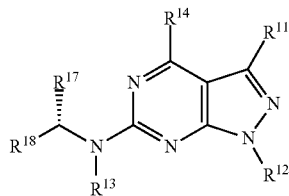

IIa wherein:
$R^{11}$, $R^{12}$, $R^{13}$, $R^{14}$, $R^{17}$ and $R^{18}$ are as defined herein.

In another aspect of the invention, the present invention provides active compounds of Formula IIb:

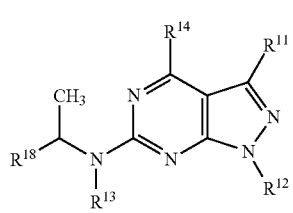

IIb wherein:
$R^{11}$, $R^{12}$, $R^{13}$, $R^{14}$, $R^{17}$ and $R^{18}$ are as defined herein.

In another aspect of the invention, the present invention provides active compounds of Formula IIc:

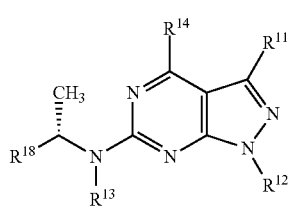

IIc

In another aspect of the invention, the present invention provides active compounds of Formula IId:

IId wherein:
$R^{11}$, $R^{12}$, $R^{13}$, $R^{14}$ and $R^{18}$ are as defined herein.

In another aspect of the invention, the present invention provides active compounds of Formula IIe:

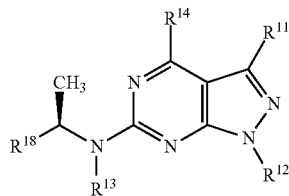

IIe wherein:
$R^{11}$, $R^{12}$, $R^{13}$, $R^{14}$, and $R^{18}$ are as defined herein.

In another aspect of the invention, the present invention provides active compounds of Formula IIf:

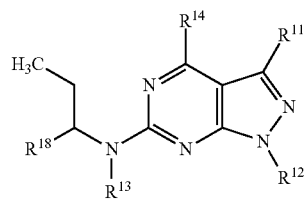

IIf wherein:
$R^{11}$, $R^{12}$, $R^{13}$, $R^{14}$ and $R^{18}$ are as defined herein.

In another aspect of the invention, the present invention provides active compounds of Formula IIg:

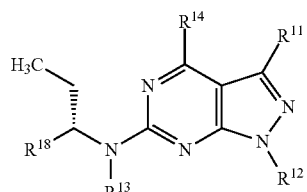

IIg wherein:
$R^{11}$, $R^{12}$, $R^{13}$, $R^{14}$ and $R^{18}$ are as defined herein.

In another aspect of the invention, the present invention provides active compounds of Formula IIh:

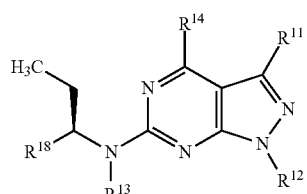

IIh wherein:
$R^{11}$, $R^{12}$, $R^{13}$, $R^{14}$, and $R^{18}$ are as defined herein.

It has also been discovered that the substituents at the $R^{20}$ and $R^{21}$ positions of active compounds as described herein play a role in a compound's ability to inhibit MerTK and Tyro3 tyrosine kinase, and improve the selectivity index for inhibition of Tyro3 over MerTK. In one embodiment, $R^{20}$ is alkyl. In one embodiment, $R^{20}$ is ethyl.

It has also been discovered that the stereochemistry of the carbon attached to the $R^{20}$ and $R^{21}$ substituents plays a role in a compound's ability to inhibit MerTK and Tyro3 tyrosine kinases, and improve the selectivity index for inhibition of Tyro3 over MerTK. In one embodiment, the carbon attached to the $R^{20}$ and $R^{21}$ substituents is in the S configuration. In one embodiment, the carbon attached to the $R^{20}$ and $R^{21}$ substituents is in the R configuration.

In another aspect of the invention, the present invention provides active compounds of Formula III:

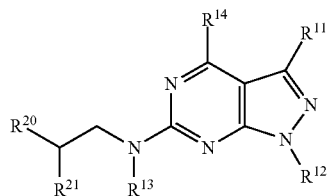

wherein:

$R^{20}$ is alkyl, haloalkyl, hydroxyalkyl, arylalkyl, cycloalkylalkyl, alkylheterocycloalkyl, heteroarylalkyl, and alkoxyalkyl, each of which is optionally substituted (in some embodiments $R^{20}$ is typically methyl, ethyl, propyl, fluoromethyl, difluoromethyl, fluoroethyl, difluoroethyl, hydroxymethyl, hydroxyethyl, $CD_2H$, $CDH_2$, $CF_3$, $CD_3$, etc.);

$R^{21}$ is alkyl, haloalkyl, hydroxyalkyl, alkenyl, alkynyl, aryl, arylalkyl, cycloalkyl, cycloalkylalkyl, alkylheterocycloalkyl, heterocyclo, heterocycloalkyl, heteroaryl, heteroarylalkyl, and alkoxyalkyl, typically alkyl or cycloalkyl, each of which is optionally substituted one, two or three times;

$R^{11}$, $R^{12}$, $R^{13}$ and $R^{14}$ are as defined herein.

In another aspect of the invention, the present invention provides active compounds of Formula IIIa:

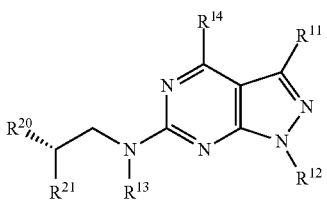

wherein:
$R^{11}$, $R^{12}$, $R^{13}$, $R^{14}$, $R^{20}$ and $R^{21}$ are as defined herein.

In another aspect of the invention, the present invention provides active compounds of Formula IIIb:

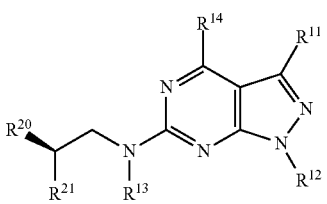

wherein:
$R^{11}$, $R^{12}$, $R^{13}$, $R^{14}$, $R^{20}$ and $R^{21}$ are as defined herein.

In another aspect of the invention, the present invention provides active compounds of Formula IIIc:

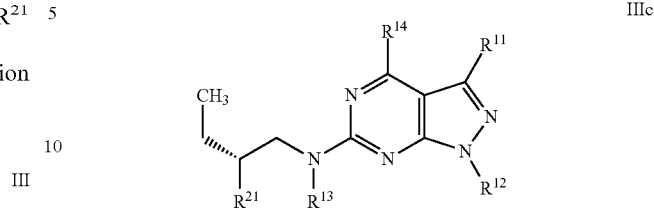

wherein:
$R^{11}$, $R^{12}$, $R^{13}$, $R^{14}$ and $R^{21}$ are as defined herein.

In another aspect of the invention, the present invention provides active compounds of Formula IIId:

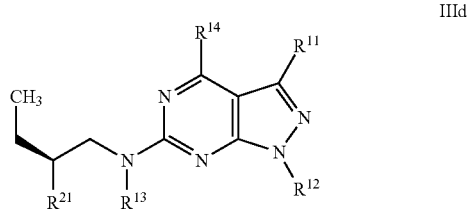

wherein:
$R^{11}$, $R^{12}$, $R^{13}$, $R^{14}$ and $R^{21}$ are as defined herein.

In another aspect of the invention, the present invention provides active compounds of Formula IIIe:

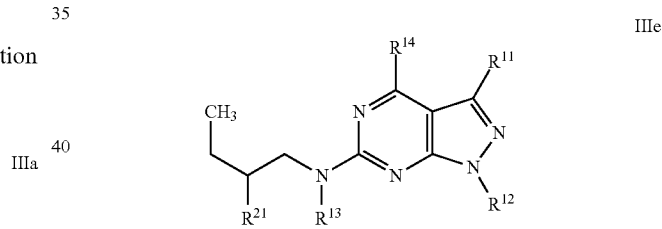

wherein:
$R^{11}$, $R^{12}$, $R^{13}$, $R^{14}$ and $R^{21}$ are as defined herein.

The Mer tyrosine kinase inhibitors disclosed herein are useful as anti-tumor agents, anti-neoplastic agents, anti-cancer agents, immunomodulatory agents, immunostimulatory agents, anti-infective agents, anti-thrombotic, and/or anti-clotting agents. A further aspect of the invention is a method to treat a cancer or tumor or other condition in a subject in need thereof, comprising administering to said subject an active compound as described herein in an amount effective to treat the condition. In one embodiment, the subject is a human.

A further aspect of the invention is an active compound as described herein in a pharmaceutically acceptable carrier.

The present invention provides at least the following:
(a) A compound of Formula I, II, or III as described herein, or a pharmaceutically acceptable composition, salt, isotopic analog, or prodrug thereof (each of which includes all subgenuses and species thereof considered individually and specifically described).
(b) A compound of Table 1 as described herein, or a pharmaceutically acceptable composition, salt, isotopic analog, or prodrug thereof.

(c) Use of a compound of Formula I, II, or III as described herein, or a pharmaceutically acceptable composition, salt, isotopic analog, or prodrug thereof, for use in treating a tumor, including cancer.

(d) Use of a compound of Table 1 as described herein, or a pharmaceutically acceptable composition, salt, isotopic analog, or prodrug thereof, for use in treating a tumor, including cancer.

(e) Use of one or more of the compounds disclosed herein in an effective immunostimulatory dosage for adjunctive antineoplastic therapy as a means to increase the efficacy of the antineoplastic standard of care therapies, such as chemotherapeutic compounds or radiation.

(f) Use of one or more of the compounds disclosed herein in an effective immunostimulatory dosage for use as an anti-infective agent.

(g) Use of one or more of the compounds disclosed herein in an effective immunostimulatory dosage for use as an anti-viral agent.

(h) Use of one or more of the compounds disclosed herein in an effective immunostimulatory dosage for use as an anti-bacterial agent.

(i) Use of one or more of the compounds disclosed herein in an effective immunostimulatory dosage for adjunctive antineoplastic therapy as a means to increase the efficacy of the antineoplastic standard of care therapies, such as chemotherapeutic compounds or radiation, in combination with an additional chemotherapeutic agent.

(j) Use of one or more of the compounds disclosed herein in an effective immunostimulatory dosage for use as an anti-infective agent, in combination with an additional anti-infective agent.

(k) Use of one or more of the compounds disclosed herein in an effective immunostimulatory dosage for use as an anti-viral agent, in combination with an additional anti-viral agent.

(l) Use of one or more of the compounds disclosed herein in an effective immunostimulatory dosage for use as an anti-bacterial agent, in combination with an additional anti-bacterial agent.

(m) Use of one or more of the compounds as described herein in an effective dosage to treat a host with a selected MerTK (+/+) tumor, including cancer.

(n) Use of any of the active compounds described herein, or a pharmaceutically acceptable composition, salt, isotopic analog, or prodrug thereof, for the treatment of a MERTK-negative (−/−) tumor, including cancer.

(o) Use of any of the active compounds described herein, or a pharmaceutically acceptable composition, salt, isotopic analog, or prodrug thereof, to treat a host that has an immunosuppressed microenvironment surrounding diseased tissue, by re-programming the microenvironment to a pro-inflammatory environment. As one example, the host is in need of treatment because it has tumor associated macrophages that are protecting tumor cells.

(p) Use of a compound of Formula I, II, or III as described herein, and pharmaceutically acceptable salts and prodrugs thereof, for use in treating a thrombotic or clotting disorder.

(q) Use of a compound of Formula I, II, or III as described herein, and pharmaceutically acceptable salts and prodrugs thereof, for use in treating an infectious disease, including a viral disease or a bacterial disease.

(r) A compound as described herein, or a pharmaceutically acceptable composition, salt, isotopic analog, or prodrug thereof, for use in combination with a second chemotherapeutic agent in a subject undergoing a therapeutic regime to treat a tumor, including cancer.

(s) A compound as described herein, for use in the manufacture of a medicament for treatment of a tumor, including cancer.

(t) A compound as described herein, for use in the manufacture of a medicament for treatment of a MerTK+/+ tumor, including cancer.

(u) A compound as described herein, for use in the manufacture of a medicament for treatment of a MerTK−/− tumor, including cancer.

(v) A compound as described herein, for use in the manufacture of a medicament for immunostimulatory therapy.

(w) A compound as described herein, for use in the manufacture of a medicament for immunomodulatory therapy.

(x) A compound as described herein, for use in the manufacture of a medicament for immunostimulatory therapy in combination with chemotherapeutic or radiation standard of care.

(y) A compound as described herein, for use in the manufacture of a medicament for immunomodulatory therapy in combination with chemotherapeutic or radiation standard of care.

(z) A compound as described herein, for use in the manufacture of a medicament for use in treating an infectious disease, including a viral disease or a bacterial disease.

(aa) A compound as described herein, for use in the manufacture of a medicament for the treatment of a thrombotic or clotting disorder.

(bb) A process for manufacturing a medicament as described in (s) through (aa).

(cc) A pharmaceutical formulation comprising an effective host-treating amount of the Formula I, II, or III or a pharmaceutically acceptable salt or prodrug thereof together with a pharmaceutically acceptable carrier or diluent.

(dd) Processes for the manufacture of the compounds of Formula I, II, or III and salts, compositions, dosage forms thereof.

(ee) Processes for the preparation of therapeutic products that contain an effective amount of Formula I, II, or III, as described herein.

DETAILED DESCRIPTION

1. Terminology

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixtures of enantiomers, diastereomers, tautomers, racemates and other isomers, such as rotamers, as if each is specifically described.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

Isotopic Substitution

In one embodiment, the present invention includes active compounds described herein, and the use of these compounds with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures. Alternatively or in addition, isotopes of carbon, e.g., $^{13}C$ and $^{14}C$, may be used. A typical isotopic substitution is deuterium for hydrogen at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one embodiments deuterium is 90, 95 or 99% enriched at a desired location. Unless otherwise stated, the enrichment at any point is above natural abundance and enough to alter a detectable property of the drug in a human.

In one embodiment, the substitution of a hydrogen atom for a deuterium atom occurs within an R group when at least one of the variables within the R group is hydrogen (e.g., $^2H$ or D) or alkyl (e.g., $CD_3$). For example, when any of R groups are, or contain for example through substitution, methyl or ethyl, the alkyl residue is typically deuterated, e.g., $CD_3$, $CH_2CD_3$ or $CD_2CD_3$. In certain other embodiments, when any of the above mentioned R groups are hydrogen, the hydrogen may be isotopically enriched as deuterium (i.e., $^2H$).

A dash ("-") that is not between two letters or symbols is used to indicate a point of attachment for a substituent. For example, —(C═O)NH$_2$ is attached through carbon of the keto (C═O) group.

"Alkyl" as used herein alone or as part of another group, refers to a straight or branched chain hydrocarbon containing from 1 to 10 carbon atoms. In one embodiment, the alkyl contains from 1 to about 10 carbon atoms, more generally from 1 to about 6 carbon atoms or from 1 to about 4 carbon atoms. In certain embodiments, the alkyl is $C_1$-$C_3$ or $C_1$-$C_8$. The specified ranges as used herein indicate an alkyl group having each member of the range described as an independent species. For example, the term $C_1$-$C_3$ alkyl as used herein indicates a straight or branched alkyl group having from 1, 2, or 3 carbon atoms and is intended to mean that each of these is described as an independent species. For example, the term $C_1$-$C_3$alkyl as used herein indicates a straight or branched alkyl group having from 1, 2, or 3 carbon atoms and is intended to mean that each of these is described as an independent species. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments typically, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "lower-alkyl" is intended to include both substituted and unsubstituted alkyl or loweralkyl unless otherwise indicated and these groups may be substituted with groups selected from halo (e.g., haloalkyl), alkyl, haloalkyl, hydroxyalkyl, alkenyl, alkynyl, cycloalkyl (including spiroalkyl, e.g., —C(CH$_2$)$_{24}$ spiroalkyl), cycloalkylalkyl, aryl, arylalkyl, heterocyclo, heterocycloalkyl, alkylheterocycloalkyl, heteroaryl, alkylheteroaryl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, —(CH$_2$)$_m$—NH(CH$_2$)$_m$CH$_3$, —(CH$_2$)$_m$—NH(CH$_2$)$_m$OH, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. In one embodiment, alkyl or loweralkyl can be substituted with groups selected from a polar group, —(CH$_2$)$_m$—N(R$^{50}$)$_2$, —(CH$_2$)$_m$—NH(CH$_2$)$_m$R$^{50}$, —(CH$_2$)$_m$ NH(CH$_2$)$_{2-3}$N(R$^{50}$)$_2$, —S(O)$_2$OR$^{50}$, —CONHNHR$^{50}$, aminosulfonyl —C(CH$_2$)$_2$R$^{50}$ wherein each R$^{50}$ is independently selected from hydrogen, alkyl, alkenyl, alkynyl, aryl, arylalkyl, cycloalkyl, cycloalkylalkyl, heterocyclo, heterocycloalkyl, heteroaryl, or heteroarylalkyl.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise. In one embodiment, as used herein, the term "cycloalkyl" refers to a saturated or unsaturated hydrocarbon mono- or multi-ring, e.g., fused, bridged, or Spiro rings system having 3 to 15 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, and adamantyl. In another embodiment, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene and adamantane. Cycloalkyl groups can also be partially unsaturated, having one or more double bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. These groups may be substituted with groups as described in connection with alkyl and loweralkyl above.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. In some embodiments, monocyclic ring systems are exemplified by any 7 membered ring containing 1, 2, 3, or 4 heteroatoms independently selected from oxygen, nitrogen and sulfur. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkenyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, —(CH$_2$)$_m$—NH(CH$_2$)$_m$CH$_3$, —(CH$_2$)$_m$—NH(CH$_2$)$_m$OH alkenylamino, alkynylamino, haloalkylamino, cycloalkylamino, cycloalkylalkylamino, arylamino, arylalkylamino, heterocyclo amino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. In some embodiments, the heterocyclo groups can be substituted with groups as described in connection with alkyl and loweralkyl above. In another embodiment, the term "heterocyclo" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, or S), unless specified otherwise. Examples of heterocyclo groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahydrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, (1S,5R)-8-azabicyclo[3.2.1]oct-2-ene, (1S,4S)-2,5-diazabicyclo[2.2.1]heptane, 7-azabicyclo[2.2.1]heptane and the like. These groups may be substituted with groups as described in connection with alkyl and loweralkyl above.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —$NO_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —$NR_aR_b$, where $R_a$ and $R_b$ are independently selected from the groups hydrogen, alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical $NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)$NR_aR_b$ radical, where $R_a$ and $R_b$ are any suitable substituent such as H, alkyl, cycloalkyl, alkenyl, alkynyl or aryl. In some embodiments, $R_a$ and $R_b$ together with the nitrogen to which they are bonded form a heterocyclic ring.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as amino, alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —$S(O)_2NR_aR_b$ radical, where $R_a$ and $R_b$ are any suitable substituent such as H, alkyl, cycloalkyl, alkenyl, alkynyl or aryl. In some embodiments, $R_a$ and $R_b$ are any suitable substituent such as hydrogen, alkyl, alkenyl, alkynyl, aryl, arylalkyl, cycloalkyl, cycloalkylalkyl, heterocyclo, heterocycloalkyl, heteroaryl, or heteroarylalkyl and each $R_a$ and $R_b$ can be optionally substituted one, two or three times. In some embodiments, $R_a$ and $R_b$ together with the nitrogen to which they are bonded form a heterocyclic ring that can be optionally substituted one, two or three times.

"Urea" as used herein alone or as part of another group refers to an $N(R_c)C(O)NR_aR_b$ radical, where $R_a$, $R_b$ and $R_c$ are any suitable substituent such as H, alkyl, cycloalkyl, alkenyl, alkynyl or aryl. In some embodiments, $R_a$ and $R_b$ together with the nitrogen to which they are bonded form a heterocyclic ring.

"Alkoxyacylamino" as used herein alone or as part of another group refers to an $N(R_a)C(O)OR_b$ radical, where $R_a$, $R_b$ are any suitable substituent such as H, alkyl, cycloalkyl, alkenyl, alkynyl or aryl.

"Aminoacyloxy" as used herein alone or as part of another group refers to an —$OC(O)NR_aR_b$ radical, where $R_a$ and $R_b$ are any suitable substituent such as H, alkyl, cycloalkyl, alkenyl, alkynyl or aryl. In some embodiments, $R_a$ and $R_b$ together with the nitrogen to which they are bonded form a heterocyclic ring.

"Optionally substituted" as used herein refers to the optionally substitution of a chemical moiety. These moieties can be substituted with groups selected from, but not limited to, halo (e.g., haloalkyl), alkyl, haloalkyl, hydroxyalkyl, alkenyl, alkynyl, cycloalkyl (including spiroalkyl, e.g., —$C(CH_2)_{24}$ spiroalkyl), cycloalkylalkyl, aryl, arylalkyl, aryl substituted heteroaryl, heterocyclo, heterocycloalkyl, alkylheterocycloalkyl, heteroaryl, heteroarylalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, —$(CH_2)_m$—$NH(CH_2).CH_3$, —$(CH_2)_m$—NH$(CH_2)_m$OH, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro, polar group or cyano where m=0, 1, 2 or 3. In one embodiment, alkyl or loweralkyl can be substituted with groups selected from a polar group, —$(CH_2)_m$—$N(R^{50})_2$, —$(CH_2)_m$—NH$(CH_2)_mR^{50}$, —$(CH_2)_mNH(CH_2)_{2-3}N(R^{50})_2$, —$S(O)_2OR^{50}$, —CONHNHR$^{50}$, aminosulfonyl —C(CH$_2$)$_2$R$^{50}$ wherein each R$^{50}$ is independently selected from hydrogen, alkyl, alkenyl, alkynyl, aryl, arylalkyl, cycloalkyl, cycloalkylalkyl, heterocyclo, heterocycloalkyl, heteroaryl, or heteroarylalkyl.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, halo, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, N-tert-butoxycarbonyl (or "t-BOC") groups, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates). The polar group can be an ionic group.

"Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc.

"Deuterium" as used herein alone or as part of another group, refers to $^2$H, which has one proton and one neutron in the nucleus. It is a safe, non-radioactive isotope of hydrogen. Any hydrogen in a group or substituent described above may be replaced with deuterium to provide a "deuterated" compound, in some embodiments to modify and/or improve metabolic stability, resulting in better safety, tolerability and/or efficacy.

"Treat" as used herein refers to any type of treatment that imparts a benefit to a patient afflicted with a disease, including improvement in the condition of the patient (e.g., in one or more symptoms), delay in the progression of the disease, delay in onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like.

"Pharmaceutical compositions" are compositions comprising at least one active agent, such as a compound or salt of Formula I, II, or III, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)$_n$—COOH where n is 0-4, and the like. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, and includes, in one embodiment, an excipient that is acceptable for veterinary use as well as human pharmaceutical use. A "pharmaceutically acceptable excipient" as used in the present application includes both one and more than one such excipient.

Compounds of the present invention may optionally be administered in conjunction with other compounds. The other compounds may optionally be administered concurrently. As used herein, the word "concurrently" means sufficiently close in time to produce a combined effect (that is, concurrently may be simultaneously, or it may be two or more events occurring within a short time period before or after each other).

Active compounds of the present invention may optionally be administered in conjunction with other compounds useful in the treatment of blood clot formation in a subject in need thereof (e.g., a subject afflicted with coronary artery disease, peripheral vascular disease, or cerebrovascular disease, or prior to any medical or surgical procedure in which diminished coagulation potential is desirable, a non-limiting example of which is pulmonary vein ablation).

The present invention is primarily focused on the treatment of a human subject or host, but the invention may be used to treat animals, such as mammalian subjects such as mice, rats, dogs, cats, livestock and horses for veterinary purposes, and for drug screening and drug development purposes. Subjects may be of any age, including infant, juvenile, adolescent, adult, and geriatric subjects.

2. Detailed Description of Active Compounds

It has been discovered that a compound of Formula I as described herein is a superior inhibitor of the Mer tyrosine kinase. Surprisingly, substituents at the $R^7$ and $R^8$ positions of a compound of Formula I as described herein play a significant role in a compound's ability to inhibit MerTK and improve the selectivity index for inhibition of MerTK over Flt3 and Axl. In one embodiment, $R^7$ is alkyl. In one embodiment, $R^7$ is methyl. In another embodiment, $R^7$ is ethyl.

It has also been discovered that the stereochemistry of the carbon attached to the $R^7$ and $R^8$ substituents plays an important role in a compound's ability to inhibit MerTK and improve the selectivity index for inhibition of MerTK over Flt3 and Axl. In one embodiment, the carbon attached to the $R^7$ and $R^8$ substituents is in the S configuration. In one embodiment, the carbon attached to the $R^7$ and $R^8$ substituents is in the R configuration.

As noted above, the present invention provides active compounds of Formula I:

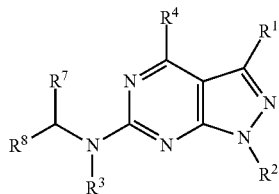

(I)

wherein:

$R^1$ is aryl such as phenyl (in some embodiments substituted 1, 2 or 3 times with heterocycloalkylalkyl, which heterocycloalkylalkyl is substituted or unsubstituted, for example substituted from 1 to 3 times with halo, or alkyl). In some embodiments, heterocycloalkylalkyl is a substituent of the formula —R'R", where R' is substituted or unsubstituted $C_1$-$C_2$ alkyl, and R" is a heterocyclo group, such as an optionally substituted piperazine or morpholine group.

$R^2$ is —$R^5R^6$, where $R^5$ is a covalent bond or $C_1$ to $C_3$ alkyl and $R^6$ is cycloalkyl, heterocycloalkyl, aryl, heteroaryl or alkyl, and wherein $R^6$ is optionally substituted from one to two times with independently selected polar groups from the group consisting of halo, hydroxy, alkoxy, carboxy, nitro, cyano; secondary and tertiary amino; amido, ureido, sulfonamido, sulfinyl, sulfhydryl, silyl, S-sulfonamido, N-sulfonamido, C-carboxy, O-carboxy, C-amido, N-amido, sulfonyl, N-tert-butoxycarbonyl, phosphono, morpholino, piperazinyl, tetrazolo, alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates) and the polar group can be an ionic group, for example, an anionic or cationic group, including but not limited to carboxylate, sulfonate, phosphate, N-oxide, quaternized heterocyclic amine, for example, imidazolium and pyridinium; uronic acids, carboxylic acid, sulfonic acid, guanidinium, phosphoric acid, phosphonic acid, phosphatidyl choline, phosphonium, borate, and sulfate;

$R^3$ is H, alkyl, arylalkyl, cycloalkylalkyl, heterocycloalkylalkyl, heteroarylalkyl, or alkoxyalkyl, each of which is optionally substituted one, two or three times with independently selected polar groups (typically $R^3$ is H);

$R^4$ is H, loweralkyl, halo, or loweralkoxy;

$R^7$ is alkyl, arylalkyl, cycloalkylalkyl, heterocycloalkylalkyl, heteroarylalkyl, or alkoxyalkyl, each of which is optionally substituted one, two or three times with independently selected polar groups (in some embodiments $R^7$ is typically methyl, ethyl, propyl, fluoromethyl, difluoromethyl, fluoroethyl, difluoroethyl, hydroxymethyl, hydroxyethyl, $CD_2H$, $CDH_2$, $CF_3$, $CD_3$, etc.);

$R^8$ is alkyl, arylalkyl, cycloalkylalkyl, heterocycloalkylalkyl, heteroarylalkyl, or alkoxyalkyl, preferably alkyl or cycloalkyl, each of which is optionally substituted one, two or three times with independently selected polar groups (e.g., halo such as fluoro; hydroxyl, etc.);

or a pharmaceutically acceptable salt or prodrug thereof.

In some embodiments of the foregoing, the compounds have the structure of Formula I':

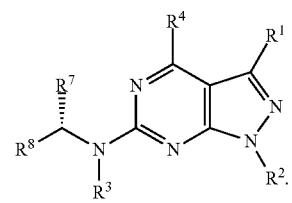

(I')

In other embodiments of the foregoing, the compounds have the structure of Formula I":

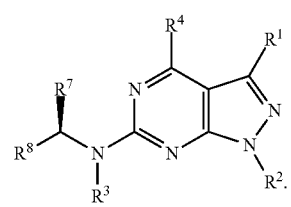

(I")

In some embodiments of the foregoing, $R^1$ is phenyl or pyridyl, which phenyl or pyridyl is unsubstituted or substituted from 1 to 3 times with halo, amino, nitro, alkyl, alkoxyl, haloalkyl, —$(CH_2)_m$—$NH(CH_2)_m$OH, cycloalkyl, heterocycloalkylalkyl, aryl, or heteroaryl, where m is 0, 1, 2, or 3.

In some embodiments of the foregoing $R^5$ is —$CH_2$—.

In some embodiments of the foregoing, $R^8$ is $C_1$-$C_8$ alkyl, $C_3$-$C_8$ cycloalkyl, $C_3$-$C_8$ cycloalkylalkyl, or $C_1$-$C_8$ alkyl aryl.

In some embodiments of the foregoing, $R^6$ is cyclohexyl.

In some embodiments of the foregoing, $R^6$ is substituted once with amino or hydroxy.

In some embodiments of the foregoing, $R^4$ is H.

It has been discovered that a compound of Formula II as described herein is a superior inhibitor of the Mer tyrosine kinase. Surprisingly, substituents at the $R^{17}$ and $R^{18}$ positions of a compound of Formula I as described herein play a significant role in a compound's ability to inhibit MerTK and improve the selectivity index for inhibition of MerTK over Flt3 and Axl. In one embodiment, $R^{17}$ is alkyl. In one embodiment, $R^{17}$ is methyl. In another embodiment, $R^{17}$ is ethyl.

It has also been discovered that the stereochemistry of the carbon attached to the $R^{17}$ and $R^{18}$ substituents plays an important role in a compound's ability to inhibit MerTK and improve the selectivity index for inhibition of MerTK over Flt3 and Axl. In one embodiment, the carbon attached to the $R^{17}$ and $R^{18}$ substituents is in the S configuration. In one embodiment, the carbon attached to the $R^{17}$ and $R^{18}$ substituents is in the R configuration.

In another aspect of the invention, the present invention provides active compounds of Formula II:

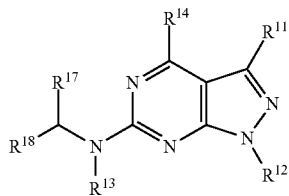

II wherein:

$R^{11}$ is —$R^9(R^{10})_n$, where $R^9$ is alkyl, alkenyl, -alkylaryl, heterocyclo, aryl, heteroaryl and $R^{10}$ is hydrogen, alkyl, haloalkyl, alkoxyalkyl, —O-alkylaryl, hydroxyalkyl, alkenyl, alkenyloxy, alkynyl, alkynyloxy, cycloalkyl, cycloalkylalkyl, cycloalkoxy, cycloalkylalkyloxy, heterocyclo, heterocycloalkyl, alkylheterocycloalkyl, heterocyclooxy, heterocyclolalkyloxy, aryl, arylalkyl, aryloxy, arylalkyloxy, heteroaryl, alkylheteroaryl, halo, hydroxyl, alkoxy, haloalkoxy, mercapto, alkyl-S(O)$_m$—, haloalkyl-S(O)$_m$—, alkenyl-S(O)$_m$—, alkynyl-S(O)$_m$—, cycloalkyl-S(O)$_m$—, cycloalkylalkyl-S(O)$_m$—, aryl-S(O)$_m$—, arylalkyl-S(O)$_m$—, heterocyclo-S(O)$_m$—, heterocycloalkyl-S(O)$_m$—, amino, carboxy, alkylamino, —(CH$_2$)$_m$—NHalkyl, —(CH$_2$)$_m$—N(alkyl)$_2$, —(CH$_2$)$_m$—NH(CH$_2$)$_m$OH, —(CH$_2$)$_m$—NH(CH$_2$)$_m$cycloalkyl, —(CH$_2$)$_m$—NH(CH$_2$)$_{2-3}$heterocyclo, —(CH$_2$)$_m$—NH(CH$_2$)$_m$aryl, —(CH$_2$)$_m$—NH(CH$_2$)$_{2-3}$heteroaryl, —(CH$_2$)$_m$NH(CH$_2$)$_{2-3}$N(alkyl)$_2$, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, S(O)$_2$OR$^{19}$, —CONHNH$_2$, cyano, nitro, aminosulfonyl, COOH, sulfonamide, urea, alkoxyacylamino, aminoacyloxy, —C(CH$_2$)$_2$R$^{19}$, and wherein R$^{10}$ is optionally substituted one two or three times;

m=0, 1, 2 or 3;

n=0, 1 or 2;

$R^{12}$ is —$R^{15}R^{16}$, where $R^{15}$ is a covalent bond or $C_1$ to $C_3$ alkyl and $R^{16}$ is cycloalkyl, heterocycloalkyl, aryl, heteroaryl or alkyl, and wherein $R^{16}$ is optionally substituted one, two or three times from the group consisting of halo, hydroxy, alkoxy, carboxy, nitro, cyano; secondary and tertiary amino; amido, ureido, sulfonamido, sulfinyl, sulfhydryl, silyl, S-sulfonamido, N-sulfonamido, C-carboxy, O-carboxy, C-amido, N-amido, sulfonyl, N-tert-butoxycarbonyl, phosphono, morpholino, piperazinyl, tetrazolo, alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates) and the polar group can be an ionic group, for example, an anionic or cationic group, including but not limited to carboxylate, sulfonate, phosphate, N-oxide, quaternized heterocyclic amine, for example, imidazolium and pyridinium; uronic acids, carboxylic acid, sulfonic acid, guanidinium, phosphoric acid, phosphonic acid, phosphatidyl choline, phosphonium, borate, and sulfate;

$R^{13}$ is selected from the group consisting of hydrogen, deuterium, alkyl, alkenyl, alkynyl, aryl, arylalkyl, cycloalkyl, cycloalkylalkyl, heterocyclo, heterocycloalkyl, alkylheterocycloalkyl, heteroaryl, heteroarylalkyl, and alkoxyalkyl, each of which is optionally substituted one, two or three times (typically $R^{13}$ is H);

$R^{14}$ is H, loweralkyl, halo, or loweralkoxy;

$R^{17}$ is alkyl, haloalkyl, hydroxyalkyl, alkenyl, alkynyl, aryl, arylalkyl, cycloalkyl, cycloalkylalkyl, alkylheterocycloalkyl, heterocyclo, heterocycloalkyl, heteroaryl, heteroarylalkyl, and alkoxyalkyl, each of which is optionally substituted one, two or three times (in some embodiments $R^{17}$ is typically methyl, ethyl, propyl, fluoromethyl, difluoromethyl, trifluoromethyl, fluoroethyl, difluoroethyl, hydroxymethyl, hydroxyethyl, CD$_2$H, CDH$_2$, CF$_3$, CD$_3$, etc.);

$R^{18}$ is alkyl, haloalkyl, hydroxyalkyl, alkenyl, alkynyl, aryl, arylalkyl; cycloalkyl, cycloalkylalkyl, alkylheterocycloalkyl, heterocyclo, heterocycloalkyl, heteroaryl, heteroarylalkyl, and alkoxyalkyl, typically alkyl or cycloalkyl, each of which is optionally substituted one, two or three times;

$R^{17}$ and $R^{18}$ can form a cycloalkyl group that can be optionally substituted one; two or three times;

$R^{19}$ is selected from hydrogen, alkyl, alkenyl, alkynyl, aryl, arylalkyl, cycloalkyl, cycloalkylalkyl, heterocyclo, heterocycloalkyl, heteroaryl, or heteroarylalkyl;

or a pharmaceutically acceptable composition, salt, isotopic analog, or prodrug thereof.

In another aspect of the invention, the present invention provides active compounds of Formula IIa:

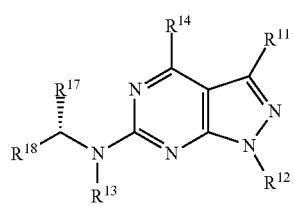

IIa wherein:

$R^{11}$, $R^{12}$, $R^{13}$, $R^{14}$, $R^{17}$ and $R^{18}$ are as defined herein.

In another aspect of the invention, the present invention provides active compounds of Formula IIc:

IIb wherein:
$R^{11}$, $R^{12}$, $R^{13}$, $R^{14}$, $R^{17}$ and $R^{18}$ are as defined herein.

In another aspect of the invention, the present invention provides active compounds of Formula IIc:

IIc

In another aspect of the invention, the present invention provides active compounds of Formula IId:

IId wherein:
$R^{11}$, $R^{12}$, $R^{13}$, $R^{14}$ and $R^{18}$ are as defined herein.

In another aspect of the invention, the present invention provides active compounds of Formula IIe:

IIe wherein:
$R^{11}$, $R^{12}$, $R^{13}$, $R^{14}$, and $R^{18}$ are as defined herein.

In another aspect of the invention, the present invention provides active compounds of Formula III:

IIf wherein:
$R^{11}$, $R^{12}$, $R^{13}$, $R^{14}$ and $R^{18}$ are as defined herein.

In another aspect of the invention, the present invention provides active compounds of Formula IIg:

IIg wherein:
$R^{11}$, $R^{12}$, $R^{13}$, $R^{14}$ and $R^{18}$ are as defined herein.

In another aspect of the invention, the present invention provides active compounds of Formula IIh:

IIh wherein:
$R^{11}$, $R^{12}$, $R^{13}$, $R^{14}$, and $R^{18}$ are as defined herein.

In some embodiments, structures are provided including Formulas II, IIa, and IIb, wherein $R^{17}$ is alkyl, $R^{18}$ is alkyl, $R^{12}$ is cycloalkyl, $R^{11}$ is aryl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is alkyl, $R^{12}$ is cyclohexyl, is aryl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is alkyl, $R^{12}$ is para-hydroxy cyclohexyl, $R^{11}$ is aryl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is alkyl, $R^{12}$ is cycloalkyl, $R^{11}$ is heteroaryl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is alkyl, $R^{12}$ is cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is alkyl, $R^{12}$ is para-hydroxy cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas II, IIa, and wherein $R^{17}$ is alkyl, $R^{18}$ is alkyl, $R^{12}$ is cycloalkyl, $R^{11}$ is phenyl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is alkyl, $R^{12}$ is cyclohexyl, $R^{11}$ is phenyl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is alkyl, $R^{12}$ is para-hydroxy cyclohexyl, $R^{11}$ is phenyl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is cycloalkylalkyl, $R^{12}$ is cycloalkyl, $R^{11}$ is aryl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is cycloalkylalkyl, $R^{12}$ is cyclohexyl, $R^{11}$ is aryl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is cycloalkylalkyl, $R^{12}$ is para-hydroxy cyclohexyl, $R^{11}$ is aryl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is cycloalkylalkyl, $R^{12}$ is cycloalkyl, $R^{11}$ is heteroaryl, and $R^{13}$, $R^{14}$, and $R^{15}$ are H or loweralkyl, any of which can be optionally substituted.

In some embodiments, structures are provided including Formulas II, IIa, and wherein $R^{17}$ is alkyl, $R^{18}$ is cycloalkylalkyl, $R^{12}$ is cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas II, IIa, and wherein $R^{17}$ is alkyl, $R^{18}$ is cycloalkylalkyl, $R^{12}$ is para-hydroxy cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is cycloalkylalkyl, $R^{12}$ is cycloalkyl, $R^{11}$ is phenyl, and $R^{13}$, $R^{14}$, and $R^{15}$ are H or loweralkyl, any of which can be optionally substituted.

In some embodiments, structures are provided including Formulas II, IIa, and wherein $R^{17}$ is alkyl, $R^{18}$ is cycloalkylalkyl, $R^{12}$ is cyclohexyl, $R^{11}$ is phenyl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is alkyl, $R^{18}$ is cycloalkylalkyl, $R^{12}$ is para-hydroxy cyclohexyl, $R^{11}$ is phenyl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is methyl, $R^{18}$ is propyl, $R^{12}$ is cycloalkyl, $R^{11}$ is aryl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is methyl, $R^{18}$ is propyl, $R^{12}$ is cyclohexyl, $R^{11}$ is aryl, and $R^{13}$, $R^{14}$, and $R^{15}$ are H or loweralkyl, any of which can be optionally substituted.

In some embodiments, structures are provided including Formulas II, IIa, and wherein $R^{17}$ is methyl, $R^{18}$ is propyl, $R^{12}$ is para-hydroxy cyclohexyl, $R^{11}$ is aryl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is methyl, $R^{18}$ is propyl, $R^{12}$ is cycloalkyl, is heteroaryl, and $R^{13}$, $R^{14}$, and $R'5$ are H or loweralkyl, any of which can be optionally substituted.

In some embodiments, structures are provided including Formulas II, IIa, and IIb, wherein $R^{17}$ is methyl, $R^{18}$ is propyl, $R^{12}$ is cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is methyl, $R^{18}$ is propyl, $R^{12}$ is para-hydroxy cyclohexyl, $R^{11}$ is heteroaryl, and $R^{13}$, le, and $R^{15}$ are H or loweralkyl, any of which can be optionally substituted.

In some embodiments, structures are provided including Formulas II, IIa, and wherein $R^{17}$ is methyl, $R^{18}$ is propyl, $R^{12}$ is cycloalkyl, $R^{11}$ is phenyl, and $R^{13}$, $R^{14}$, and $R^{15}$ are H or loweralkyl, any of which can be optionally substituted.

In some embodiments, structures are provided including Formulas II, IIa, and wherein $R^{17}$ is methyl, $R^{18}$ is propyl, $R^{12}$ is cyclohexyl, $R^{11}$ is phenyl, and $R^{13}$, $R^{14}$, and $R^{15}$ are H or loweralkyl, any of which can be optionally substituted.

In some embodiments, structures are provided including Formulas II, IIa, and IIb, wherein $R^{17}$ is methyl, $R^{18}$ is propyl, $R^{12}$ is para-hydroxy cyclohexyl, $R^{11}$ is phenyl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is alkyl, $R^{12}$ is cycloalkyl, $R^{11}$ is aryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is alkyl, $R^{12}$ is cyclohexyl, $R^{11}$ is aryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is alkyl, $R^{12}$ is para-hydroxy cyclohexyl, $R^{11}$ is aryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is alkyl, $R^{12}$ is cycloalkyl, $R^{11}$ is heteroaryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is alkyl, $R^{12}$ is cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is alkyl, $R^{12}$ is para-hydroxy cyclohexyl, $R^{11}$ is heteroaryl, and $R^3$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is alkyl, $R^{12}$ is cycloalkyl, $R^{11}$ is phenyl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is alkyl, $R^{12}$ is cyclohexyl, $R^{11}$ is phenyl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is alkyl, $R^{12}$ is para-hydroxy cyclohexyl, $R^{11}$ is phenyl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is cycloalkylalkyl, $R^{12}$ is cycloalkyl, $R^{11}$ is aryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is cycloalkylalkyl, $R^{12}$ is cyclohexyl, $R^{11}$ is aryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is cycloalkylalkyl, $R^{12}$ is para-hydroxy cyclohexyl, $R^{11}$ is aryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is cycloalkylalkyl, $R^{12}$ is cycloalkyl, $R^{11}$ is heteroaryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is cycloalkylalkyl, $R^{12}$ is cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is cycloalkylalkyl, $R^{12}$ is para-hydroxy cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is cycloalkylalkyl, $R^{12}$ is cycloalkyl, $R^{11}$ is phenyl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is cycloalkylalkyl, $R^{12}$ is cyclohexyl, $R^{11}$ is phenyl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is cycloalkylalkyl, $R^{12}$ is para-hydroxy cyclohexyl, $R^{11}$ is phenyl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is propyl, $R^{12}$ is cycloalkyl, $R^{11}$ is aryl, and $R^{13}$, $R^{14}$, and $R^5$ are H or loweralkyl, any of which can be optionally substituted.

In some embodiments, structures are provided including Formulas IIc, IId, IIe, IIf, IIg, and IIh, wherein $R^{18}$ is propyl, $R^{12}$ is cyclohexyl, $R^{11}$ is aryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is propyl, $R^{12}$ is para-hydroxy cyclohexyl, $R^{11}$ is aryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is propyl, $R^{12}$ is cycloalkyl, $R^{11}$ is heteroaryl, and $R^3$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is propyl, $R^{12}$ is cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is propyl, $R^{12}$ is para-hydroxy cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is propyl, $R^{12}$ is cycloalkyl, $R^{11}$ is phenyl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is propyl, $R^{12}$ is cyclohexyl, $R^{11}$ is phenyl, and $R^{13}$, $R^{14}$, and $R^{15}$ are H or loweralkyl, any of which can be optionally substituted.

In some embodiments, structures are provided including Formulas IIc, IId, IIe, IIf, IIg, and IIh, wherein $R^{18}$ is propyl, $R^{12}$ is para-hydroxy cyclohexyl, $R^{11}$ is phenyl, and $R^{13}$, $R^{14}$, and $R^{15}$ are H or loweralkyl, any of which can be optionally substituted.

It has also been discovered that the substituents at the $R^{20}$ and $R^{21}$ positions of active compounds as described herein play a role in a compound's ability to inhibit MerTK and Tyro3 tyrosine kinases, and improve the selectivity index for inhibition of Tyro3 over MerTK. In one embodiment, $R^{20}$ is alkyl. In one embodiment, $R^{20}$ is ethyl.

It has also been discovered that the stereochemistry of the carbon attached to the $R^{20}$ and $R^{21}$ substituents plays a role in a compound's ability to inhibit MerTK and Tyro3 tyrosine kinases, and improve the selectivity index for inhibition of Tyro3 over MerTK. In one embodiment, the carbon attached to the $R^{20}$ and $R^{21}$ substituents is in the S configuration. In one embodiment, the carbon attached to the $R^{20}$ and $R^{21}$ substituents is in the R configuration.

In another aspect of the invention, the present invention provides active compounds of Formula III:

III wherein:

$R^{20}$ is alkyl, haloalkyl, hydroxyalkyl, arylalkyl, cycloalkylalkyl, alkylheterocycloalkyl, heteroarylalkyl, and alkoxyalkyl, each of which is optionally substituted (in some embodiments $R^{20}$ is typically methyl, ethyl, propyl, fluoromethyl, difluoromethyl, fluoroethyl, difluoroethyl, hydroxymethyl, hydroxyethyl, $CD_2H$, $CDH_2$, $CF_3$, $CD_3$, etc.);

$R^{21}$ is alkyl, haloalkyl, hydroxyalkyl, alkenyl, alkynyl, aryl, arylalkyl, cycloalkyl, cycloalkylalkyl, alkylheterocycloalkyl, heterocyclo, heterocycloalkyl, heteroaryl, heteroarylalkyl, and alkoxyalkyl, typically alkyl or cycloalkyl, each of which is optionally substituted one, two or three times;

$R^{11}$, $R^{12}$, $R^{13}$ and $R^{14}$ are as defined above.

In another aspect of the invention, the present invention provides active compounds of Formula IIIa:

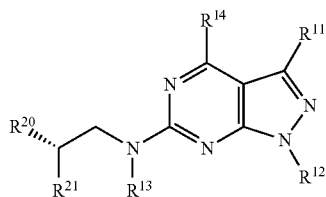

wherein:
$R^{11}$, $R^{12}$, $R^{13}$, $R^{14}$, $R^{20}$ and $R^{21}$ are as defined above.

In another aspect of the invention, the present invention provides active compounds of Formula IIIb:

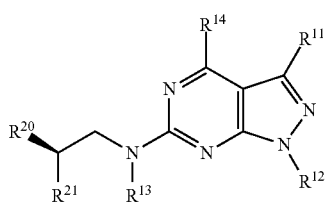

wherein:
$R^{11}$, $R^{12}$, $R^{13}$, $R^{14}$, $R^{20}$ and $R^{21}$ are as defined above.

In another aspect of the invention, the present invention provides active compounds of Formula IIIc:

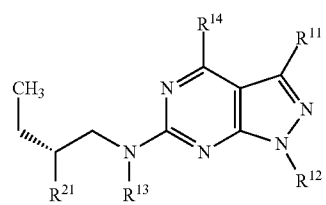

wherein:
$R^{11}$, $R^{12}$, $R^{13}$, $R^{14}$ and $R^{21}$ are as defined above.

In another aspect of the invention, the present invention provides active compounds of Formula IIId:

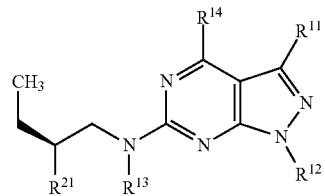

wherein:
$R^{11}$, $R^{12}$, $R^{13}$, $R^{14}$ and $R^{21}$ are as defined above.

In another aspect of the invention, the present invention provides active compounds of Formula IIIe:

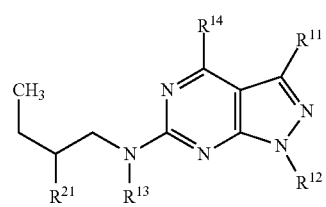

wherein:
$R^{11}$, $R^{12}$, $R^{13}$, $R^{14}$ and $R^{21}$ are as defined above.

In some embodiments, structures are provided including Formulas III, IIIa, and IIIb wherein $R^{20}$ is alkyl, $R^{21}$ is alkyl, $R^{12}$ is cycloalkyl, $R^{11}$ is aryl, and $R^{13}$, $R^{14}$, and $R^{is}$ are H or loweralkyl, any of which can be optionally substituted.

In some embodiments, structures are provided including Formulas III, IIIa, and IIIb wherein $R^{20}$ is alkyl, $R^{21}$ is alkyl, $R^{12}$ is cyclohexyl, $R^{11}$ is aryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is alkyl, $R^{12}$ is para-hydroxy cyclohexyl, $R^{11}$ is aryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is alkyl, $R^{12}$ is cycloalkyl, $R^{11}$ is heteroaryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is alkyl, $R^{12}$ is cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is alkyl, $R^{12}$ is para-hydroxy cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is alkyl, $R^{12}$ is cycloalkyl, $R^{11}$ is phenyl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is alkyl, $R^{12}$ is cyclohexyl, $R^{11}$ is phenyl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is alkyl, $R^{12}$ is para-hydroxy cyclohexyl, $R^{11}$ is phenyl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is cycloalkylalkyl, $R^{12}$ is cycloalkyl, $R^{11}$ is aryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is cycloalkylalkyl, $R^{12}$ is cyclohexyl, $R^{11}$ is aryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is cycloalkylalkyl, $R^{12}$ is para-hydroxy cyclohexyl, $R^{11}$ is aryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is cycloalkylalkyl, $R^{12}$ is cycloalkyl, $R^{11}$ is heteroaryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is cycloalkylalkyl, $R^{12}$ is cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is cycloalkylalkyl, $R^{12}$ is para-hydroxy cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is cycloalkylalkyl, $R^{12}$ is cycloalkyl, $R^{11}$ is phenyl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is cycloalkylalkyl, $R^{12}$ is cyclohexyl, $R^{11}$ is phenyl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is alkyl, $R^{21}$ is cycloalkylalkyl, $R^{12}$ is para-hydroxy cyclohexyl, $R^{11}$ is phenyl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is methyl, $R^{21}$ is propyl, $R^{12}$ is cycloalkyl, $R^{11}$ is aryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is methyl, $R^{21}$ is propyl, $R^{12}$ is cyclohexyl, $R^{11}$ is aryl, and $R^{13}$, $R^{14}$, and $R^5$ are H or loweralkyl, any of which can be optionally substituted.

In some embodiments, structures are provided including Formulas III, IIIa, and IIIb wherein $R^{20}$ is methyl, $R^{21}$ is propyl, $R^{12}$ is para-hydroxy cyclohexyl, $R^{11}$ is aryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is methyl, $R^{21}$ is propyl, $R^{12}$ is cycloalkyl, $R^{11}$ is heteroaryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is methyl, $R^{21}$ is propyl, $R^{12}$ is cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is methyl, $R^{21}$ is propyl, $R^{12}$ is para-hydroxy cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is methyl, $R^{21}$ is propyl, $R^{12}$ is cycloalkyl, $R^{11}$ is phenyl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is methyl, $R^{21}$ is propyl, $R^{12}$ is cyclohexyl, $R^{11}$ is phenyl, and $R^{13}$, $R^{14}$, and $R^{15}$ are H or loweralkyl, any of which can be optionally substituted.

In some embodiments, structures are provided including Formulas III, IIIa, and IIIb wherein $R^{20}$ is methyl, $R^{21}$ is propyl, $R^{12}$ is para-hydroxy cyclohexyl, $R^{11}$ is phenyl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is alkyl, $R^{12}$ is cycloalkyl, $R^{11}$ is aryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is alkyl, $R^{12}$ is cyclohexyl, $R^{11}$ is aryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is alkyl, $R^{12}$ is para-hydroxy cyclohexyl, $R^{11}$ is aryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is alkyl, $R^{12}$ is cycloalkyl, $R^{11}$ is heteroaryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is alkyl, $R^{12}$ is cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is alkyl, $R^{12}$ is para-hydroxy cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is alkyl, $R^{12}$ is cycloalkyl, $R^{11}$ is phenyl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is alkyl, $R^{12}$ is cyclohexyl, $R^{11}$ is phenyl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is alkyl, $R^{12}$ is para-hydroxy cyclohexyl, $R^{11}$ is phenyl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is cycloalkylalkyl, $R^{12}$ is cycloalkyl, $R^{11}$ is aryl, and $R^{13}$, $R^{14}$, and $R^5$ are H or loweralkyl, any of which can be optionally substituted.

In some embodiments, structures are provided including Formulas IIIc, IIId, and IIIe, wherein $R^{21}$ is cycloalkylalkyl, $R^{12}$ is cyclohexyl, $R^{11}$ is aryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is cycloalkylalkyl, $R^{12}$ is para-hydroxy cyclohexyl, $R^{11}$ is aryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is cycloalkylalkyl, $R^{12}$ is cycloalkyl, $R^{11}$ is heteroaryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is cycloalkylalkyl, $R^{12}$ is cyclohexyl, $R^{11}$ is heteroaryl, and $R^{13}$, $R^{14}$, and $R^5$ are H or loweralkyl, any of which can be optionally substituted.

In some embodiments, structures are provided including Formulas IIIc, IIId, and IIIe, wherein $R^{21}$ is cycloalkylalkyl, $R^{12}$ is para-hydroxy cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is cycloalkylalkyl, $R^{12}$ is cycloalkyl, $R^{11}$ is phenyl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is cycloalkylalkyl, $R^{12}$ is cyclohexyl, $R^{11}$ is phenyl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is cycloalkylalkyl, $R^{12}$ is para-hydroxy cyclohexyl, $R^{11}$ is phenyl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is propyl, $R^{12}$ is cycloalkyl, $R^{11}$ is aryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is propyl, $R^{12}$ is cyclohexyl, $R^{11}$ is aryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is propyl, $R^{12}$ is para-hydroxy cyclohexyl, $R^{11}$ is aryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is propyl, $R^{12}$ is cycloalkyl, $R^{11}$ is heteroaryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is propyl, $R^{12}$ is cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is propyl, $R^{12}$ is para-hydroxy cyclohexyl, $R^{11}$ is heteroaryl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is propyl, $R^{12}$ is cycloalkyl, $R^{11}$ is phenyl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is propyl, $R^{12}$ is cyclohexyl, $R^{11}$ is phenyl, and $R^{13}$, $R^{14}$, and $R^{15}$ are H or loweralkyl, any of which can be optionally substituted.

In some embodiments, structures are provided including Formulas IIIc, IIId, and IIIe, wherein $R^{21}$ is propyl, $R^{12}$ is para-hydroxy cyclohexyl, $R^{11}$ is phenyl, and $R^{13}$, $R^{14}$, and $R^{15}$ are H or loweralkyl, any of which can be optionally substituted.

Active compounds may be provided as pharmaceutically acceptable prodrugs, which are those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are transformed, sometimes rapidly in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

The active compounds disclosed herein can, as noted above, be provided in the form of their pharmaceutically acceptable salts. Pharmaceutically acceptable salts are salts that retain the desired biological activity of the parent compound and do not impart undesired toxicological effects. Nonlimiting examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Active compounds as described herein can be prepared in accordance with known procedures, or variations thereof that will be apparent to those skilled in the art.

3. Pharmaceutical Compositions and Dosages for all Indications

The active compounds described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy comprising admixing the components, optionally including one or more accessory ingredients.

In one aspect, the invention provides a pharmaceutical composition comprising a pharmaceutically effective amount of an active compound as described herein and a pharmaceutically acceptable carrier.

The compounds provided herein are administered for medical therapy in a therapeutically effective amount. The amount of the compounds administered will typically be determined by a physician, in the light of the relevant circumstances, including the condition to be treated, the chosen route of administration, the compound administered, the age, weight, and response of the individual patient, the severity of the patient's symptoms, and the like.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces), transdermal administration, and intraventricular injection (injection into a ventricle of the brain, e.g., by an implanted catheter or Ommaya reservoir, such as in the case of morbid obesity), ocular (via injection, implantation or by reservoir), and intranasal, although the most suitable route in any given case will depend on the nature and severity of the condition being treated and on the nature of the particular active compound which is being used.

The compositions for oral administration can take the form of bulk liquid solutions or suspensions, or bulk powders. Typically, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (as a nonlimiting example, from about 0.1 to about 50% by weight or preferably from about 1 to about 40% by weight) with the remainder being various vehicles or carriers and processing aids helpful for forming the desired dosing form. In one embodiment, the compound is present from about 1% to about 10% by weight.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. In one embodiment, the compounds are administered in a controlled release formulation.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Injectable compositions are typically based upon injectable sterile saline or phosphate-buffered saline or other injectable carriers known in the art.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidylcholines, and lecithin.

In addition to compounds of Formula I, II, or III, or other active compounds described herein, or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

The Mer TKI compound of this invention can also be administered in sustained release forms or from sustained release drug delivery systems. A description of representative sustained release materials can be found in Remington's Pharmaceutical Sciences.

In certain embodiments, the formulation comprises water. In another embodiment, the formulation comprises a cyclodextrin derivative. In certain embodiments, the formulation comprises hexapropyl-β-cyclodextrin. In a more particular embodiment, the formulation comprises hexapropyl-β-cyclodextrin (10-50% in water).

The present invention also includes pharmaceutically acceptable acid addition salts of compounds of the compounds of the invention. The acids which are used to prepare the pharmaceutically acceptable salts are those which form non-toxic acid addition salts, i.e. salts containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The above-described components for pharmaceutical compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. The duration of the treatment can be once per day for a period of two to three weeks or until the condition is essentially controlled.

The therapeutically effective dosage of any active compound described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound, including the cases where a salt is employed. In some embodiments, the dosage can be the amount of compound needed to provide a serum concentration of the active compound of up to between about 1 and 5, 10, 20, 30, or 40 µM. In some embodiments, a dosage from about 10 mg/kg to about 50 mg/kg can be employed for oral administration. Typically, a dosage from about 0.5 mg/kg to 5 mg/kg can be employed for intramuscular injection. In some embodiments, dosages can be from about 1 µmol/kg to about 50 µmol/kg, or, optionally, between about 22 µmol/kg and about 33 µmol/kg of the compound for intravenous or oral administration. An oral dosage form can include any appropriate amount of active material, including for example from 5 mg to, 50, 100, 200, or 500 mg per tablet or other solid dosage form.

Active compounds may be administered as pharmaceutically acceptable prodrugs, which are those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

In one aspect of the invention, a method is provided to treat a host by administering a daily amount of a Mer TKI including active compounds of the present invention, which may be provided in dosages once or more a day. In one embodiment, the Mer TKI dose is between about 0.5 mg and about 200 mg. In one embodiment, the dose is at least about 1 mg, about 2 mg, about 3 mg, about 4 mg, about 5 mg, about 10 mg, about 12 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 125 mg, about 140 mg, about 150, about 175, or about 200 mg. In another embodiment, the dose is between about 200 mg and 1250 mg. In one embodiment, the dose is about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg or more.

In one embodiment, the compounds described herein are combined with an additional anti-tumor agent, anti-neoplastic agent, anti-cancer agent, immunomodulatory agent, immunostimulatory agent, anti-infective agents, anti-thrombotic, and/or anti-clotting agent. The dosage administered to the host can be similar to that as administered during monotherapy treatment, or may be lower, for example, between about 0.5 mg and about 150 mg. In one embodiment, the dose is at least about 1 mg, about 2 mg, about 3 mg, about 4 mg, about 5 mg, about 10 mg, about 12 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 125 mg, about 140 mg, or about 150 mg.

In one embodiment, for the case of the co-administration of an active compound in combination with an additional anti-tumor agent, anti-neoplastic agent, anti-cancer agent, immunomodulatory agent, immunostimulatory agent, anti-infective agents, anti-thrombotic, and/or anti-clotting agent, as otherwise described herein, the amount of the compound according to the present invention to be administered ranges from about 0.01 mg/kg of the patient to about 50 mg/kg or more of the patient or considerably more, depending upon the second compound to be co-administered, the condition of the patient, severity of the disease to be treated, and the route of administration. In one embodiment, the additional anti-tumor agent, anti-neoplastic agent, anti-cancer agent, immunomodulatory agent, immunostimulatory agent, anti-infective agents, anti-thrombotic, and/or anti-clotting agent may, for example, be administered in amounts ranging from about 0.01 mg/kg to about 500 mg/kg. In one embodiment, for oral dosing, suitable daily dosages are, for example, between about 0.1-4000 mg administered orally once-daily, twice-daily, or three times-daily, continuous (every day) or intermittently (e.g., 3-5 days a week).

Methods of Use of the Active Compounds

4. Anti-Tumor Agents, Including Anti-Cancer Agents

In one aspect of the invention, a compound of Formula I, II, or III, or other active compound as described herein, is capable of direct anti-cancer effects by inhibiting Mer tyrosine kinase within tumor cells. In one embodiment, the cancer treated overexpresses MerTK. In one embodiment, the cancer which overexpresses MerTK is selected from the group consisting of acute myeloid leukemia, T-cell acute lymphoid leukemia, B-cell acute lymphoid leukemia, lung cancer, glioma, melanoma, prostate cancer, schwannoma, mantle cell lymphoma, and rhabdomyosarcoma. In an alternative embodiment, the cancer ectopically expresses MerTK. In one embodiment, the compound administered is UNC4214A.

In one embodiment, the cancer treated has a mutation in the amino acid sequence of the MerTK extracellular or transmembrane domain selected from P40S (melanoma), S159F (lung), E204K (urinary tract) S428G (gastric), I431F (lung), A446G (kidney), N454S (liver), W485S/C (lymphoma), and V486I (melanoma). In one embodiment the cancer treated has a mutation in the amino acid sequence of the MerTK cytosolic domain mutation selected from L586F (urinary tract), G594R (breast), S626C (urinary tract), P672S (lung), L688M (colon), A708S (head and neck), N718Y (lung), R722stop (colon), M790V (lung), P802S (melanoma), V873I (liver), S905F (lung), K923R (melanoma), P958L (kidney), D983N (liver), and D990N (colon). In one embodiment, the compound administered is UNC4214A.

In one embodiment of the invention, a compound of Formula I, II, or III, as described herein, is administered to a host with a cancer in combination with one or more additional chemotherapeutic agents, resulting in a synergistic anti-cancer effect and the prolonged survival of a host compared to treatment with either a compound described herein or chemotherapeutic agent alone. In one embodiment, the use of a MerTKI compound described herein in combination with a chemotherapeutic agent provides for increased anti-tumor effects without an increase in the standard of care dosage of the chemotherapeutic agent. In one embodiment, the use of a MerTKI compound described herein in combination with a chemotherapeutic provides for equivalent or increased anti-tumor effects utilizing a lower dosage of a chemotherapeutic agent than the standard of care dosage.

In one embodiment, a compound of Formula I, II, or III, as described herein, is provided for use in treating a non-small cell lung carcinoma (NSCLC). In one embodiment, a method is provided to treat a host with non-small cell lung carcinoma (NSCLC) comprising administering to the host an effective amount of a compound of Formula I, II, or III, in combination with one or more additional chemotherapeutic agents. In one embodiment of the invention, a method is provided to treat a host with cancer comprising administering to the host an effective amount of a Mer TKI including active compounds of the present invention in combination with another tyrosine kinase inhibitor. In one embodiment, the tyrosine kinase inhibitor is a fibroblast growth factor receptor (FGFR) inhibitor. In one embodiment, the FGFR inhibitor is AZD-4547. In one embodiment, the cancer is non-small cell lung carcinoma (NSCLC). In some embodiments of the invention, a method is provided to treat a host with non-small cell lung carcinoma (NSCLC) comprising administering to the host an effective amount of a Mer TKI including active compounds of the present invention in combination with an additional tyrosine kinase inhibitor, wherein the Mer TKI is UNC4214A, and wherein the additional tyrosine kinase inhibitor is selected from the group consisting of gefitinib and crizotinib.

In one embodiment, a compound of Formula I, II, or III, as described herein, is provided for use in treating a melanoma. In one embodiment, the administration of the Mer TKI compound described herein is combined with a chemotherapeutic agent. In one embodiment, the chemotherapeutic agent is an anti-programmed cell death-1 (PD-1) agent. In one embodiment, the chemotherapeutic agent is a B-RAF inhibitor. In one embodiment, the B-RAF inhibitor is vemurafenib. In one embodiment, the host does not have a melanoma with a B-RAF mutation. In one embodiment, the host has a melanoma with a B-RAF mutation. In one embodiment, the host has a melanoma with a RAS mutation. In one embodiment, the melanoma over-expresses MerTK. In one embodiment, the melanoma has metastasized. In one embodiment, the MerTK inhibitory compound administered is UNC4214A.

In one embodiment, a compound of Formula I, II, or III, as described herein, is provided for use in treating Acute Lymphoblastic Leukemia (ALL). In one embodiment, a method is provided to treat a host with ALL comprising administering to the host an effective amount of a compound of Formula I, II, or III, in combination with methotrexate. In one embodiment, the MerTK inhibitory compound administered is UNC4214A.

In one embodiment, a compound of Formula I, II, or III, as described herein, is provided for use in treating Acute Myeloid Leukemia (AML). In one embodiment, the AML contains a wild type FLT3 protein. In one embodiment, the replication of the AML cells are dependent on FLT3 expression. In one embodiment, the AML contains a FLT3-ITD mutation. In one embodiment, the AML contains a FLT3-TKD mutation. In one embodiment, the AML contains both a FLT3-ITD and FLT3-TKD mutation. In one embodiment, a FLT3 or dual MER/FLT3 inhibitor described herein is administered to a host suffering from AML, wherein the AML contains a mutation within the FLT3-TKD at amino acid F691 or D835. In one embodiment, the MerTK inhibitory compound administered is UNC4214A.

In one embodiment, a tumor survival-signal inhibiting amount (for example 0.5 to 150 mg/dose) of Mer TKI including compounds of the present invention is administered to a host alone or in combination with a chemotherapeutic agent and/or anti-cancer targeted agent. In an alternative embodiment, a tumor survival-signal inhibiting amount (for example, at least 150 mg/dose, and in some embodiments, at least 200, 250, 300, 350, 400, 450, or 500 mg/dosage or more) of Mer TKI including active compounds of the present invention is administered to a host alone or in combination with a chemotherapeutic agent and/or anti-cancer targeted agent. In one embodiment, the Mer TKI and the chemotherapeutic agent act synergistically. In one embodiment, the use of a Mer TKI in combination with a chemotherapeutic agent provides for increased anti-tumor effects without an increase in the standard of care dosage of the chemotherapeutic agent.

In one embodiment, the use of a Mer TKI including compounds of the present invention in combination with a chemotherapeutic provides for equivalent or increased anti-tumor effects utilizing a lower dosage of a chemotherapeutic agent than the standard of care dosage.

In one aspect of the invention, the Mer TKI including compounds of the present invention can be administered to a host with a cancer prior to, during, or after administration with a chemotherapeutic agent or exposure to ionizing radiation. In one embodiment, a host is administered an effective amount of a chemotherapeutic agent or ionizing radiation and subsequently administered a Mer TKI.

In one embodiment, a method is provided to treat a host with cancer comprising administering to the host an effective amount of a compound of Formula I, II, or III, in combination with an immunomodulatory agent. In one embodiment, the immunomodulatory agent is selected from the group consisting of a CTLA-4 inhibitor, PD-1 or anti-PD-1 ligand, IFN-alpha, IFN-beta, and a vaccine, for example, a cancer vaccine. In one embodiment, a method is provided to treat a host with cancer comprising administering to the host an effective amount of a Mer TKI including active compounds of the present invention in combination with Keytruda® (pembrolizumab). In one embodiment, a method is provided to treat a host with cancer comprising administering to the host an effective amount of a Mer TKI including active compounds of the present invention in combination with Opdivo (nivolumab). In one embodiment, a method is provided to treat a host with cancer comprising administering to the host an effective amount of a Mer TKI including active compounds of the present invention in combination with Yervoy® (ipilimumab). In some embodiments, a method is provided to treat a host with cancer comprising administering to the host an effective amount of a Mer TKI including active compounds of the present invention in combination with an immunomodulatory agent selected from the group consisting of pembrolizumab and ipilimumab, wherein the Mer TKI is UNC4214A, wherein the cancer is melanoma.

In one embodiment, the Mer TKIs useful in the present invention, including active compounds of the present invention, are dual MER/Tyro3 TKIs. In one embodiment, the Mer TKIs are dual MER/Axl TKIs. In one embodiment, the Mer TKIs are dual MER/FLT-3 TKIs. In one embodiment, the Mer TKIs are MER-specific TKIs. In one embodiment, the Mer TKIs are Tyro3-specific TKIs.

Tumors.

The active compounds and methods described herein are useful for the treatment of tumors. As contemplated herein, the cancer treated can be a primary tumor or a metastatic tumor. In one aspect, the methods described herein are used to treat a solid tumor, for example, melanoma, lung cancer (including lung adenocarcinoma, basal cell carcinoma, squamous cell carcinoma, large cell carcinoma, bronchioloalveolar carcinoma, bronchiogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas and leiomyosarcomas, mixed mullerian tumors); glioma, glioblastoma, medulloblastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others.

In some embodiments, a method is provided to treat a host with a glioblastoma comprising administering to the host an effective amount of a Mer TKI including active compounds of the present invention in combination with temozolomide, wherein the Mer TKI is UNC4214A. In some embodiments, a method is provided to treat a host with a breast cancer comprising administering to the host an effective amount of a Mer TKI including active compounds of the present invention in combination with trastuzumab, wherein the Mer TKI is UNC4214A.

In one embodiment, the cancer is NSCLC. In one embodiment, the cancer is a melanoma. In one embodiment, the cancer is breast cancer. In one embodiment, the cancer is a glioblastoma. In one embodiment, the cancer is a bone cancer. In one embodiment, the cancer is a brain cancer. In one embodiment, the cancer is a colon cancer. In one embodiment, the cancer is a rectal cancer. In one embodiment, the cancer is an endometrial cancer. In one embodiment, the cancer is an esophageal cancer. In one embodiment, the cancer is a cancer of the gastrointestinal tract. In one embodiment, the cancer is a kidney cancer. In one embodiment, the cancer is a liver cancer. In one embodiment, the cancer is a lung cancer. In one embodiment, the cancer is a mantle cell lymphoma. In one embodiment, the cancer is an ovarian cancer. In one embodiment, the cancer is a pancreatic cancer. In one embodiment, the cancer is a pituitary cancer. In one embodiment, the cancer is a prostate cancer. In one embodiment, the cancer is a skeletal muscle cancer. In one embodiment, the cancer is a skin cancer. In one embodiment, the cancer is a stomach cancer. In one embodiment, the cancer is a thyroid cancer. In one embodiment, the cancer is a neuroendocrine cancer. In one embodiment, the cancer is a gastroesophageal cancer. In one embodiment, the cancer is a renal cell cancer. In one embodiment, the cancer is a head and neck cancer. In some embodiments, the Mer TKI used to treat a host having a cancer is UNC4214A.

In one embodiment, the methods described herein are useful for treating a host suffering from a lymphoma or lymphocytic or myelocytic proliferation disorder or abnormality. For example, the Mer TKIs as described herein can be administered to a subject suffering from a Hodgkin Lymphoma of a Non-Hodgkin Lymphoma. For example, the subject can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, the subject may be suffering from a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

In one embodiment, the methods as described herein may be useful to treat a host suffering from a specific T-cell, a B-cell, or a NK-cell based lymphoma, proliferative disorder, or abnormality. For example, the subject can be suffering from a specific T-cell or NK-cell lymphoma, for example, but not limited to: Peripheral T-cell lymphoma, for example, peripheral T-cell lymphoma and peripheral T-cell lymphoma not otherwise specified (PTCL-NOS); anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma. and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

Alternatively, the subject may be suffering from a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mantle cell lymphoma (MCL); Burkitt lymphoma; Mediastinal large B cell lymphoma; Waldenstrim macroglobulinemia; Nodal marginal zone B cell lymphoma (NMZL); Splenic marginal zone lymphoma (SMZL); Intravascular large B-cell lymphoma; Primary effusion lymphoma; or Lymphomatoid granulomatosis; Chronic lymphocytic leukemia/small lymphocytic lymphoma; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma and Burkitt lymphoma; B-cell lymphoma, unclassifiable, with features intermediate between diffuse large B-cell lymphoma and classical Hodgkin lymphoma; Nodular sclerosis classical Hodgkin lymphoma; Lymphocyte-rich classical Hodgkin lymphoma; Mixed cellularity classical Hodgkin lymphoma; or Lymphocyte-depleted classical Hodgkin lymphoma.

In one embodiment, the methods described herein can be used to a subject suffering from a leukemia. For example, the subject may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); T-cell prolymphocytic leukemia (TPLL); large granular lymphocytic leukemia; or Adult T-cell chronic leukemia; large granular lymphocytic leukemia (LGL). In one embodiment, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

Acute Myeloid Leukemia.

In one embodiment, the methods described herein can be used to treat a host suffering from Acute Myeloid Leukemia (AML). In one embodiment, the AML contains a wild type FLT3 protein. In one embodiment, the replication of the AML cells are dependent on FLT3 expression. In one embodiment, the AML contains a FLT3-ITD mutation. In one embodiment, the AML contains a FLT3-TKD mutation. In one embodiment, the AML contains both a FLT3-ITD and FLT3-TKD mutation.

FLT3-ITD mutations are well known in the art. FLT3-TKD mutations are also well known in the art. In one embodiment, a FLT3 or dual MER/FLT3 inhibitor is administered to a host suffering from AML, wherein the AML contains a mutation within the FLT3-TKD at amino acid F691 or D835. In one embodiment, the FLT3-TKD mutation is selected from D835H, D835N, D835Y, D835A, D835V, D835V, D835E, I836F, I836L, I836V, I836D, I836H, I836M, and F691L. In one embodiment, the host is suffering from the FLT3-TKD mutation D835Y. In one embodiment, the host is suffering from the FLT3-TKD mutation F691L.

In one embodiment, the host is suffering from acute promyelocytic leukemia (a subtype of AML); a minimally differentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryocytic leukemia (M7). In one embodiment, the host is suffering from AML that has relapsed or become refractory to previous treatments. In one embodiment, the host has previously been treated with a FLT3 inhibitor or other chemotherapeutic agent.

In one embodiment, the FLT3 inhibitors are efficacious against AML having both FLT3-ITD and FLT3-TKD mutations, wherein resistance to other FLT3 inhibitors, for example, AC220, has been established.

In one embodiment, the host has an Acute Myeloid Leukemia (AML) comprising a FLT3 mutation, wherein the mutation confers resistance to a FLT3 inhibitor other than the FLT3 inhibitors described herein. In one embodiment, the host has a AML comprising a FLT3 mutation, wherein the mutation has conferred resistance to quizartinib (AC220) or other FLT3 inhibitor selected from lestaurtinib, sunitinib, sorafenib, tandutinib, midostaurin, amuvatinib crenolanib, dovitinib, ENMD-2076 (Entremed), or KW-2449 (Kyowa Hakko Kirin), or a combination thereof.

Chemotherapeutic Agents.

In one embodiment, an active compound or Mer TKI as described herein is used in combination or alternation with a chemotherapeutic agent. Such agents may include, but are not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof). Examples of mTOR inhibitors include but are not limited to rapamycin and its analogs, everolimus (Afinitor), temsirolimus, ridaforolimus, sirolimus, and deforolimus. Examples of P13 kinase inhibitors include but are not limited to Wortmannin, demethoxyviridin, perifosine, idelalisib, PX-866, IPI-145, BAY 80-6946, BEZ235, RP6503, TGR 1202 (RP5264), MLN1117 (INKl117), Pictilisib, Buparlisib, SAR245408 (XL147), SAR245409 (XL765), Palomid 529, ZSTK474, PWT33597, RP6530, CUDC-907, and AEZS-136. Examples of MEK inhibitors include but are not limited to Tametinib, Selumetinib, MEK162, GDC-0973 (XL518), and PD0325901. Examples of RAS inhibitors include but are not limited to Reolysin and siGl2D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol. In one embodiment, the chemotherapeutic agent is an anti-programmed cell death-1 (PD-1) agent, for example, nivolumab, pembrolizumab, BMS936559, lambrolizumab, MPDL3280A, pidilizumab, AMP-244, and MEDI4736. In one embodiment, the chemotherapeutic agent is a B-RAF inhibitor, for example, vemurafenib or sorafenib. In one embodiment, the chemotherapeutic agent is a FGFR inhibitor, for example, but not limited to, AZD4547, dovitinib, BGJ398, LY2874455, and ponatinib. In one embodiment, an active compound or Mer TKI as described herein is used in combination with crizotinib.

In certain aspects, the additional therapeutic agent is an anti-inflammatory agent, a chemotherapeutic agent, a radiotherapeutic, an additional therapeutic agent, or an immunosuppressive agent.

Suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCl, daunorucbicin citrate, denileukin diftitox, Dexrazoxane, Dibromomannitol, dihydroxy anthracin dione, Docetaxel, dolasetron mesylate, doxorubicin HCl, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCl, glucocorticoids, goserelin acetate, gramicidin D, granisetron HCl, hydroxyurea, idarubicin HCl, ifosfamide, interferon α-2b, irinotecan HCl, letrozole, leucovorin calcium, leuprolide acetate, levamisole HCL, lidocaine, lomustine, maytansinoid, mechlorethamine HCl, medroxyprogesterone acetate, megestrol acetate, melphalan HCl, mercaptipurine, mesna, methotrexate, methyltestosterone, mithramycin, mitomycin C, mitotane, mitoxantrone, nilutamide, octreotide acetate, oligomycin A, ondansetron HCL, paclitaxel, pamidronate disodium, pentostatin, pilocarpine HCl, plimycin, polifeprosan 20 with carmustine implant, porfimer sodium, procaine, procarbazine HCl, propranolol, rituximab, sargramostim, streptozotocin, tamoxifen, taxol, teniposide, tenoposide, testolactone, tetracaine, thioepa chlorambucil, thioguanine, thiotepa, topotecan HCl, toremifene citrate, trastuzumab, tretinoin, valrubicin, vinblastine sulfate, vincristine sulfate, and vinorelbine tartrate. In one embodiment, an active compound or Mer TKI as described herein is used in combination with oligomycin A.

Additional therapeutic agents that can be administered in combination with a compound disclosed herein can include bevacizumab, sutinib, sorafenib, 2-methoxyestradiol or 2ME2, fmasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, ABT-888, temozolomide, erlotinib, lapatinib, sunitinib, FTS, AZD6244, BEZ235, and celecoxib. In one embodiment, an active compound or Mer TKI as described herein is used in combination with gefitinib.

In one embodiment, a FLT3 or dual MER/FLT3 inhibitor described herein is used in combination with a chemotherapeutic agent for the treatment of AML. Such agents may include, but are not limited to, cytarabine (ara-C), anthracycline drugs including but not limited to, daunorubicin, idarubicin; cladribine, fludarabine, Gleevec® (imatinib), Sprycel® (dasatinib), adriamycin, arsenic trioxide, cerubidine, clafen, cyclophosphamide, cytarabine, daunorubicin, doxorubicin, vincristine, and topotecan. Some of the other chemo drugs that may be used to treat AML include: etoposide (VP-16), 6-thioguanine (6-TG), hydroxyurea (Hydrea®), Corticosteroid drugs, such as prednisone or dexamethasone (Decadron®), methotrexate (MTX), 6-mercaptopurine (6-MP), azacitidine (Vidaza®), and decitabine (Dacogen®). In one embodiment, a FLT3 or dual MER/FLT3 inhibitor described herein is used in combination with cytarabine.

In one embodiment, a FLT3 or dual MER/FLT3 inhibitor described herein is used in combination with an additional FLT3 inhibitor to treat with a host suffering from AML. Additional FLT3 inhibitors for use in combination with the FLT3 or dual MER/FLT3 inhibitors described herein include lestaurtinib, sunitinib, sorafenib, tandutinib, midostaurin, crenolanib, dovitinib, ENMD-2076 (Entremed), amuvatinib, or KW-2449 (Kyowa Hakko Kirin).

In one embodiment, a FLT3 or dual MER/FLT3 inhibitor described herein is used in combination with a Ras inhibitor. Examples of RAS inhibitors include but are not limited to Reolysin, FusOn-H2, and siG12D LODER.

In one embodiment, a FLT3 or dual MER/FLT3 inhibitor described herein is used in combination with a Phosphoinositide 3-kinase inhibitor (PI3K inhibitor). PI3K inhibitors that may be used in the present invention are well known. Examples of PI3K inhibitors include but are not limited to Wortmannin, demethoxyviridin, perifosine, idelalisib, Pictilisib, Palomid 529, ZSTK474, PWT33597, CUDC-907, AEZS-136, PX-866, IPI-145, RP6503, SAR245408 (XL147), duvelisib, GS-9820, GDC-0032 (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo){[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide), TGX-221 ((±)-7-Methyl-2-(morpholin-4-yl)-9-(1-phenylaminoethyl)-pyrido[1,2-a]-pyrimidin-4-one), GSK263 6771 (2-Methyl-1-(2-methyl-3-(trifluoromethyl)benzyl)-6-morpholino-1H-benzo[d] imidazole-4-carboxylic acid dihydrochloride), KIN-193 ((R)-2-((1-(7-methyl-2-morpholino-4-oxo-4H-pyrido[1,2-a] pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl) thieno[3,2-d]pyrimidine), GDC-0980 ((S)-1-(4-((2-(2-aminopyrimidin-5-yl)-7-methyl-4-morpholinothieno[3,2-d] pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3 aR,6E,9S,9aR,10R,11aS)-6-[[bis(prop-2-enyl) amino]methylidene]-5-hydroxy-9-(methoxymethyl)-9a,11a-dimethyl-1,4,7-trioxo-2,3,3a,9,10,11-hexahydroindeno[4,5h]isochromen-10-yl]acetate (also known as sonolisib)), and the structure described in WO2014/071109 having the formula:

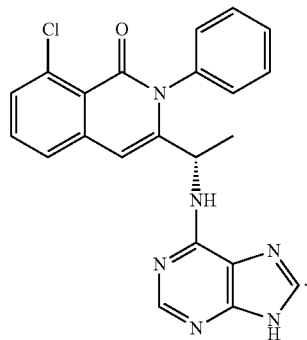

Compound 292

In one embodiment, a FLT3 or dual MER/FLT3 inhibitor described herein is used in combination with a modulator of the STAT5 pathway. Compounds which modulate the Janus Kinase 2 (JAK2)—Signal Transducer and Activator of Transcription 5 (STAT5) pathway include but are not limited to Lestaurtinib, Ruxolitinib, SB1518, CYT387, LY3009104, INC424, LY2784544, BMS-911543, NS-018, and TG101348.

In one embodiment, a FLT3 or dual MER/FLT3 inhibitor described herein is used in combination with an AKT inhibitor, including but not limited to, MK-2206, GSK690693, Perifosine, (KRX-0401), GDC-0068, Triciribine, AZD5363, Honokiol, PF-04691502, and Miltefosine.

Immunomodulatory Combination Agents.

Active compounds as described herein used in a dosage for direct effect on the diseased cell can be used in combination with one or more immunotherapy agents for additive or synergistic efficacy against solid tumors. In one embodiment, a tumor associated macrophage MerTK TK inhibiting amount of a Mer TKI is used in combination or alternation with the immunomodulatory agent. In another embodiment, a host tumor survival-signal inhibiting, antiviral or antibacterial amount of a Mer TKI is used in combination or alternation with the immunomodulatory agent.

Immunomodulators are small molecules or biologic agents that treat a disease by inducing, enhancing or suppressing the host's immune system. In the present application, one or more immunomodulators are selected that induce or enhance the host's immune system. Some immunomodulators boost the host's immune system and others help train the host's immune system to better attack tumor cells. Other immunomodulators target proteins that help cancer grow.

Three general categories of immunotherapies are antibodies, cancer vaccines, and non-specific immunotherapies. Antibodies are typically administered as monoclonals, although that is not required. "Naked monoclonal antibodies" work by attaching to antigens on tumor cells. Some antibodies can act as a marker for the body's immune system to destroy the tumor cells. Others block signaling agents for tumor cells. Antibodies can generally be used to bind to any signaling or metabolic agent that directly or indirectly facilitates tumor growth. Examples are alemtuzumab (Campath) which binds to CD52 antigen, and trastuzumab (Herceptin), which binds to the HER2 protein.

In another embodiment, an antibody can be used that is conjugated to another moiety that increases it delivery or efficacy. For example, the antibody can be connected to a cytotoxic drug or a radiolabel. Conjugated antibodies are sometimes referred to as "tagged, labeled or loaded". Radiolabeled antibodies have small radioactive particles attached to them. Examples are Zevalin, which is an antibody against CD20 used to treat lymphoma. Chemolabeled antibodies are antibodies that have cytotoxic agents attached to them. Examples are Adcetris, which targets CD30, and Kadcyla, which targets HER2. Ontak, while not an antibody, is similar in that it is interleukin-2 attached to a toxin from diphtheria.

Another category of immunotherapy that can be used in the present invention is a cancer vaccine. Most cancer vaccines are prepared from tumor cells, parts of tumor cells or pure antigens. The vaccine can be used with an adjuvant to help boost the immune response. An example is Provenge, which is the first cancer vaccine approved by the US FDA. The vaccine can for example be a dendritic cell vaccine or a vector-based vaccine Nonspecific tumor immunotherapies and adjuvants include compounds that stimulate the immune system to do a better job at attacking the tumor cells. Such immunotherapies include cytokines, interleukins, interferons (α primarily but can be also β or γ). Specific agents include granulocyte-macrophage colony-stimulating factor (GM-CSF), IL-12, IL-7, IL-21, drugs that target CTLA-4 (such as Yervoy, which is Ipilimumab) and drugs that target PD-1 or PDL-1 (such as for example, nivolumab (BMS), pembrolizumab (Merck), pidilizumab (CureTech/Teva), AMP-244 (Amplimmune/GSK), BMS-936559 (BMS), and MEDI4736 (Roche/Genentech)).

Other drugs that boost the immune system are thalidomide, lenalidomide, pomalidomide, the Bacille Calmette-Gurin bacteria and Imiquimod. Additional therapeutic agents that can be used in combination with the MerTK inhibitor include bispecific antibodies, chimeric antigen receptor (CAR) T-cell therapy and tumor-infiltrating lymphocytes.

In one aspect of the present invention, a compound described herein can be combined with at least one immunosuppressive agent. The immunosuppressive agent is preferably selected from the group consisting of a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a SIP receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA41g (Abatacept), belatacept, LFA31g, etanercept (sold as Enbrel® by Immunex), adalimumab (Humira®), infliximab (Remicade®), an anti-LFA-1 antibody, natalizumab (Antegren®), Enlimomab, gavilimomab, anti-thymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

5. Immunomodulatory and Immunostimulatory Agents

It has also been discovered that the compounds described herein can be used as immunomodulatory agents that reverse the MerTK-induced suppression of proimflammatory cytokines such as wound healing cytokines (IL-10 and GAS6) and enhance the expression of acute inflammatory cytokines (IL-12 and IL-6). In this way, the pyrazolopyrimidine compounds can "re-normalize" or "re-program" the host microenvironment in the diseased tissue area to attack the diseased cells. This immunostimulatory activity can be used therapeutically to treat a host with a tumor, cancer or other neoplasm, or alternatively, to treat a host with an infection, for example, a viral or bacterial infection.

Taking advantage of the immunostimulatory activity of the compounds described herein, or a pharmaceutically acceptable composition, salt, isotopic analog, or prodrug thereof, may be used for the treatment of a MERTK-negative (−/−) tumor or cancer. In one embodiment, the cancer is a MERTK-negative (−/−) breast cancer.

Therefore, as part of the invention, one or more of the compounds disclosed herein can be used as adjunctive therapy for its immunostimulatory effect as a means to increase the efficacy of the antineoplastic standard of care therapies, such as chemotherapeutic compounds or radiation.

In another aspect of the invention, one or more of the compounds disclosed herein can be used as adjunctive therapy for its immunostimulatory effect as a means to increase the efficacy of the antiviral or antibacterial standard of care therapies.

For example, a compound of Formula I, II, or III, or another compound as described herein, is administered to a host in an immunomodulatory effective amount to inhibit Mer tyrosine kinase activity in the host's tumor associated macrophage to suppress tumor immunity. In one embodiment, the dosage of the Mer TKI administered as an immunomodulatory agent to stimulate innate anti-tumor immunity is lower than a dosage of a Mer TKI administered to a host as a direct anti-cancer agent. In one embodiment, the Mer TKI is administered at a dosage which exhibits immunomodulatory but not direct cytotoxic effect.

In one embodiment, the cancer is a MERTK-negative (−/−) cancer. In one embodiment, the MerTK inhibitory compound administered is UNC4214A.

Without wanting to be bound by any particular theory, it is believed that the administration of a chemotherapeutic agent results in the apoptosis of tumor cells, exposing antigenic tumor proteins. The host's innate immune system is thus stimulated to recognize the antigenic apoptotic components from the tumor cells after chemotherapy or ionizing radiation and mount an immune response. In one embodiment, the administration of a chemotherapeutic agent or ionizing radiation, before, with or subsequently followed by the administration of a Mer TKI is carried out using the normal standard of care chemotherapeutic protocol. In another embodiment, the standard of care protocol of the chemotherapeutic is changed in a manner that causes less toxicity to the host due to the adjunctive or synergistic activity of the Mer TKI.

In one embodiment, a method for the treatment of a tumor is provided that includes administering an effective amount of a Mer TKI to inhibit TK signaling in a tumor associated macrophage, without inhibiting the survival signal in the tumor itself. In this way, the Mer TKI can be used to ramp up the immune response to the tumor by inhibiting macrophage tumorigenic tolerance during normal tumor chemotherapeutic agent. The immunomodulatory dosage of the Mer TKI can be given prior to, with or after chemotherapeutic therapy and can be used simultaneously with or intermittently with the chemotherapeutic therapy. In one embodiment, less chemotherapeutic therapy is needed than the normal standard of care defined for that chemotherapeutic agent, due to the increased efficacy of the immune response in the surrounding tumor microenvironment. In one embodiment, a dose of Mer TKI including active compounds of the present invention (for example 0.5 to 150 mg/dose) is given as a type of adjunctive therapy with the chemotherapeutic agent.

In one aspect of the invention, a Mer TKI is administered to a host having a cancer as an immunomodulatory agent to inhibit Mer tyrosine kinase activity in a tumor associated macrophage in order to suppress tumor immunity. In one embodiment, the dosage of the Mer TKI administered as an immunomodulatory agent to stimulate innate anti-tumor immunity is lower than a dosage of a Mer TKI administered to a host as a direct anti-cancer agent. In one embodiment, the Mer TKI is administered at a dosage which exhibits immunomodulatory but not direct cytotoxic effects on the cancer.

In one embodiment, the dose associated with the immunomodulatory effect of an active compound of the present invention is about 2-fold, about 3-fold, about 4-fold, about 5-fold, about 6-fold, about 7-fold, about 8-fold, about 9-fold, about 10-fold or greater lower than the dose associated with a direct survival-signal inhibiting anti-tumor or cytotoxic effect, or the direct antiviral or antibacterial effect. In one embodiment, the dose used to induce an immunomodulatory effect in a host is between about 0.5 mg and about 150 mg. In one embodiment, the dose is about 1 mg, about 2 mg, about 3 mg, about 4 mg, about 5 mg, about 10 mg, about 12 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 125 mg, about 140 mg, or about 150 mg.

6. Anti-Infective Agents

It has been discovered that an effective amount of the pyrimidinyl compounds described in Formulas I, II, and III below or as otherwise provided herein, can be administered as an immunomodulatory agent to stimulate the innate immune system. This immunostimulatory activity can be used therapeutically to treat a host with an infection. In one embodiment, the infection is a viral infection. In one embodiment, the infection is a bacterial infection. In an alternative embodiment, an effective amount of the active compounds described herein can be used to treat a host bearing any virus-related infection where the virus has a virion envelope phosphatidyl serine that complexes with MerTK to achieve viral entry or is otherwise facilitated by MerTK in the infectious process or maintenance.

Viral Infections.

The virus may be an enveloped virus or a non-enveloped virus. In one embodiment, the host is infected or threatened to become infected with a virus selected from, for example, Flaviviridae viruses, including Flavivirus (such as Yellow Fever, West Nile and Dengue), Hepacivirus (Hepatitis C virus, "HCV"), Pegivirus and Pestivirus (Bovine viral diarrhea virus); Filoviridae viruses, including Ebola viruses; Togaviridae viruses, including Chikungunya virus; Coronaviruses, such as SARS (Severe acute respiratory syndrome) and MERS (Middle East respiratory syndrome); Orthomyxoviridae viruses, for example influenza; Paramyxoviridae viruses, for example Respiratory syncytial virus (RSV), measles and mumps; and Caliciviridae viruses, including Lagovirus, Vesivirus, and Sapovirus and Norovirus (Norwalk-like virus), and Lentiviruses, for example, HIV. In one embodiment, an active compound disclosed herein is administered in combination or alternation with another anti-viral agent for combination therapy. In one embodiment, the compound administered is UNC4214A.

More broadly, the host to be treated may be infected with an enveloped virus including, but not limited to, viruses of the following families: Bornaviridae, Bunyaviridae, Coronaviridae, Filoviridae, Flaviviridae, Hepadnaviridae, Herpesviridae, Nyamiviridae, Orthomyxoviridae, Paramyxoviridae, Poxviridae, Retroviridae, Rhabdoviridae, and Togaviridae. Examples of viruses form the Bunyaviridae family include, but are not limited to, bunya viruses such as La Crosse virus and Hantaan. Examples of viruses from the Coronaviridae family include, but are not limited to, coronaviruses such as SARS virus or Toroviruses. Examples of viruses from the Filoviridae family include, but are not limited to, Ebola and Marburg. Examples of viruses from the Flaviridae family include, but are not limited to, dengue, encephalitis viruses including West Nile virus, Japanese encephalitis virus and yellow fever virus and Hepatitis C virus. Examples of viruses from the Hepadnaviridae family include, but are not limited to, Hepatitis B. Examples of viruses from the Herpesviridae family include, but are not limited to, cytomegalovirus, herpes simplex viruses 1 and 2, HHV-6, HHV-7, HHV-8, pseudorabies virus, and varicella zoster virus. Examples of viruses from the Orthomyxoviridae family include, but are not limited to, influenza virus. Examples of viruses from the Paramyxoviridae family include, but are not limited to, measles, metapneumovirus, mumps, parainfluenza, respiratory syncytial virus, and sendai. Examples of viruses from the Poxviridae family include, but are not limited to, pox viruses such as smallpox, monkey pox, and Molluscum contagiosum virus, variola viruses, vaccinia virus, and yatapox viruses such as Tanapox and Yabapox. Examples of viruses from the Retroviridae family include, but are not limited to, Coltiviruses such as CTFV and Banna virus, human immunodeficiency viruses such as HIV-1 and HIV-2, murine leukemia virus, simian immunodeficiency virus, feline immunodeficiency virus, human T-cell leukemia viruses 1 and 2, and XMRV. Examples of viruses from the Rhabdoviridae family include, but are not limited to, vesicular stomatitis and rabies. Examples of viruses from the Togaviridae family include, but are not limited to, rubella viruses or alpha viruses such as Chikungunya virus, Eastern equine encephalitis virus, O'nyong'nyong virus, Ross River virus, Semliki Forest virus, Sindbis, Venezuelan equine encephalitis or Western equine encephalitis virus.

In one embodiment, the host is infected with Chikungunya virus. In one embodiment, the host is infected with Ebola virus. In one embodiment, an active compound or Mer TKI as described herein is used in combination with brincidofovir (CMX001).

In another particular embodiment, the host is infected with a non-enveloped virus, sch as, but not limited to, viruses of the following families: Adenoviridae, Arenaviridae, Birnaviridae, Calciviridae, Iridoviridae, Ophioviridae Parvoviradae, Papillomaviridae, Papovaviridae, Picornaviridae, and Reoviridae. Examples of viruses from the Adenoviridae family include, but are not limited to adenoviruses. Examples of viruses from the Arenaviradae family include, but are not limited to, hemorrhagic fever viruses such as Guanarito, LCMV, Lassa, Junin, and Machupo. Examples of viruses from the Iridoviridae family include, but are not limited to, African swine fever virus. Examples of viruses from the Papillomavirus family include, but are not limited to, papillomaviruses. Examples of viruses from the Papovaviridae family include, but are not limited to, polyoma viruses such as BK virus and JC virus. Examples of viruses from the Parvoviridae family include, but are not limited to, parvoviruses such as human bocavirus and adeno-associated virus. Examples of viruses from the Picornaviridae family include, but are not limited to, aptoviruses, cardioviruses, coxsackieviruses, echoviruses, enteric viruses, enteroviruses, foot and mouth disease virus, hepatitis A virus, hepatoviruses, Poliovirus, and rhinovirus. Examples of viruses from the Reoviradae family include, but are not limited to, orbiviruses, reoviruses and rotaviruses.

In another embodiment, a host is infected with a virus such as an astroviruses, caliciviruses including but not limited to, Norovirus and Norwalk, and Hepeviruses including, but not limited to, Hepatitis E.

As described above, a compound described herein can be administered to a host suffering from a viral infection in combination with another anti-viral or anti-infective compound. Antiviral compounds that can be used in combination with the compounds described herein include, but are not limited to, abacavir, acyclovir, adefovir, amantadine, amprenavir, ampligen, arbitol, atazanavir, balavir, boceprevir, boceprevirertet, cidofovir, dolutegravir, darunavir, delavirdine, didanosine, docosanol, edoxudine, efavirenz, emtricitabine, epivir, enfuvirtide, entecavir, famciclovir, fomivirsen, fosamprenavir, foscarnet, fosfonet, ganciclovir, ibacitabine, imunovir, idoxuridine, imiquimod, indinavir, lamivudine, lopinavir, loviride, maraviroc, moroxydine, nelfinavir, nevirapine, nexavir, oseltamivir, penciclovir, peramivir, pleconaril, podophyllotoxin, raltegravir, ribavirin, rilpivirine, rimantadine, pyramidine, saquinavir, simeprevir, sofosbuvir, stavudine, telaprevir, tenofovir, tipranavir, trifluridine, trizivir, tromantadine, traporved, truvada, valaciclovir, valganciclovir, vicriviroc, vidarabine, viramidine, zalcitabine, zanamivir, and zidovudine.

In one embodiment, a host is infected with a human immunodeficiency virus and is administered a compound described herein in combination with the anti-HIV combination drug, such as Atripla® or other drug that includes emtricitabine. In another embodiment, the patient with the human immunodeficiency virus can be treated with atazanavir, ritonavir, or Truvada® in combination with a compound described herein. In another embodiment, the patient infected with human immunodeficiency virus can be treated with the combination of dolutegravir, Truvada® and a compound described herein. In another embodiment, human immunodeficiency virus can be treated with the combination dolutegravir, Epzicom® and a compound described herein. In another embodiment, a host infected with human immunodeficiency virus can be treated with a combination of raltegravir, Truvada® and a compound described herein. In another embodiment, a host infected with human immunodeficiency virus can be treated with the combination of Complera® and a compound described herein. It will be appreciated by one skilled in the art that a host infected with HIV can be treated with a number of combinations of drugs depending on the mutation pattern of the virus. The patient can be treated with an appropriate combination of drugs in combination with a compound described herein.

In one embodiment, the host is infected with a hepatitis C virus and is treated with an anti-hepatitis C drug in addition to the active compound described herein. For example, the patient can be treated with a combination of Sovaldi™, Harvoni®, ribavirin, and/or a pegylated interferon and a compound described herein. In one embodiment the pegylated interferon is PegIntron®. In another embodiment, the pegylated interferon is Pegasys®. In one embodiment, the host infected with hepatitis C virus is treated with Sovaldi™, ribavirin and a compound described herein. In one embodiment, the host infected with hepatitis C virus is treated with Harvoni®, ribavirin and a compound described herein. In one embodiment, a host infected with hepatitis C virus is treated with a combination of Olysio™, ribavirin, a pegylated interferon and a compound described herein. In one embodiment the pegylated interferon is PegIntron®. In another embodiment, the pegylated interferon is Pegasys®. In one embodiment, the host is infected with a hepatitis C virus and is treated with a combination of ABT-267, ABT-333 and ABT-450/ritonavir, in addition to an active compound described herein. In one embodiment, the host is infected with a hepatitis C virus and is treated with a combination of MK-5172 and MK-8742, in addition to an active compound described herein.

In one embodiment, a host infected with hepatitis C genotype 1 is treated with a combination of Sovaldi™, ribavirin, a pegylated interferon and a compound described herein for 12 weeks. In another embodiment, a host infected with hepatitis C genotype 1 is treated with Sovaldi™ and a compound described herein for 12 weeks followed by ribavirin, pegylated interferon and a compound described herein for 24 weeks. In one embodiment, a host infected with hepatitis C genotype 2 is treated with Sovaldi™, ribavirin, and a compound described herein for 12 weeks. In one embodiment, a host infected with hepatitis C genotype 3 is treated with Sovaldi™, ribavirin, and a compound described herein for 24 weeks. In another embodiment, a host infected with hepatitis C genotype 3 is treated with Sovaldi™, ribavirin, pegylated interferon, and a compound described herein for 12 weeks. In one embodiment, a host infected with hepatitis C genotype 4 is treated with Sovaldi™, ribavirin, pegylated interferon, and a compound described herein for 12 weeks. In another embodiment, a host infected with hepatitis C genotype 4 is treated with a combination of Olysio™, and a compound described herein for 12 weeks followed by ribavirin, pegylated interferon and a compound described herein for 24-28 weeks.

In one embodiment, a host infected with hepatitis C genotype 5 is treated with Sovaldi™, ribavirin, pegylated interferon, and a compound described herein for 12 weeks. In one embodiment, a host infected with hepatitis C genotype 5 is treated with ribavirin, pegylated interferon, and a compound described herein for 48 weeks. In one embodiment, a host infected with hepatitis C genotype 6 is treated with Sovaldi™, ribavirin, pegylated interferon, and a compound described herein for 12 weeks. In one embodiment, a host infected with hepatitis C genotype 6 is treated with ribavirin, pegylated interferon, and a compound described herein for 48 weeks.

In one embodiment, a host infected with hepatitis C genotype 1 is treated with Sovaldi™, Olysio™, ribavirin, and a compound described herein for 12 weeks. In another embodiment, a host infected with hepatitis C genotype 1 is treated with Sovaldi™, ribavirin, and a compound described herein for 24 weeks. In one embodiment, a host infected with hepatitis C genotype 2 is treated with Sovaldi™, ribavirin, and a compound described herein for 12 weeks. In one embodiment, a host infected with hepatitis C genotype 3 is treated with Sovaldi™, ribavirin, and a compound described herein for 24 weeks. In one embodiment, a patient infected with hepatitis C genotype 4 is treated with Sovaldi™, ribavirin, and a compound described herein for 24 weeks.

In one embodiment, a host infected with papilloma virus is treated with imiquimod and a compound described herein. In another embodiment, a host infected with papilloma virus is treated with cryotherapy and a compound described herein. In another embodiment, papilloma virus is surgically removed from a host and the host is treated with a compound described herein. In one embodiment, the host receives a compound described herein prior to, during, and post-surgery. In one embodiment, the patient receives a compound described herein post-surgery.

In one embodiment a host infected with herpes simplex type 2 is treated with Famvir® and a compound described herein. In one embodiment a host infected with herpes simplex type 1 is treated with acyclovir and a compound described herein. In another embodiment, a host infected with herpes simplex type 2 is treated with acyclovir and a compound described herein. In one embodiment, a host infected with herpes simplex type 1 is treated with Valtrex® and a compound described herein. In another embodiment, a host infected with herpes simplex type 2 is treated with Valtrex® and a compound described herein. In one embodiment, a host infected with herpes simplex type 1 virus receives a compound described herein for 7 days prior to treatment with acyclovir. In one embodiment, a host infected with herpes simplex type 2 virus receives a compound described herein for 7 days prior to treatment with acyclovir. In one embodiment, a host infected with herpes simplex type 1 virus receives a compound described herein for 7 days prior to treatment with Valtrex®. In one embodiment, a host infected with herpes simplex type 2 virus receives a compound described herein for 7 days prior to treatment with Valtrex®.

In one embodiment a host infected with varicella zoster virus, VZV, is treated with acyclovir and a compound described herein. In another embodiment a host infected with varicella zoster virus, VZV, is treated with Valtrex® and a compound described herein. In one embodiment ahost infected with varicella zoster virus, VZV, is treated with famciclovir and a compound described herein. In another embodiment a host infected with varicella zoster virus, VZV, is treated with foscarnet and a compound described herein. In one embodiment, a host infected with varicella zoster virus is treated with a compound described herein prior to vaccination with Zostavax®. In another embodiment, a host infected with varicella zoster virus is treated with a compound described herein prior to and post vaccination with Zostavax®.

In one embodiment a host infected with influenza virus is treated with Relenza® and a compound described herein. In another embodiment a host infected with influenza virus is treated with Tamiflu® and a compound described herein. In another embodiment a host is infected with influenza virus and is treated with amantadine and a compound described herein. In another embodiment, a host infected with influenza virus is treated with rimantadine and a compound described herein.

In one embodiment, a host infected with cytomegalovirus is treated with valganciclovir and a compound described herein. In another embodiment, a host infected with cytomegalovirus is treated with ganciclovir and a compound described herein. In one embodiment, a host infected with cytomegalovirus is treated with foscarnet and a compound described herein. In another embodiment, a host infected with cytomegalovirus is treated with cidofovir and a compound described herein.

In one embodiment, a host infected with hepatitis B virus is treated with lamivudine and a compound described herein. In another embodiment, a host infected with hepatitis B virus is treated with adefovir and a compound described herein.

In one embodiment, a host infected with hepatitis B virus is treated with tenofovir and a compound described herein. In another embodiment, a host infected with hepatitis B virus is treated with telbivudine and a compound described herein.

Bacterial Infections.

In one embodiment of the present invention, a compound of Formula I, II, or III, or other active compound described herein, is used in an effective amount to treat a host infected with a bacterial infection. In one embodiment, the bacteria treated is, for example, a Gram-negative bacilli (GNB), especially *Escherichia coli*, Gram-positive cocci (GPC), *Staphylococcus aureus, Enterococcus faecalis*, or *Streptococcus pneumoniae*. In one embodiment, the bacterial infection may be caused, for example, by a Gram-negative bacteria, including, but not limited to *Escherichia coli, Salmonella*, and other Enterobacteriaceae, *Pseudomonas, Moraxella, Helicobacter, Stenotrophomonas*, Bdellovibrio, acetic acid bacteria, *Legionella, Staphylococcus aureus, Hemophilus influenzae, Klebsiella pneumoniae, Legionella pneumophila, Pseudomonas aeruginosa, Vibrio cholerae, Proteus mirabilis, Enterobacter cloacae, Serratia marcescens, Clostridium tetani, Helicobacter pylori, Salmonella enteritidis, Salmonella typhi, Shigella flexneri*, or *Acinetobacter baumanii*. In one embodiment, the bacterial infection may be caused, for example, by a Gram-positive species from the following genera: *Bacillus, Listeria, Staphylococcus, Enterococcus, Lactobacillus, Lactococcus, Leuconostoc, Pedicoccus, Streptococcus, Acetobacterium, Clostridium, Eubacterium, Heliobacterium, Heliospirillum, Megasphaera, Pectinatus, Selenomonas, Zymophilus, Sporomusa, Mycoplasma, Spiroplasma, Ureaplasma*, or *Erysipelothrix*.

In one embodiment, the bacterial infection is associated with liver failure. In one embodiment, an active compound disclosed herein is administered in combination with an antibiotic or another anti-bacterial agent. In one embodiment, the compound administered is UNC4214A.

In one embodiment, the bacterial infection is associated with liver failure. In one embodiment, an active compound disclosed herein is administered in combination with an antibiotic or another anti-bacterial agent. In one embodiment, the compound administered is UNC4214A.

In one embodiment, a patient is suffering from acute-on-chronic liver failure (ACLF). In one embodiment, a patient is suffering from acute liver failure. In one embodiment, a patient is suffering from chronic liver failure. In one embodiment, the liver failure is caused by a disease or condition selected from alcoholic liver disease, chronic viral hepatitis type C, chronic viral hepatitis type B, chronic bile duct blockage, Wilson's disease, hemochromatosis, exposure to drug and toxins, autoimmune hepatitis, cystic fibrosis, alpha antitrypsin deficiency, obesity or schistosomiasis.

In one embodiment, an active compound disclosed herein is administered in combination with an antibiotic for the prevention or treatment of bacterial infections. Examples of antibiotics include, but are not limited to, cefotaxime (Claforan), ofloxacin (Floxin), norfloxacin (Noroxin) or trimethoprim/sulfamethoxazole (Bactrim, Septra).

7. Anti-Platelet Agents

In another embodiment, a compound described herein is used in the treatment of blot clot (thrombus) formation in a host in need thereof. In one embodiment, the host is suffering from coronary artery disease, peripheral vascular disease, or cerebrovascular disease. In one embodiment, a compound described herein is administered to a host prior to any medical or surgical procedure in which diminished coagulation potential is desirable. In one embodiment, an active compound disclosed herein is administered in combination with another anti-thrombotic or anti-clotting agent.

In one embodiment, a compound of Formula I, II, or III, or another compound, as described herein, is provided for use in treating blot clot (thrombus) formation in a subject in need thereof, comprising administering an active compound as described herein, or a pharmaceutically acceptable composition, salt, isotopic analog, or prodrug thereof. In one embodiment, the compound for use in treating blot clot (thrombus) formation in a subject in need thereof is UNC4214, including a pharmaceutically acceptable composition, salt, isotopic analog or prodrug thereof.

In one embodiment, the treatment of blood clot formation is in, for example, a subject with coronary artery disease, peripheral vascular disease, or cerebrovascular disease, or the treatment is given prior to any medical or surgical procedure in which diminished coagulation potential is desirable. Coronary artery disease includes, for example, any coronary dysfunction (pathological state) resulting from coronary artheroscleroesis, i.e. partial or total occlusion of coronary vessels. The term also includes a range of various acute and chronical pathological states comprising stable and unstable angina pectoris (SAP and UAP, respectively), left ventricular dysfunction LVD, (congestive) heart failure CHF, myocardial death. Peripheral vascular disease includes, for example, occlusive or functional peripheral arterial disease (PAD). Examples of occlusive PAD include peripheral arterial occlusion, which may be acute, and Buerger's disease (thomboangiitis obliterans). Examples of functional PAD include Raynaud's disease, Raynaud's phenomenon, and acrocyanosis. Cerebrovascular disease includes, for example, any abnormality of the brain resulting from a pathologic process of a blood vessel. In one embodiment, the cerebrovascular disease is selected from cerebral ischemia, cerebral hemorrhage, ischemic stroke, hemorrhagic stroke, or ischemic reperfusion injury resulting from reintroduction of blood flow following cerebral ischemia or ischemic stroke. In one non-limiting embodiment, the medical or surgical procedure is pulmonary vein ablation.

In one embodiment, the treatment of blood clot formation is in a host having thrombi in blood vessels from pathologies or treatments including, for example, myocardial infarction, unstable angina, atrial fibrillation, stroke, renal damage, percutaneous translumenal coronary angioplasty, athreosclerosis, disseminated intravascular coagulation, sepsis, endotoxemia (i.e., the presence of endotoxins in the blood), pulmonary embolism and deep vein thrombosis. In one embodiment, the compounds described herein are administered to a host having blood clots on the surfaces of artificial organs, shunts and prostheses (for example, artificial heart valves that are implanted into a patient), and in patients that have received an intracoronary stent. In one embodiment, a host is administered an effective amount of a compound described herein due to the formation of clots resulting from some pathological conditions (for example, genetic mutation of VWF cleaving protease, ADAMT13), which may cause spontaneous binding of VWF to platelets resulting in formation of microthrombi in blood vessels leading to thrombotic thrombocytopenic purpura and other microangiopathy. Microangiopathy is a disease of blood vessels in which the walls of very small blood vessels (capillaries) become so thick and weak that they bleed, leak protein, and slow the flow of blood. In one embodiment, the treatment is in a patient with hemolytic uremic syndrome.

In one embodiment, an active compound disclosed herein is administered in combination with an additional anti-platelet agent. Examples of anti-platelet agents include, but are not limited to, aspirin, tirofiban (Aggrastat), Aggrenox, Agrylin, triflusal (Disgren), Flolan, eptifibatide (Integrilin), dipyridamole (Presantine), cilostazol (Pletal), abciximab (ReoPro), and Terutroban. In one embodiment, UNC4214A is administered in combination with an additional anti-platelet agent. In one embodiment, the Mer TKI and the additional anti-platelet agent act synergistically. In one embodiment, the use of a Mer TKI in combination with an additional anti-platelet agent provides for increased anti-thrombotic or anti-clotting effects without an increase in the standard of care dosage.

In one embodiment, the additional anti-platelet agent is an adenosine diphosphate (ADP) receptor inhibitor. Examples of ADP receptor inhibitors include, but are not limited to, clopidogrel (Plavix), prasugrel (Effient), ticagrelor (Brilinta), ticlopidine (Ticlid), N6-methyl-2'-deoxyadenosine-3', 5'-bisphosphate (MRS2179; $P_2Y1$ inhibitor), and 2-methylthioadenosine 5'-monophosphate triethylammonium salt (2-Me-SAMP; $P_2Y12$ inhibitor).

In one embodiment, an active compound disclosed herein is administered in combination with multiple anti-platelet agents. In one non-limiting embodiment, an active compound disclosed herein is administered in combination with N6-methyl-2'-deoxyadenosine-3',5'-bisphosphate and 2-methylthioadenosine 5'-monophosphate triethylammonium salt.

In one embodiment, an active compound disclosed herein is administered in combination with an anti-coagulant. In one embodiment, the anti-coagulant is a heparin composition. In one embodiment, the heparin composition is a low molecular weight heparin composition. Low molecular weight heparin compositions are well known to those of skill in the art and include, but are not limited to, tinzaparin, certoparin, pamaparin, nadroparin, ardeparin, enoxaparin, reviparin, dalteparin, and fraxiparin. Additional examples of anti-coagulants include, but are not limited to, warfarin (Coumadin), Fragmin, Hep-Lock, Lovenox, and Miradon. In one embodiment, UNC4214A is administered in combination with an anti-coagulant.

8. Nanoparticle Compositions or Carriers

In one aspect of the present invention, an effective amount of an active compound as described herein is incorporated into nanoparticles, e.g. for convenience of delivery and/or extended release delivery. The use of materials in nanoscale provides one the ability to modify fundamental physical properties such as solubility, diffusivity, blood circulation half-life, drug release characteristics, and immunogenicity. In the last two decades, a number of nanoparticle-based therapeutic and diagnostic agents have been developed for the treatment of cancer, diabetes, pain, asthma, allergy, and infections. These nanoscale agents can provide more effective and/or more convenient routes of administration, lower therapeutic toxicity, extend the product life cycle, and ultimately reduce health-care costs. As therapeutic delivery systems, nanoparticles allow targeted delivery and controlled release.

In addition, nanoparticle-based drug delivery can be used to release drugs at a sustained rate and thus lower the frequency of administration, deliver drugs in a target manner to minimize systemic side effects, or deliver two or more drugs simultaneously for combination therapy to generate a synergistic effect and suppress drug resistance. To date, a number of nanotechnology-based therapeutic products have been approved for clinical use. Among these products, liposomal drugs and polymer-based conjugates account for more than 80% of the products. See, Zhang, L., et al., Nanoparticles in Medicine: Therapeutic Applications and Developments, Clin. Pharm. and Ther., 83(5):761-769, 2008.

Optimal solid lipid nanoparticles (SLN) can be produced in a controlled fashion when a fraction of lipid in the crystalline alpha form can be created and preserved. By doing this, the SLN carrier has a built in trigger mechanism as lipids transform from the alpha to beta form and consequently control drug release. Drug release profiles can be modified according to the composition of the lipid matrix, surfactant concentration and production parameters. See, Muller, R. H., et al., Solid lipid nanoparticles (SLN) for controlled drug delivery—a review of the state of the art, Eur. H. Pharm. Biopharm., 50:161-177, 2000. Consien et al. have recently disclosed lipid nanoparticles having novel amino-lipids that form lipid nanoparticles and their use for the intracellular delivery of biologically active compounds, e.g., nucleic acids. See, U.S. Pat. No. 8,691,750 to Consien et al.

In regard to controlled release, Kanwar has recently disclosed alginate adsorbed chitosan adsorbed lactoferrin adsorbed calcium phosphate nanoparticles and the controlled release of lactoferrin from the nanoparticles. See, WO 2012/145801 to Kanwar. In addition, Armes et al. have recently disclosed polymer-templated core-shell nanoparticles adapted to facilitate controlled release of at least one active agent into a system in response to controlled changes in the pH of the system. See, U.S. Pat. No. 8,580,311 to Armes, S. et al. incorporated by reference herein.

Petros and DeSimone have recently reviewed strategies in the design of nanoparticles. In addition, the authors reviewed their PRINT (particle replication in non-wetting templates) technology for generating microparticles and nanoparticles. See, Petros, R. A. and DeSimone, J. M., Strategies in the design of nanoparticles for therapeutic applications, Nature Reviews/Drug Discovery, vol. 9:615-627, 2010. Importantly, the authors disclosed the production of nanoparticles in which a single parameter (shape or size) can be altered independently of all other particle attributes. The authors concluded their paper by outlining several particle characteristics that have emerged as being central to the function of engineered nanoparticles. These parameters include particle size, particle shape, surface characteristics and the ability to release therapeutics. Additional nanoparticle fabrication methods can also be found in U.S. Pat. No. 8,465,775, U.S. Pat. No. 8,444,899, U.S. Pat. No. 8,420,124, U.S. Pat. No. 8,263,129, U.S. Pat. Nos. 8,158,728 and 8,268,446 all hereby incorporated by reference.

Nanoparticles may be prepared using a wide variety of methods known in the art. For example, nanoparticles can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)).

In some embodiments, the compounds described herein are associated with a nanoparticle, such as a polymeric nanoparticle. Nanoparticles may comprise natural polymers, including but not limited to chitosan, alginate, dextran, gelatin, and albumin, and synthetic polymers such as, but not limited to, poly(lactide-co-glycolide) (PLGA), (3-hydroxybutyrate-co-3-hydroxyvalerate) (PHBV), poly(sebacic anhydride), poly(s-caprolactone), polystyrene, thermoresponsive (i.e., NIPAAm and CMCTS-g-PDEA) and pH-responsive (i.e., Eudragit L100, Eudragit S and AQOAT AS-MG) polymers.

In one embodiment, the polymeric particle is between about 0.1 nm to about 10000 nm, between about 1 nm to about 1000 nm, between about 10 nm and 1000 nm, between about 100 nm and 800 nm, between about 400 nm and 600 nm, or about 500 nm. In one embodiment, the microparticles are about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In one embodiment, the compounds described herein are covalently coupled to a polystyrene particle, PLGA particle, PLA particle, or other nanoparticle.

In some embodiments, the nanoparticle can be solid or hollow and can comprise one or more layers. In some embodiments, each layer has a unique composition and unique properties relative to the other layer(s). To give but one example, the nanoparticle may have a core/shell structure, wherein the core is one layer (e.g. a polymeric core) and the shell is a second layer (e.g. a lipid bilayer or monolayer). In some embodiments, the nanoparticle may comprise a plurality of different layers. In some embodiments, the compounds described herein can be incorporated into or surrounded by one or more layers.

In some embodiments, the nanoparticles comprising the compounds described herein may optionally comprise one or more lipids. In some embodiments, a nanoparticle may comprise a liposome. In some embodiments, a nanoparticle may comprise a lipid bilayer. In some embodiments, a nanoparticle may comprise a lipid monolayer. In some embodiments, a nanoparticle may comprise a micelle. In some embodiments, a nanoparticle may comprise a core comprising a polymeric matrix surrounded by a lipid layer (e.g., lipid bilayer, lipid monolayer, etc.). In some embodiments, a nanoparticle may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In other embodiments, the nanoparticle may comprise metal particles, quantum dots, ceramic particles, etc. In some embodiments, a non-polymeric nanoparticle is an aggregate of non-polymeric components, such as an aggregate of metal atoms (e.g., gold atoms).

In some embodiments, nanoparticles may optionally comprise one or more amphiphilic entities. In some embodiments, an amphiphilic entity can promote the production of nanoparticles with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making nanoparticles useful in the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of nanoparticles to be used in accordance with the present invention.

In some embodiments, a nanoparticle may optionally comprise one or more carbohydrates. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan. In some embodiments, the nanoparticle does not comprise (or specifically exclude) carbohydrates, such as a polysaccharide. In certain embodiments, the carbohydrate may comprise a carbohydrate derivative such as a sugar alcohol, including but not limited to mannitol, sorbitol, xylitol, erythritol, maltitol, and lactitol.

In some embodiments, the associated nanoparticle can comprise one or more polymers. In some embodiments, the nanoparticle comprises one or more polymers that are a non-methoxy-terminated, pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the nanoparticles are non-methoxy-terminated, pluronic polymers. In some embodiments, all of the polymers that make up the nanoparticle are non-methoxy-terminated, pluronic polymers. In some embodiments, the nanoparticle comprises one or more polymers that are a non-methoxy-terminated polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the nanoparticles are non-methoxy-terminated polymers. In some embodiments, all of the polymers that make up the nanoparticle are non-methoxy-terminated polymers. In some embodiments, the nanoparticle comprises one or more polymers that do not comprise pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the nanoparticle do not comprise pluronic polymer. In some embodiments, all of the polymers that make up the nanoparticles do not comprise pluronic polymer. In some embodiments, such a polymer can be surrounded by a coating layer (e.g., liposome, lipid monolayer, micelle, etc.). In some embodiments, various elements of the nanoparticle can be coupled with the polymer.

Other examples of polymers include, but are not limited to polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g. poly((β-hydroxyalkanoate))), poly (orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly (ethylene imine)-PEG copolymers.

In some embodiments, nanoparticles include polymers which have been approved for use in humans by the U.S. Food and Drug Administration (FDA) under 21 C.F.R. §177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a nanoparticles comprising a hydrophilic polymeric matrix generates a hydrophilic environment within the nanoparticle. In some embodiments, polymers can be hydrophobic. In some embodiments, a nanoparticles comprising a hydrophobic polymeric matrix generates a hydrophobic environment within the nanoparticle. Selection of the hydrophilicity or hydrophobicity of the polymer may have an impact on the nature of materials that are incorporated (e.g., coupled) within the nanoparticle.

In some embodiments, polymers may be modified with one or more moieties and/or functional groups. A variety of moieties or functional groups can be used in accordance with the present invention. In some embodiments, polymers may be modified with polyethylene glycol (PEG), with a carbohydrate, and/or with acyclic polyacetals derived from polysaccharides (Papisov, 2001, ACS Symposium Series, 786:301). Certain embodiments may be made using the general teachings of U.S. Pat. No. 5,543,158 to Gref et al., or WO publication WO2009/051837 by Von Andrian et al.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly (amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines. In embodiments, the nanoparticles may not comprise (or may exclude) cationic polymers.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

Polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used without undergoing a cross-linking step. It is further to be understood that a nanoparticle may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

The compounds of the present invention can be coupled to a nanoparticle by any of a number of methods. Generally, the coupling can be a result of bonding between the compound and the nanoparticle. This bonding can result in the compound being attached to the surface of the nanoparticle and/or contained within (encapsulated) the nanoparticle. In some embodiments, however, the compounds are encapsulated by the nanoparticle as a result of the structure of the nanoparticle rather than bonding to the nanoparticle. In some embodiments, the nanoparticle comprises a polymer as provided herein, and the compounds described herein are coupled to the nanoparticle. The compounds described herein may be encapsulated into nanoparticles as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly (Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010). Other methods suitable for encapsulating the compounds described herein may be used, including without limitation methods disclosed in U.S. Pat. No. 6,632,671 to Unger Oct. 14, 2003.

In certain embodiments, nanoparticles are prepared by a nanoprecipitation process or spray drying. Conditions used in preparing nanoparticles may be altered to yield particles of a desired size or property (e.g., hydrophobicity, hydrophilicity, external morphology, "stickiness," shape, etc.). The method of preparing the nanoparticles and the conditions (e.g., solvent, temperature, concentration, air flow rate, etc.) used may depend on the materials to be coupled to the nanoparticles and/or the composition of the polymer matrix. If particles prepared by any of the above methods have a size range outside of the desired range, particles can be sized, for example, using a sieve.

In one embodiment of the present invention, PRINT technology is used to manufacture nanoparticles comprising a compound described herein.

In another embodiment, provided herein are liposome based nanoparticles comprising a compound described herein. In another embodiment, a liposome based nanoparticle comprises a compound described herein formulated for controlled-release.

In one embodiment, provided herein are polymer based nanoparticles comprising a compound described herein. In another embodiment, provided herein are polymer based nanoparticles comprising a compound described herein formulated for controlled-release.

In one embodiment, nanoparticles are comprised of albumin and a compound described herein. In another embodiment, nanoparticles are comprised of a polysaccharide and a compound described herein. In one embodiment, nanoparticles are comprised of a metal and a compound described herein. In another embodiment, nanoparticles are comprised of gold and a compound described herein. In another embodiment, nanoparticles are comprised of iron oxide and a compound described herein. In one embodiment, nanoparticles are comprised of silicon and a compound described herein.

In regard to polymers used for the production of nanoparticles, several reviews are available. See, for example, Soppimath, K. S., et al., Biodegradable polymeric nanoparticles as drug delivery devices, J. Controlled Release, 70:1-20, 2001, Agnihotri, S. A., et al., Recent advances on chitosan-based micro- and nanoparticle delivery, J. Controlled Release, 100(1):5-28, 2004, Ganta, S, et al., A review of stimuli-responsive nanocarriers for drug and gene delivery, J. Controlled Release, 126(3):187-204, 2008, Danhier, F. et al., PLGA-based nanoparticles: An overview of biomedical applications, J. Controlled Release, 161(2):505-522, 2012, In one embodiment, nanoparticles are comprised of L-glutamic acid copolymers and a compound described herein. In another embodiment, nanoparticles are comprised of L-alanine copolymers and a compound described herein. In one embodiment, nanoparticles are comprised of L-lysine copolymers and a compound described herein. In another embodiment, nanoparticles are comprised of L-tyrosine copolymers and a compound described herein. In other embodiment, nanoparticles are comprised of poly(lactic-co-glycolic acid) and a compound described herein. In another embodiment, nanoparticles are comprised of methoxy-PEG-poly(D,L-lactide) and a compound described herein. In another embodiment, nanoparticles are comprised of HPMA copolymer and a compound described herein. In one embodiment, nanoparticles are comprised of polycyclodextran and a compound described herein. In one embodiment, nanoparticles are comprised of polyglutamate and a compound described herein. In another embodiment, nanoparticles are comprised of poly(iso-hexyl-cyanoacrylate) and a compound described herein. In one embodiment, nanoparticles are comprised of poly-L-lysine and a compound described herein. In another embodiment, nanoparticles are comprised of PEG and a compound described herein. In one embodiment, nanoparticles are made of combinations of polymers and a compound described herein.

In one embodiment, a compounds described herein is released from a nanoparticle over a period of between about 1 and about 90 days. In one embodiment, the compound is released over a period of about 3 to 28 days. In one embodiment, the compound is released over a period of about 5 to 21 days.

EXAMPLES

The present invention is explained in greater detail in the following non-limiting Examples.

Example 1

Syntheses of Active Compounds

General Schemes

Scheme 1 illustrates a general procedure for preparing a compound of the present invention. Structure 1-1 can be prepared by oxiding a desired 6-methylthio-1H-pyrazolo[3,4-d]pyrimidine with a desired oxiding agent according to methods known in the art. For example, Structure 1-1 can be prepared by treating a 6-methylthio-1H-pyrazolo[3,4-d]pyrimidine with a desired oxidizing agent, for example, 3-chloroperbenzoic acid in the presence of an organic solvent, for example, tetrahydrofuran. It should be noted that LG is a leaving group. In one embodiment, the leaving group is bromide. Structure 1-2 can be prepared by aminating a desired sulfone, 1-1, with a desired amine in an organic solvent, for example, tetrahydrofuran, in the presence of a base, for example, diisopropylethylamine optionally at an elevated temperature. In Step 2, the amine reagent can be a chiral amine and can be prepared by those skilled in the art. See, for example, March, J., Advanced Organic Chemistry: Reactions, Mechanisms and Structure, $3^{rd}$ Ed., New York, John Wiley and Sons, Inc., 1985; Nugent, T. C. and El-Shazly, M., "Chiral Amine Synthesis—Recent Developments and Trends for Enamide Reduction, Reductive Amination and Imine Reduction", *Advanced Synthesis and Catalysis"*, 352:753-819, 2010. Structure 1-3 can be prepared by treating a desired 1H-pyrazolo[3,4-d]pyrimidine with a desired $R^2$-$LG_1$ in the presence of a base and an organic solvent optionally in a microwave apparatus at an elevated temperature. For example, Structure 1-3 can be prepared by treating a 1H-pyrazolo[3,4-d]pyrimidine with an alkyl halide, $R^2$-$LG_1$, in the presence of a base, for example, potassium carbonate, and an organic solvent, for example, N,N-dimethylacetamide in a microwave apparatus at an elevated temperature, for example, at about 150° C. In one embodiment, $LG_1$ is a halide. In one embodiment, $LG_1$ is chloride. A compound of Formula I can be prepared by treating Structure 1-3, having a leaving group LG, with a borane reagent, an organometallic reagent, a base, a solvent(s) in a microwave apparatus optionally at an elevated temperature. For example, a compound of Formula I can be prepared by treating a compound with a leaving group, for example, a halide, with a borane reagent, for example, 1-methyl-4-(4-(4,4,5,5-tetramethyl-1,3,2-dioxaborolan-2-yl)benzyl)-1,4-diazepane, an organometallic reagent, for example, tetrakis(triphenylphosphine)palladium (0), a base, for example, potassium carbonate in a solvent(s) optionally at an elevated temperature. In one embodiment, the solvents are dioxane and water. In one embodiment, the reaction is carried out in a microwave apparatus at about 150° C. It will also be appreciated by those skilled in the art that other leaving groups can be used at the six-position of a 1H-pyrazolo[3,4-d]pyrimidine to generate compounds of Formula I. This chemistry is illustrated in Scheme 1.

Scheme 2 illustrates a general procedure for preparing a compound of the present invention. Structure 2-1 can be prepared by oxiding a desired 6-methylthio-1H-pyrazolo[3,4-d]pyrimidine with a desired oxiding agent according to methods known in the art. For example, Structure 2-1 can be prepared by treating a 6-methylthio-1H-pyrazolo[3,4-d]pyrimidine with a desired oxidizing agent, for example, 3-chloroperbenzoic acid in the presence of an organic solvent, for example, tetrahydrofuran. It should be noted that LG is a leaving group. In one embodiment, the leaving group is bromide. Structure 2-2 can be prepared by aminating a desired sulfone, 2-1, with a desired amine in an organic solvent, for example, tetrahydrofuran, in the presence of a base, for example, diisopropylethylamine optionally at an elevated temperature. In Step 2, the amine reagent can be a chiral amine that can be prepared by those skilled in the art. See, for example, March, J., Advanced Organic Chemistry: Reactions, Mechanisms and Structure, $3^{rd}$ Ed., New York, John Wiley and Sons, Inc., 1985; Nugent, T. C. and El-Shazly, M., "Chiral Amine Synthesis—Recent Developments and Trends for Enamide Reduction, Reductive Amination and Imine Reduction", *Advanced Synthesis and Catalysis*", 352:753-819, 2010. Structure 1-3 can be prepared by treating a desired 1H-pyrazolo[3,4-d]pyrimidine with a desired $R^{12}$-$LG_1$ in the presence of a base and an organic solvent optionally in a microwave apparatus at an elevated temperature. For example, Structure 2-3 can be prepared by treating a 1H-pyrazolo[3,4-d]pyrimidine with an alkyl halide, $R^{12}$-$LG_1$, in the presence of a base, for example, potassium carbonate, and an organic solvent, for example, N,N-dimethylacetamide in a microwave apparatus at an elevated temperature, for example, at about 150° C. In one embodiment, $LG_1$ is a halide. In one embodiment, $LG_1$ is chloride. A compound of Formula II can be prepared by treating Structure 2-3, having a leaving group LG, with a borane reagent, an organometallic reagent, a base, and a solvent(s) in a microwave apparatus optionally at an elevated temperature. For example, a compound of Formula II can be prepared by treating a compound with a leaving group, for example, a halide, with a borane reagent, for example, 1-methyl-4-(4-(4,4,5,5-tetramethyl-1,3,2-dioxaborolan-2-yl)benzyl)-1,4-diazepane, an organometallic reagent, for example, tetrakis(triphenylphosphine)palladium (0), a base, for example, potassium carbonate in a solvent(s) optionally at an elevated temperature. In one embodiment, the solvents are dioxane and water. In one embodiment, the reaction is carried out in a microwave apparatus at about 150° C. It will also be appreciated by those skilled in the art that other leaving groups can be used at the six-position of a 1H-pyrazolo[3,4-d]pyrimidine to generate compounds of Formula II. This chemistry is illustrated in Scheme 2.

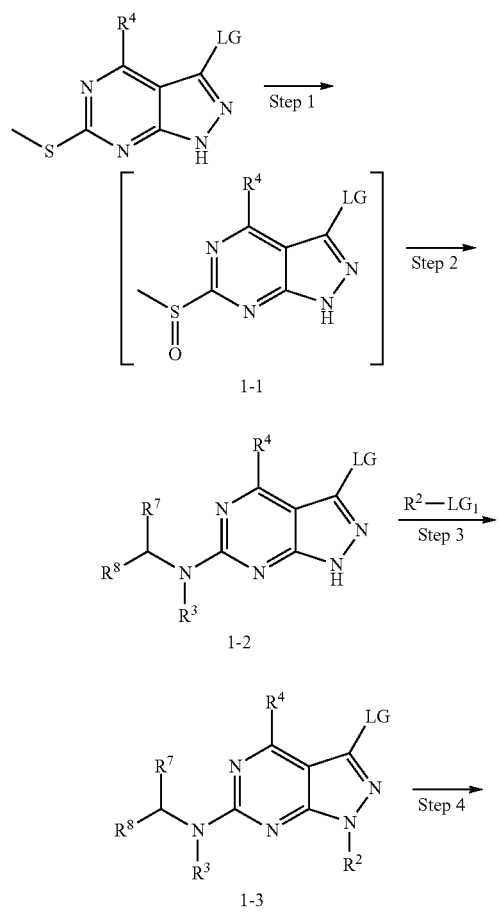

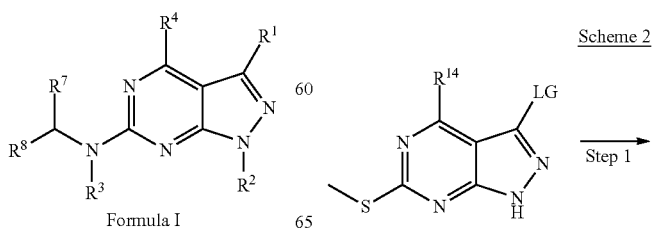

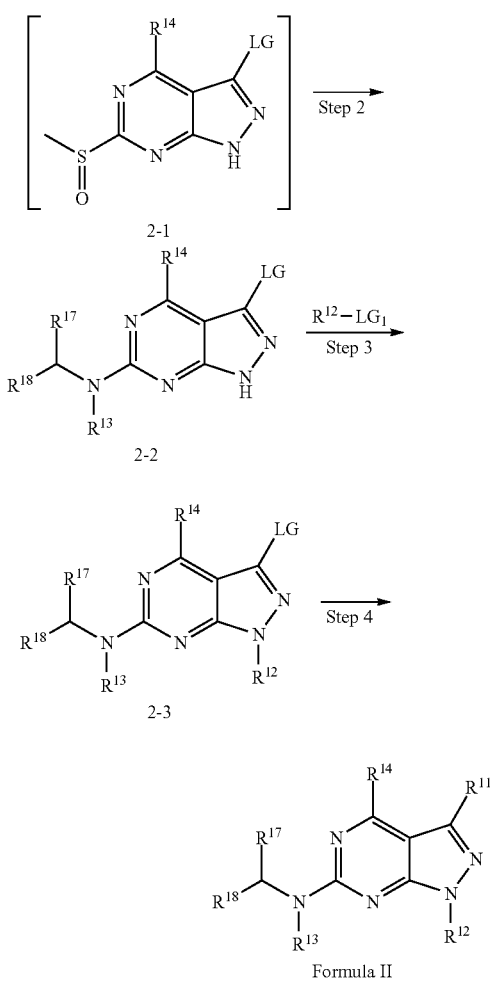

It should be noted that the chemistry disclosed in Schemes 1 and 2 can be used to prepare compounds of Formula III.

It should also be noted that the amine reagent used in the preparation of compounds of Formula III can be chiral and can be prepared by those skilled in the art. See, for example, March, J., Advanced Organic Chemistry: Reactions, Mechanisms and Structure, 3$^{rd}$ Ed., New York, John Wiley and Sons, Inc., 1985; Nugent, T. C. and El-Shazly, M., "Chiral Amine Synthesis—Recent Developments and Trends for Enamide Reduction, Reductive Amination and Imine Reduction", *Advanced Synthesis and Catalysis"*, 352:753-819, 2010.

Compounds of Formula I, Formula II or Formula III can be metabolized to generate pyrazolopyrimidine compounds. In one embodiment, a compound of Formula I can be dealkylated. For example, a compound of Formula I can be dealkylated at $R^8R^7CHNR^3$ to generate an amine, $NH_2$. In one embodiment, a compound of Formula II can be dealkylated. For example, a compound of Formula II can be dealkylated at $R^{17}R^{18}CHNR^{13}$ to generate an amine, $NH_2$. In one embodiment, a compound of Formula III can be dealkylated. For example, a compound of Formula III can be dealkylated at $R^{20}R^{21}CHCH_2NR^{13}$ to generate an amine, $NH_2$. In one embodiment, a compound of Formula I, Formula II or Formula III comprising a methylated amine can be demethylated. In one embodiment, a compound of Formula I, Formula II or Formula III can be oxidized. For example, a compound of Formula I, Formula II or Formula III comprising a homopiperazine group can be oxidized to generate a homopiperazine N-oxide. In another embodiment, a compound of Formula I, Formula II or Formula III comprising a homopiperazine group can be oxidized twice to generate a homopiperazine bis-N-oxide. In another embodiment, a compound of Formula I, Formula II or Formula III can be oxidized to generate a pyrazolopyrimidine N-oxide. The metabolic pathways disclosed above are illustrated in Scheme 3 with the compound UNC4214A.

Scheme 3

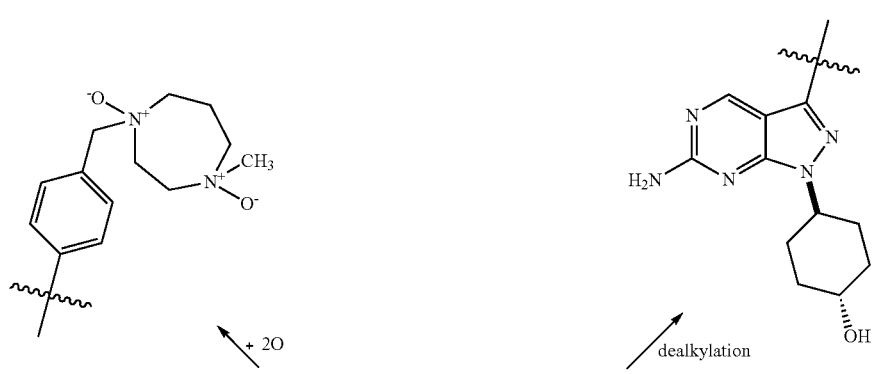

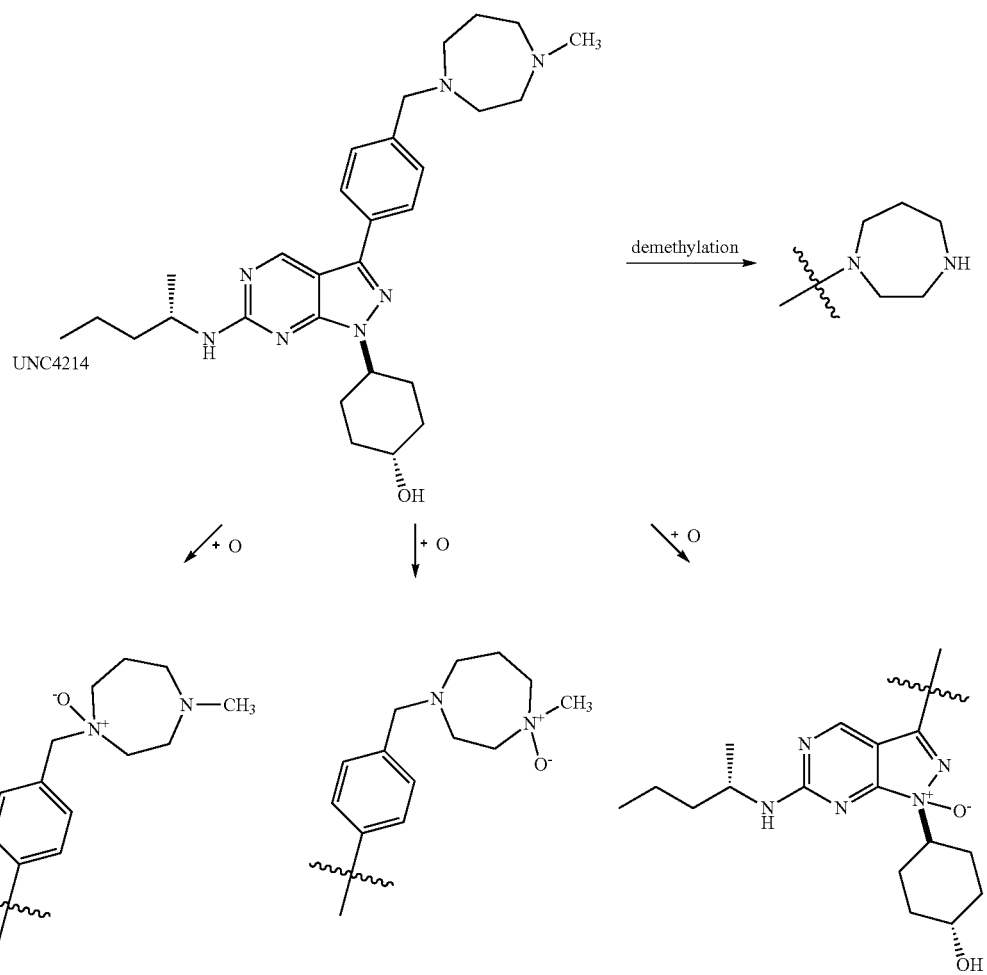
Example 2
trans-4-(3-(4-((4-Methyl-1,4-diazepan-1-yl)methyl)phenyl)-6-(((S)-pentan-2-yl)amino)-1H-pyrazolo[3,4-d]pyrimidin-1-yl)cyclohexan-1-ol
General Procedure A:
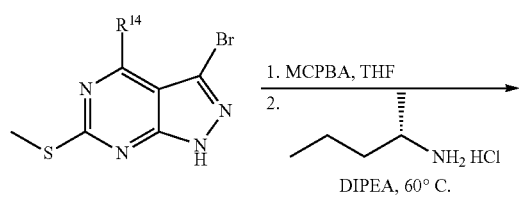
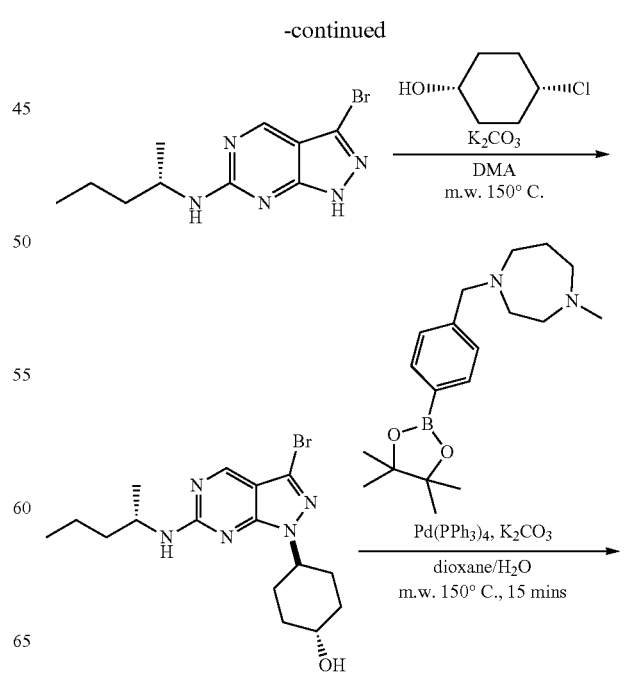

-continued

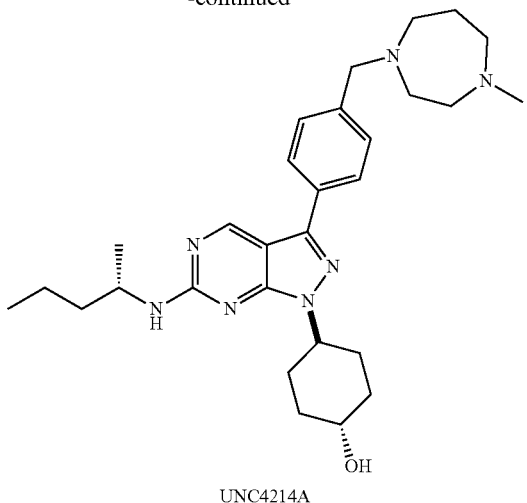

UNC4214A

A solution of 3-bromo-6-(methylthio)-1H-pyrazolo[3,4-d]pyrimidine (980 mg, 4.0 mmol) in THF (5.0 ml) was added 3-chloroperbenzoic acid (1.5 g, 6.0 mmol). The resulting mixture was stirred at room temperature for 2 h and (S)-pentan-2-amine hydrochloride (989 mg, 2.0 mmol) was added, followed by N,N-diisopropylethylamine (2.7 ml, 4.0 mmol). The mixture was stirred overnight at room temperature, then was diluted with EtOAc (10 ml) and washed with 1.0 N aqueous NaOH solution (10 ml), water (10 ml) and brine (10 ml). The organic layer was dried (Na$_2$SO$_4$) and concentrated to give (S)-3-bromo-N-(pentan-2-yl)-1H-pyrazolo[3,4-d]pyrimidin-6-amine (MS m/z 284.05 [M+1]$^+$), used as such in the next step.

A solution of (S)-3-bromo-N-(pentan-2-yl)-1H-pyrazolo[3,4-d]pyrimidin-6-amine (120 mg, 0.40 mmol) and 4-chlorocyclohexan-1-ol (161 mg, 1.2 mmol) in N,N-dimethylacetamide (0.50 ml) was added K$_2$CO$_3$ (218 mg, 1.6 mmol). The resulting mixture was stirred at 150° C. under microwave irradiation for 1.5 h. The reaction was quenched with water (1.0 ml) and the aqueous layer was extracted with EtOAc (1.0 ml×3). The combined organic layer was washed with brine (2.0 ml), dried (Na$_2$SO$_4$) and concentrated to give trans-4-(3-bromo-6-(((S)-pentan-2-yl)amino)-1H-pyrazolo[3,4-d]pyrimidin-1-yl)cyclohexan-1-ol (MS m/z 382.15 [M+1]$^+$). The crude product was used in the next step without further purification.

A solution of trans-4-(3-bromo-6-(((S)-pentan-2-yl)amino)-1H-pyrazolo[3,4-d]pyrimidin-1-yl)cyclohexan-1-ol (68 mg, 0.18 mmol) and 1-methyl-4-(4-(4,4,5,5-tetramethyl-1,3,2-dioxaborolan-2-yl)benzyl)-1,4-diazepane (88 mg, 0.27 mmol) in a mixture of dioxane and water (4:1, 0.50 ml) was added tetrakis(triphenylphosphine)palladium(0) (10.4 g, 0.01 mmol) and K$_2$CO$_3$ (50 mg, 0.36 mmol). The resulting mixture was stirred at 90° C. under microwave irradiation for 30 minutes. The reaction was quenched with water (1.0 ml) and the aqueous layer was extracted with EtOAc (1.0 ml×3). The combined organic layer was washed with brine (2.0 ml), dried (Na$_2$SO$_4$), and concentrated. The residue was purified on HPLC to provide the title compound as a TFA salt, which was converted to HCl salt with a 4.0 N HCl solution in dioxane and lyophilized to yield the HCl salt of the title compound UNC4214A (10 mg, 10%). $^1$H NMR (400 MHz, CD$_3$OD) δ 9.23 (s, 1H), 8.11 (d, J=8.0 Hz, 2H), 7.81 (d, J=8.0 Hz, 2H), 4.69-4.55 (m, 1H), 4.55 (s, 2H), 4.28-4.16 (m, 1H), 4.02-3.42 (m, 8H), 3.00 (s, 3H), 2.47-2.29 (m, 2H), 2.17-2.02 (m, 6H), 1.75-1.42 (m, 6H), 1.34 (d, J=8.0 Hz, 3H), 1.01 (t, J=8.0 Hz, 3H); MS m/z 506.35 [M+1]$^+$.

Table 1 describes compounds prepared following procedures described in Examples 1 to 2, using appropriate reagents.

| | Structure | Compound_ID | Mer IC$_{50}$ | Physical Data MS m/z (M + 1) or/and $^1$H NMR (400 MHz, CD$_3$OD) |
|---|---|---|---|---|
| 1 | 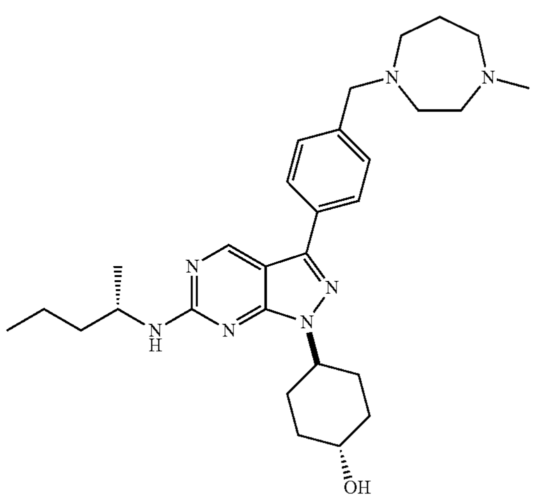 | UNC4214A | ++++ | $^1$H NMR (400 MHz, CD$_3$OD) δ 9.23 (s, 1H), 8.11 (d, J = 8.0 Hz, 2H), 7.81 (d, J = 8.0 Hz, 2H), 4.69-4.55 (m, 1H), 4.55 (s, 2H), 4.28-4.16 (m, 1H), 4.02-3.42 (m, 8H), 3.00 (s, 3H), 2.47-2.29 (m, 2H), 2.17-2.02 (m, 6H), 1.75-1.42 (m, 6H), 1.34 (d, J = 8.0 Hz, 3H), 1.01 (t, J = 8.0 Hz, 3H); MS m/z 506.35 [M + 1]$^+$. |

Table 1-continued
describes compounds prepared following procedures described in Examples 1 to 2, using appropriate reagents.
| Structure | Compound_ID | Mer IC$_{50}$ | Physical Data MS m/z (M + 1) or/and 1H NMR (400 MHz, CD$_3$OD) |
|---|---|---|---|
| 2 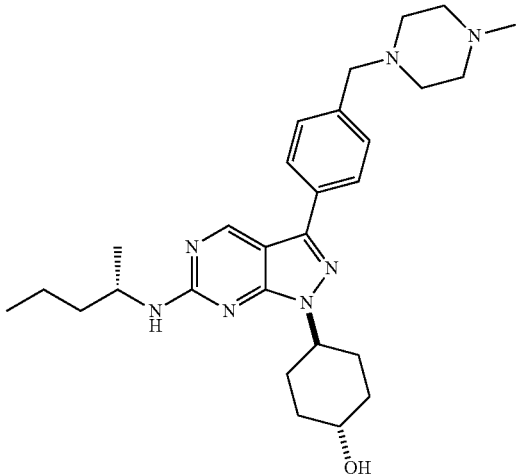 | | | |
| 3 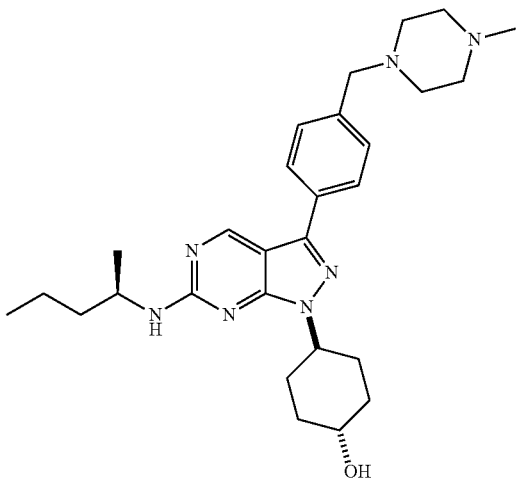 | | | |
| 4 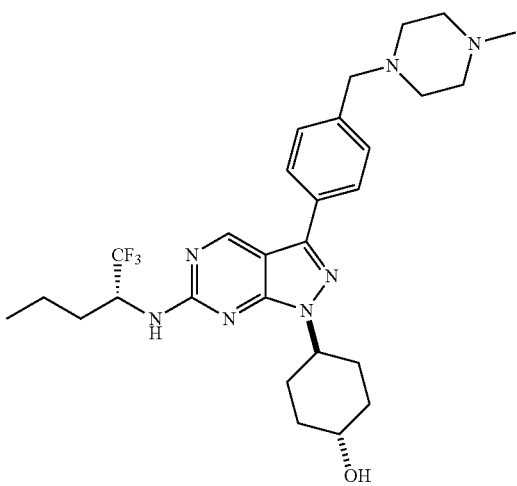 | | | |

Table 1-continued
describes compounds prepared following procedures described in Examples 1 to 2, using appropriate reagents.
| Structure | Compound_ID | Mer IC$_{50}$ | Physical Data MS m/z (M + 1) or/and 1H NMR (400 MHz, CD$_3$OD) |
|---|---|---|---|
5 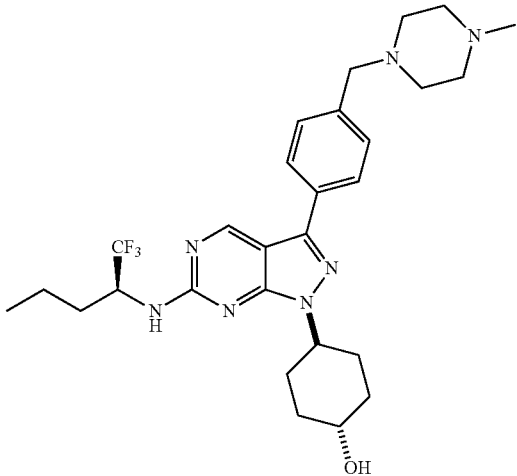
6 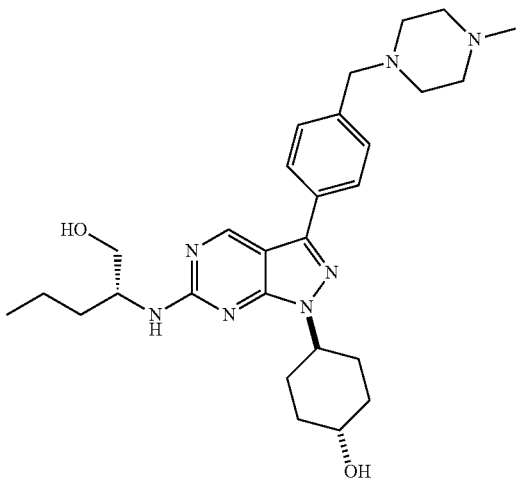
7 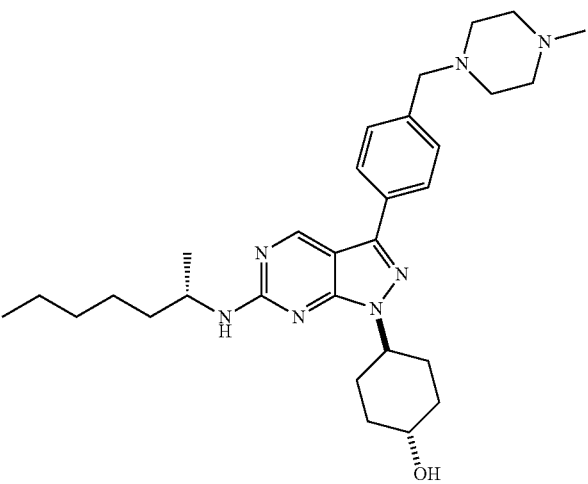

Table 1-continued describes compounds prepared following procedures described in Examples 1 to 2, using appropriate reagents.

| Structure | Compound_ID | Mer IC$_{50}$ | Physical Data MS m/z (M + 1) or/and 1H NMR (400 MHz, CD$_3$OD) |
|---|---|---|---|
| 8 | | | |
| 9 | | | |
| 10 | | | |

Table 1-continued
describes compounds prepared following procedures described in Examples 1 to 2, using appropriate reagents.
| Structure | Compound_ID | Mer IC$_{50}$ | Physical Data MS m/z (M + 1) or/and 1H NMR (400 MHz, CD$_3$OD) |
|---|---|---|---|
11
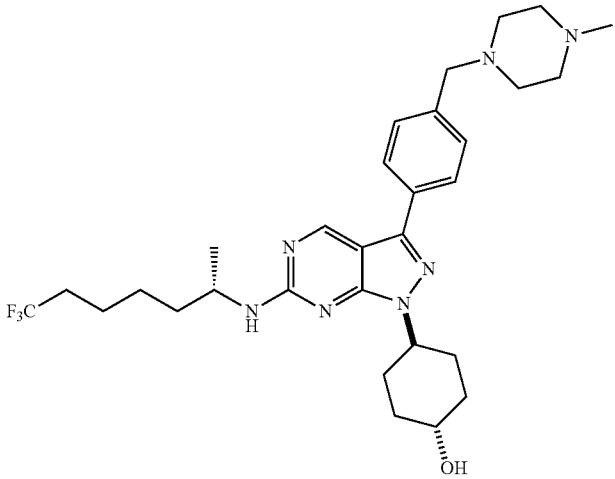
12
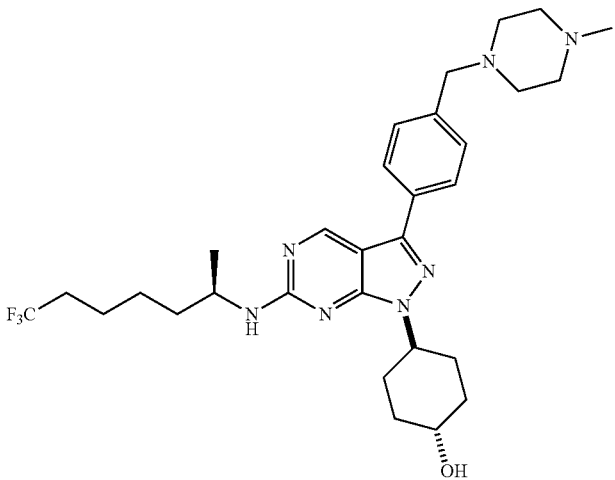
13
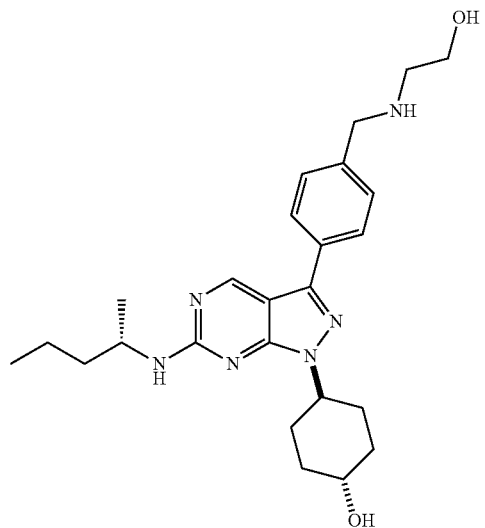

Table 1-continued
describes compounds prepared following procedures described in Examples 1 to 2, using appropriate reagents.
| Structure | Compound_ID | Mer IC$_{50}$ | Physical Data MS m/z (M + 1) or/and 1H NMR (400 MHz, CD$_3$OD) |
|---|---|---|---|
| 14 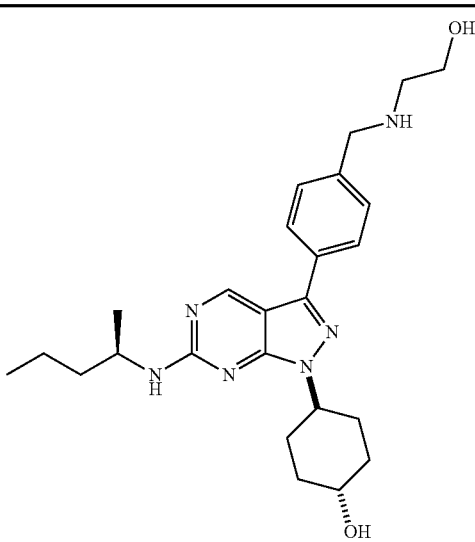 | | | |
| 15 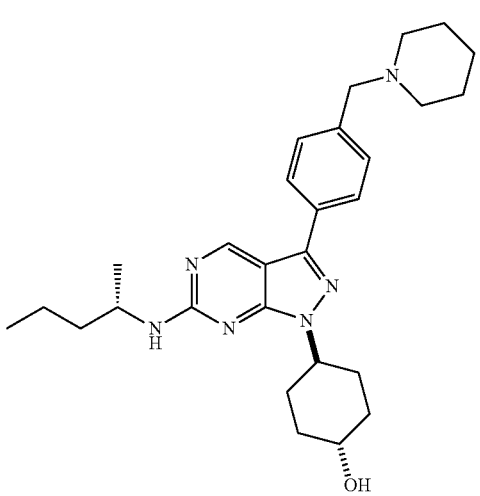 | | | |
| 16 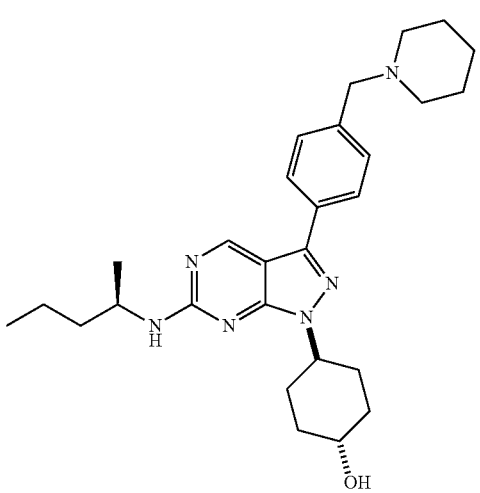 | | | |

US 9,603,850 B2
93                                                                 94
Table 1-continued
describes compounds prepared following procedures described in Examples 1 to 2, using appropriate reagents.
| Structure | Compound_ID | Mer IC$_{50}$ | Physical Data MS m/z (M + 1) or/and 1H NMR (400 MHz, CD$_3$OD) |
|---|---|---|---|
17
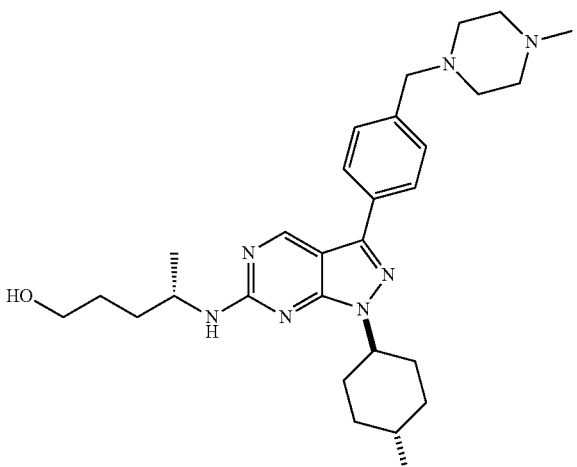
18
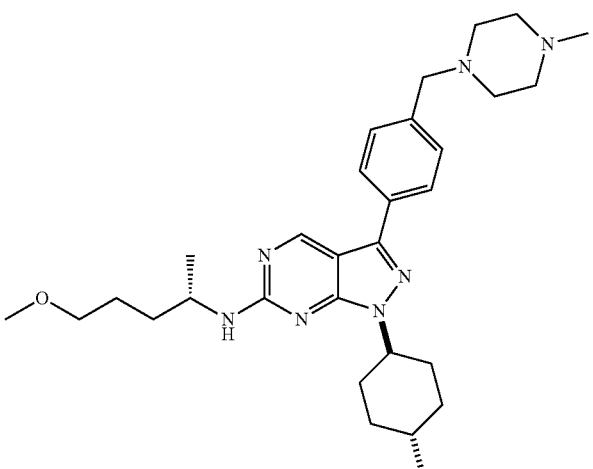
19
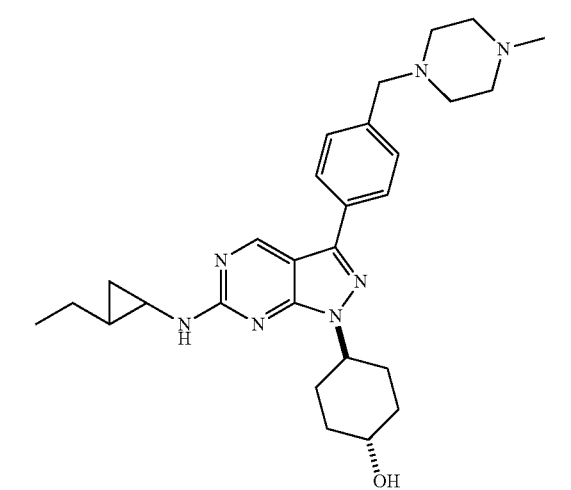

TABLE 1-continued
describes compounds prepared following procedures described in Examples 1 to 2, using appropriate reagents.
| Structure | Compound_ID | Mer IC$_{50}$ | Physical Data MS m/z (M + 1) or/and 1H NMR (400 MHz, CD$_3$OD) |
|---|---|---|---|
| 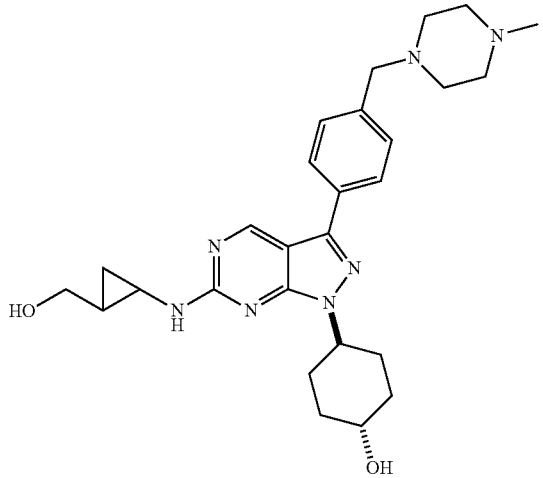 | 20 | | |
| 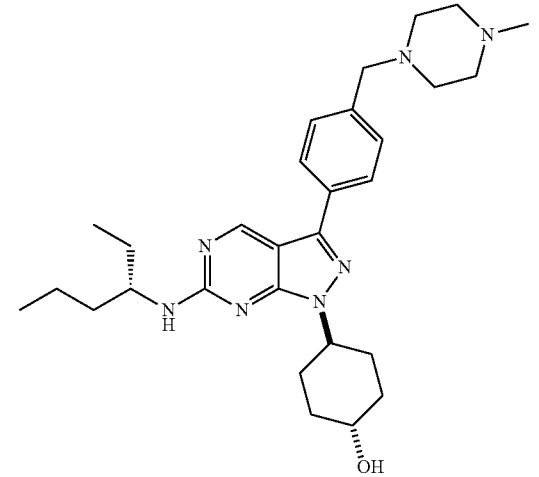 | 21 | | |
| 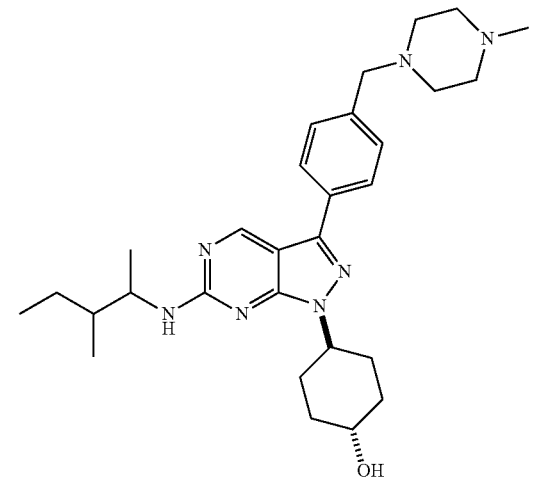 | 22 | | |

Table 1-continued describes compounds prepared following procedures described in Examples 1 to 2, using appropriate reagents.

| Structure | Compound_ID | Mer IC$_{50}$ | Physical Data MS m/z (M + 1) or/and 1H NMR (400 MHz, CD$_3$OD) |
|---|---|---|---|
| 23 (structure shown) | | | |

(Note:
MerTK IC50:
++++ means <10 nM;
+++ means between 10-100 nM,
++ means between 100 nM-1 µM;
+ means between 1-30 µM;
− means inactive.)

Example 3

Selectivity of Active Compounds for MerTK

Inhibition constants of MerTK, Flt3, Tyro3 and Axl kinase activity by an active compound as described herein is determined at the Km for ATP using a microfluidic capillary electrophoresis (MCE) assay in which phosphorylated and unphosphorylated substrate peptides were separated and analyzed using a LabChip EZ Reader. See, Liu J, et al. UNC1062, a new and potent MerTK inhibitor. Eur J Med Chem. 2013; 65:83-93; Liu J, et al. Discovery of novel small molecule MerTK kinase inhibitors for the treatment of pediatric acute lymphoblastic leukemia. ACS Med Chem Lett. 2012; 3:129-134; Pommereau A, Pap E, Kannt A. Two simple and generic antibody-independent kinase assays: comparison of a bioluminescent and a microfluidic assay format. J Biomol Screen. 2004; 9: 409-416; Dunne J, Reardon H, Trinh V, Li E, Farinas J. Comparison of on-chip and off-chip microfluidic kinase assay formats. Assay Drug Dev Technol. 2004; 2:121-129; Bernasconi P, Chen M, Galasinski S, Popa-Burke I, Bobasheva A, Coudurier L, Birkos S, Hallam R, Janzen W P. A chemogenomic analysis of the human proteome: application to enzyme families. J Biomol Screen. 2007; 12:972-982.

Briefly, activity assays were performed in a 384 well, polypropylene microplate in a final volume of 50 L of 50 mM Hepes, Ph 7.4 containing 10 mM MgCl$_2$, 1.0 mM DTT, 0.01% Triton X-100, 0.1% Bovine Serum Albumin (BSA), containing 1.0 µM fluorescent substrate and ATP at the Km for each enzyme. All reactions were terminated by addition of 20 µL of 70 mM EDTA. After a 180 min incubation, phosphorylated and unphosphorylated substrate peptides were separated in buffer supplemented with 1×CR-8 on a LabChip EZ Reader equipped with a 12-sipper chip. Data were analyzed using EZ Reader software.

Assay Conditions for MCE Assays

| Kinase | Peptide Substrate | Kinase (nM) | ATP (uM) |
|---|---|---|---|
| Mer | 5-FAM-EFPIYDFLPAKKK-CONH$_2$ | 2.0 | 5.0 |
| Axl | 5-FAM-KKKKEEIYFFF-CONH$_2$ | 120 | 65 |
| Tyro | 5-FAM-EFPIYDFLPAKKK-CONH$_2$ | 10 | 21 |

Compound UNC4214A, wherein R$^7$=methyl and R$^8$=propyl had an IC$_{50}$ of about 8.9 nM against MerTK, an IC$_{50}$=84 nM against Flt3, an IC$_{50}$=14 nM against Tyro3 and an IC$_{50}$ of about 201 nM against Axl. Compound UNC2025 (see pyrrolopyrimidine structure in background), wherein R$^7$=H and R$^8$=propyl had an IC$_{50}$ of about 0.7 nM against MerTK, an IC$_{50}$=0.8 nM against Flt3 and an IC$_{50}$ of about 17 nM against Axl. Pyrazolopyrimidine compound UNC1144A, wherein R$^7$=H and R$^8$=propyl had an IC$_{50}$ of about 0.7 nM against MerTK, an IC$_{50}$=0.67 nM against Flt3. Pyrazolopyrimidine compound UNC1150A, wherein R$^7$=H and R$^8$=propyl had an IC$_{50}$ of about 3.4 nM against MerTK, an IC$_{50}$=3.3 nM against Flt3. The structures of UNC1144A and UNC1150A are provided here for reference:

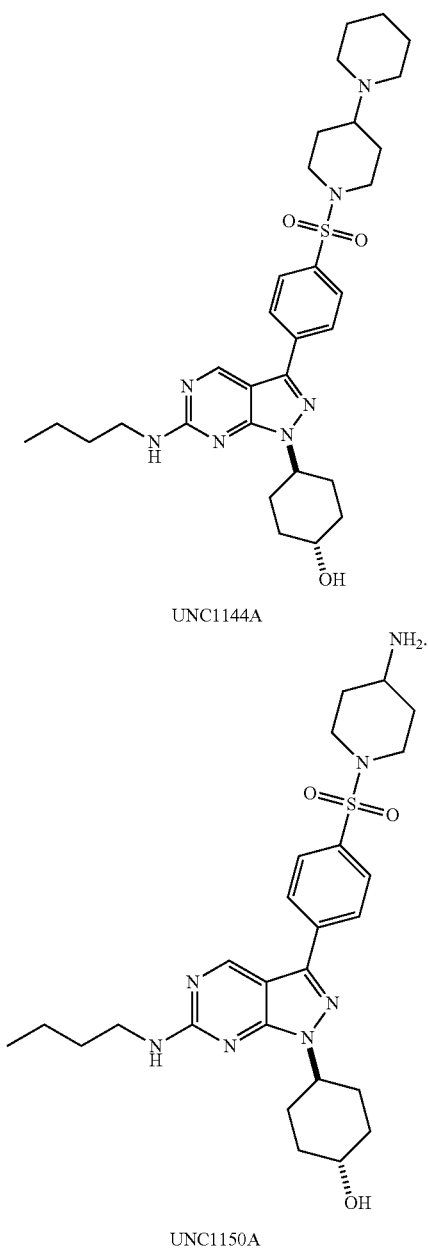

UNC1144A

UNC1150A

Thus, whereas UNC2025, UNC1144A, and UNC1150A had similar activities against MerTK and Flt3, UNC4214A has a selectivity in binding to MerTK over Flt3 by approximately 10 fold.

Example 4

Efficacy of a Novel Small Molecule MerTK Receptor Tyrosine Kinase Inhibitor in B-RAF Wild-Type and B-RAF Mutant Melanoma Cell A MERTK-selective small-molecule tyrosine kinase inhibitor (TKI) is evaluated in preclinical models of melanoma, both alone and in combination with vemurafenib (a mutant B-RAF TKI). B-RAF wild-type (HMCB) and B-RAF mutant (G361) cell lines are treated with Mer TKI or vehicle. Downstream signaling is evaluated by immunoblotting, and induction of apoptosis is determined by flow cytometry in cells stained with YO-PRO®-1 iodide and propidium iodide. Alternatively, cells are seeded in media containing Mer TKI or vehicle and colony formation is determined.

Example 5

Inhibition of Murine Melanoma Growth by a Small Molecule Mer Tyrosine Kinase Inhibitor (MER TKI)

In this example, the activity of a MerTK inhibitor is examined on tumor growth in autochthonous murine tumor models. Mer TKI is assessed in immune-competent, genetically engineered murine models (GEMMs). Activity is tested in RAS-driven, INK4a/Arf null melanoma GEMM (TRIA) mice. The efficacy of 15 chemotherapeutic and/or targeted regimens in a large (>220) cohort of TRIA mice has previously been tested (Clinical Cancer Research 18:5290, 2012). The overall response is 10% (partial responses and stable disease). There are no complete responses. A combination of MEK (AZD 6244) and PI3K/mTOR (BEZ235) inhibitors are the most active previous regimen (responses seen in 9/18 mice=50%, with 0 CRs) with moderate toxicity.

Example 6

Cell Killing by MER TKIs in Combination with FGFR Inhibition

In this study, the interaction between a novel MerTK-selective small molecule tyrosine kinase inhibitor (TKI) and AZD-4547, an FGFR TKI, in NSCLC cell lines is studied. Colo699 (MerTK+, FGFR+) and H226 (MerTK+, FGFR+) NSCLC cells are cultured for 14 days in soft agar in the presence of Mer TKI and/or AZD-4547, alone or in combination, and colonies are stained and counted. Changes in the activity of downstream signaling pathways, including PI3K/AKT, MEK/ERK, and STAT proteins are evaluated by immunoblotting.

Example 7

Inhibition of Mer Tyrosine Kinase with a Novel Small Molecule Inhibitor in Mouse Models of ALL In this example, preclinical testing of Mer TKIs as a potential therapy for MERTK-expressing ALL is disclosed. Mer TKI inhibition of phosphorylation/activation of MerTK is tested in 697 B-ALL cells. Mer TKIs are tested in several mouse models, including an orthotopic B-ALL xenograft model of minimal residual disease and a similar model of existent disease in which leukemia is established for 14 days prior to initiation of treatment. In both models, tumor burden is measured by bioluminescent imaging.

Example 8

Inhibition of Mer Tyrosine Kinase with a Novel Small Molecule Inhibitor in Pre-Clinical Models of Non-Small Cell Lung Cancer The effects of Mer TKI treatment on activation of MerTK and related members of the TAM-family of kinases, Axl and Tyro3, and effects on downstream proliferative and prosurvival signaling pathways are analyzed by immunoblot. In addition, Mer TKI-mediated anti-tumor activity is determined in a panel of NSCLC cell lines using soft-agar and clonogenic assays. Cells are stained with YoPro-1-iodide and propidium iodide dyes and induction of apoptosis is determined using flow cytometry. Finally, a subcutaneous murine xenograft model is employed to determine therapeutic effects in vivo.

Example 9

A Dual FLT-3 and Mer Tyrosine Kinase Small Molecule Inhibitor in Acute Myeloid Leukemia Cell Lines and Patient Samples FLT-3 and Mer tyrosine kinases have been previously identified as potential targets in the treatment of acute myeloid leukemia (AML). Expression of FLT-3 internal tandem duplication (ITD) occurs in ~30-40% of AML patient samples and MerTK overexpression has been detected in ~80-100%. In this example, a novel small molecule inhibitor is tested for activity against both of these kinases and the growth inhibition or apoptosis of cell lines and patient myeloblasts is examined. In these studies, the effects of treatment with MER-TKI are analyzed in FLT3-ITD-positive (Molm-13 and MV4; 11) and MERTK-positive (Kasumi-1 and U937) AML cell lines and in primary AML patient samples with variable expression of FLT3-ITD and MerTK. AML cell lines are also stained with Yo-Pro-1 iodide and propidium iodide and analyzed by flow cytometry to determine induction of apoptosis in response to treatment with Mer TKI. Primary patient samples that are MerTK and/or FLT3-ITD positive are analyzed in similar assays.

Example 10

Targeted Inhibition of Mer Tyrosine Kinase in the Tumor Microenvironment in a Mouse Model of Breast Cancer To further investigate the utility of MerTK inhibition in the tumor microenvironment as a therapeutic strategy, the efficacy of a Mer TKI is evaluated in immunocompetent C57Bl/6 mice implanted orthotopically with PyVmT mammary gland tumor cells. These PyVmT tumors cells do not express MerTK, AXL or TYRO3.

Example 11

Murine $FeCl_3$-Induced Carotid Artery Thrombosis Model 6-12-week old C57BL/6 mice (The Jackson Laboratory, Bar Harbor, Me.), are fed low-soy laboratory chow to prevent interactions from genistein, a phytoestrogen with tyrosine kinase inhibitor activity. Approximately equal numbers of male and female mice are used for all experiments to limit any potential skewing of results by sex-based differences in thrombosis. The mice are anesthetized with intraperitoneal sodium pentobarbital (60-90 mg·kg$^{-1}$ loading dose, 10 to 20 mg/kg$^{-1}$ maintenance dose as needed to maintain adequate anesthesia as measured by paw pressure response). The mice are then fixed in the supine position to a polycarbonate experimental platform under a dissecting microscope (Olympus SZ61 Infinity Lite, Olympus Equipment). A rectal temperature probe is used in conjunction with a heating pad to monitor and maintain temperature at 37±1° C. A 2 cm vertical midline ventral cervical incision is made to expose the trachea, which is then horizontally incised and cannulated with a rigid endotracheal tube (Harvard MiniVent type 845, Harvard Apparatus) secured with a 4-0 silk tie, and attached to a ventilator (Harvard MiniVent type 845, Harvard Apparatus), which delivered a 200 L stroke volume and 80 breaths per minute. The carotid artery is exposed by dissection, allowing for attachment of a microvascular ultrasonic flow probe (Transonic Flowprobe, Transonic Systems, Ithaca, N.Y.), and the cavity is flooded with NaCl to prevent tissue dehydration. A 1 mm×5 mm strip of Parafilm (Pechiney Plastic Packaging, Chicago, Ill.) is placed perpendicular to, and immediately posterior to, the artery to separate it from other cavity tissue. NaCl (negative control), Mer TKI (3 mg/kg in NaCL), 2 µM abciximab (positive control), HD ADPis in NaCl (3 mg/kg MRS2179+3 mg/kg 2-MeSAMP), LD ADPis (1.5 mg/kg MRS2179+1.5 mg/kg 2-MeSAMP), or a combination of Mer TKI and LD ADPis are injected and allowed to circulate for 30 minutes. The cavity is then dried and a 1.2 mm diameter circle of filter paper (Whatman Ltd, Chippenham, Wiltshire, UK) is saturated with 6% $FeCl_3$ (~60 µM, Fisher) for 10 seconds, and placed on the artery, proximal to the ultrasound probe, for 3 minutes to create the injury. Then, the Parafilm and filter paper are removed, the cavity is flooded with saline, and the flow probe readout is analyzed using LabChart software (AD Instruments, CO Springs, Colo.). Elapsed Time To First (initial) artery Occlusion (TTFO, mean blood flow of 0 mL/min flow for >30 seconds), and total Duration Of Occlusion time (DOO, mean blood flow <20% of pre-$FeCl_3$ baseline) is measured during the 60 minutes following $FeCl_3$ application. Values are expressed as mean+/−SEM, with significance determined by unpaired, two-tailed Student's t-test.

Example 12

Effects of FLT3 and MerTK Inhibitors on MerTK Phosphorylation and Downstream Signaling in Acute Myeloid Leukemia Cell Lines Two cell lines known to express a FLT3-ITD mutation (Molm14 and MV4; 11) are treated with a novel FLT3 inhibitor which has high specificity for FLT3. The MV4; 11 cell line has low MerTK expression, while the Molm14 cell line does not express MerTK. Immunoprecipitation of FLT3-ITD positive AML cell lines after 1 h treatment with a MerTK inhibitor is analyzed for phosphorylation of FLT3 (pFLT3) in comparison to total FLT3. Phosphorylation of downstream signaling proteins STAT5, AKT, and ERK1/2 in comparison to DMSO and control TKI are also analyzed. In addition, an AML cell line that expresses MerTK and does not have activating mutations in FLT3 (U937, Kasumi-1) is also used to determine abrogation of activation of intracellular signaling pathways downstream of FLT3 and MerTK, including AKT and ERK1/2, when treated with MerTK inhibitors. Signaling in AML cell lines is analyzed after 1 hr treatment with MerTK inhibitors. Whole cell lysates or IPs are resolved on 8% Tris-Glycine SDS-PAGE gels, then transferred to a nitrocellulose membrane, which are probed for phospho-proteins. Blots are then stripped and re-probed for the total protein, or actin (loading control).

Example 13

Effect of MerTK Inhibitors on Apoptosis in Acute Myeloid Leukemia Cell Lines

AML cell lines are plated in equal number in soft agar, then colony number analyzed after incubation at 37° C. for 14 days. Colonies are counted using a Gel Count automated colony counter. AML cell lines are treated for 72 h with MerTK and apoptosis is analyzed after staining with Yo-Pro-1 iodide and propidium iodide and undergoing flow cytometric analysis.

Example 14

MerTK Inhibitors in a Molm14 Xenograft Model (FLT3-ITD AML)

A Molm14 xenograft is established by injection of $2.5 \times 10^6$ cells into NSG mice via tail vein. On day 4 after injection mice are started on daily therapy with a MerTK inhibitor or saline via oral gavage. Mice are treated through day 100 then observed for relapse.

Example 15

MerTK Inhibitors in a Patient-Derived Xenograft Model (FLT3-ITD AML)

A patient-derived xenograft model is established with cells from a patient with FLT3-ITD+ AML. NSG mice are sublethally irradiated and then $5 \times 10^6$ cells are injected via tail vein. Mice are started on therapy in the same fashion as described in Example 16 once peripheral blast counts reached ~10%.

Example 16

MerTK Inhibitors in FLT3-ITD AML Cell Lines with AC220-Resistance Mutations (D835Y and F691L)

Two cell line derivatives of the human FLT3-ITD AML cell line Molm14, which acquired either the D835Y (activation loop) or F691L (gatekeeper) mutation after selection in escalating doses of the FLT3 inhibitor AC220, are used to test the activity of MerTK inhibitors against clinically relevant FLT3 point mutations. Cells are analyzed for viability after 48 hours of culture in Molm14, Molm14:D835Y, and Molm14:F691L after treatment with a MerTK inhibitor. Phosphorylation is analyzed in Molm14, Molm14:D835Y, and Molm14:F691L after treatment with a MerTK inhibitor. Cell lines are also analyzed for resistance to treatment with AC220 at concentrations, e.g. 20-fold higher, than the inhibitory concentration in the parental line.

Example 17

MerTK Inhibitors in Molm14 Xenograft Model (FLT3-ITD AML) with AC220-Resistance Mutations (D835Y and F691L)

A Molm14:D835Y xenograft model is established by injection of $2.5 \times 10^6$ Molm14:D835Y cells into NSG mice via tail vein. The D835Y mutation in the activation loop confers resistance to the FLT3 inhibitor AC220. On day 4 after injection, mice are started on daily therapy with a MerTK inhibitor, 10 mg/kg AC220, or saline via oral gavage. Mice are treated through day 100 then observed for relapse.

The foregoing is illustrative of the present invention, and is not to be construed as limiting thereof. The invention is defined by the following claims, with equivalents of the claims to be included therein.

The invention claimed is:

1. A compound of Formula I:

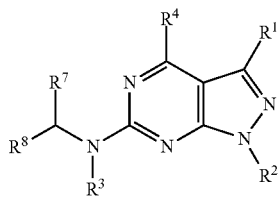

I wherein:

$R^1$ is aryl;

$R^2$ is $-R^5R^6$, where $R^5$ is a covalent bond or $C_1$ to $C_3$ alkyl and $R^6$ is cycloalkyl or heterocycloalkyl, and wherein $R^6$ is optionally substituted from one to two times with hydroxyl;

$R^3$ is H, alkyl, arylalkyl, cycloalkylalkyl, heterocycloalkylalkyl, heteroarylalkyl, or alkoxyalkyl, each of which is optionally substituted one, two or three times with independently selected polar groups;

$R^4$ is H, loweralkyl, halo, or loweralkoxy;

$R^7$ is alkyl, arylalkyl, cycloalkylalkyl, heterocycloalkylalkyl, heteroarylalkyl, or alkoxyalkyl, each of which is optionally substituted one, two or three times with independently selected polar groups;

$R^8$ is alkyl, arylalkyl, cycloalkylalkyl, heterocycloalkylalkyl, heteroarylalkyl, or alkoxyalkyl, each of which is optionally substituted one, two or three times with independently selected polar groups;

or a pharmaceutically acceptable salt thereof.

2. The compound of claim 1, having the Formula I', or I":

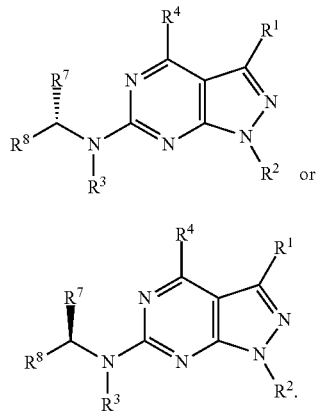

3. A compound of Formula I:

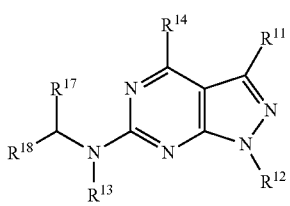

II wherein:

$R^{11}$ is $-R^9(R^{10})_n$, where $R^9$ is alkyl, alkenyl, -alkylaryl, heterocyclo, aryl, heteroaryl and $R^{10}$ is hydrogen, alkyl, haloalkyl, alkoxyalkyl, $-$O-alkylaryl, hydroxyalkyl, alkenyl, alkenyloxy, alkynyl, alkynyloxy, cycloalkyl, cycloalkylalkyl, cycloalkoxy, cycloalkylalkyloxy, heterocyclo, heterocycloalkyl, alkylheterocycloalkyl, heterocyclooxy, heterocyclolalkyloxy, aryl, arylalkyl, aryloxy, arylalkyloxy, heteroaryl, alkylheteroaryl, halo, hydroxyl, alkoxy, haloalkoxy, mercapto, alkyl-S(O)$_m$—, haloalkyl-S(O)$_m$—, alkenyl-S(O)$_m$—, alkynyl-S(O)$_m$—, cycloalkyl-S(O)$_m$—, cycloalkylalkyl-S(O)$_m$—, aryl-S(O)$_m$—, arylalkyl-S(O)$_m$—, heterocyclo-S(O)$_m$—, heterocycloalkyl-S(O)$_m$—, amino, carboxy, alkylamino, —(CH$_2$)$_m$—NHalkyl, —(CH$_2$)$_m$—N(alkyl)$_2$, —(CH$_2$)$_m$—NH(CH$_2$)$_m$OH, —(CH$_2$)$_m$—NH(CH$_2$)$_m$cycloalkyl, —(CH$_2$)$_m$—NH(CH$_2$)$_{2-3}$heterocyclo, —(CH$_2$)$_m$—NH(CH$_2$)$_m$aryl, —(CH$_2$)$_m$—NH(CH$_2$)$_{2-3}$heteroaryl, —(CH$_2$)$_m$NH(CH$_2$)$_{2-3}$N(alkyl)$_2$, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, S(O)$_2$OR$^{19}$, —CONHNH$_2$, cyano, nitro, aminosulfonyl, COOH, sulfonamide, urea, alkoxyacylamino, aminoacyloxy, —C(CH$_2$)$_2$R$^{19}$, and wherein R$^{10}$ is optionally substituted one two or three times;

m=0, 1, 2 or 3;
n=0, 1 or 2;

R$^{12}$ is —R$^{15}$R$^{16}$, where R$^{15}$ is a covalent bond or C$_1$ to C$_3$ alkyl and R$^{16}$ is cycloalkyl or heterocycloalkyl, wherein R$^{16}$ is optionally substituted one, two or three times with;

R$^{13}$ is selected from the group consisting of hydrogen, deuterium, alkyl, alkenyl, alkynyl, aryl, arylalkyl, cycloalkyl, cycloalkylalkyl, heterocyclo, heterocycloalkyl, alkylheterocycloalkyl, heteroaryl, heteroarylalkyl, and alkoxyalkyl, each of which is optionally substituted one, two or three times;

R$^{14}$ is H, loweralkyl, halo, or loweralkoxy;

R$^{17}$ is alkyl, haloalkyl, hydroxyalkyl, alkenyl, alkynyl, aryl, arylalkyl, cycloalkyl, cycloalkylalkyl, alkylheterocycloalkyl, heterocyclo, heterocycloalkyl, heteroaryl, heteroarylalkyl, and alkoxyalkyl, each of which is optionally substituted one, two or three times;

R$^{18}$ is alkyl, haloalkyl, hydroxyalkyl, alkenyl, alkynyl, aryl, arylalkyl; cycloalkyl, cycloalkylalkyl, alkylheterocycloalkyl, heterocyclo, heterocycloalkyl, heteroaryl, heteroarylalkyl, and alkoxyalkyl, each of which is optionally substituted one, two or three times;

R$^{17}$ and R$^{18}$ can form a cycloalkyl group that can be optionally substituted one, two or three times;

R$^{19}$ is hydrogen, alkyl, alkenyl, alkynyl, aryl, arylalkyl, cycloalkyl, cycloalkylalkyl, heterocyclo, heterocycloalkyl, heteroaryl, or heteroarylalkyl;

or a pharmaceutically acceptable composition or salt thereof.

4. The compound of claim 3, having a Formula selected from the group consisting of:

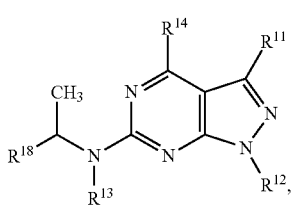

IIc

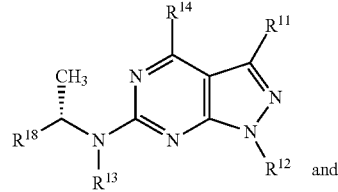

IId

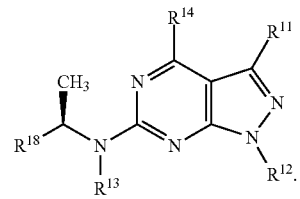

and

IIe

5. The compound of claim 1, having the structure:

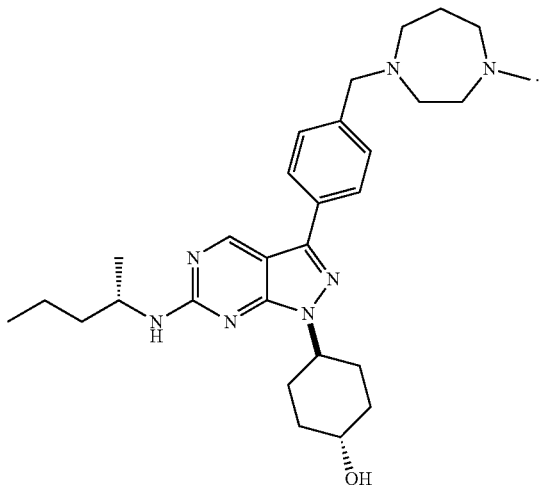

6. The compound of claim 1, wherein R$^1$ is phenyl optionally substituted 1, 2 or 3 times with heterocycloalkylalkyl which is a substituent of the formula —R'R", wherein R' is substituted or unsubstituted C$_1$-C$_2$ alkyl, and R" is an optionally substituted piperazine or morpholine group; R$^5$ is a covalent bond and R$^6$ is cycloalkyl substituted with a hydroxyl group.

7. The compound of claim 6, wherein R$^1$ is phenyl substituted 1 time with heterocycloalkylalkyl, wherein R' is unsubstituted C$_1$ alkyl, and R" is an optionally substituted piperazine group.

8. A pharmaceutically acceptable composition, comprising an effective amount of a compound of claim 5 or its pharmaceutically acceptable salt, in a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 9,603,850 B2 | Page 1 of 1 |
| APPLICATION NO. | : 14/678678 | |
| DATED | : March 28, 2017 | |
| INVENTOR(S) | : Wang et al. | |

It is certified that error appears in the above-identified patent and that said Letters Patent is hereby corrected as shown below:

In the Specification

Column 1, Lines 24-27:
The paragraph that reads:
"The U.S. Government has rights in this invention by virtue of support under Contract No. HHSN261200800001E awarded by the National Cancer Institute, National Institute of Health."

Should read:
-- This invention was made with government support under Grant Number HHSN261200800001E awarded by the National Institutes of Health. The government has certain rights in the invention. --

Signed and Sealed this
Seventeenth Day of April, 2018

Andrei Iancu
*Director of the United States Patent and Trademark Office*

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial
<220> FEATURE:
<223> OTHER INFORMATION: Mer kinase peptide substrate sequence
<220> FEATURE:
<221> NAME/KEY: MISC_FEATURE
<222> LOCATION: (1)..(1)
<223> OTHER INFORMATION: 5-FAM label
<220> FEATURE:
<221> NAME/KEY: MOD_RES
<222> LOCATION: (13)..(13)
<223> OTHER INFORMATION: AMIDATION

<400> SEQUENCE: 1

Glu Phe Pro Ile Tyr Asp Phe Leu Pro Ala Lys Lys Lys
1               5                   10

<210> SEQ ID NO 2
<211> LENGTH: 11
<212> TYPE: PRT
<213> ORGANISM: Artificial
<220> FEATURE:
<223> OTHER INFORMATION: Axl kinase peptide substrate sequence
<220> FEATURE:
<221> NAME/KEY: MISC_FEATURE
<222> LOCATION: (1)..(1)
<223> OTHER INFORMATION: 5-FAM label
<220> FEATURE:
```

```
<221> NAME/KEY: MOD_RES
<222> LOCATION: (11)..(11)
<223> OTHER INFORMATION: AMIDATION

<400> SEQUENCE: 2

Lys Lys Lys Lys Glu Glu Ile Tyr Phe Phe Phe
1               5                   10

<210> SEQ ID NO 3
<211> LENGTH: 13
<212> TYPE: PRT
<213> ORGANISM: Artificial
<220> FEATURE:
<223> OTHER INFORMATION: Tyro3 kinase peptide substrate sequence
<220> FEATURE:
<221> NAME/KEY: MISC_FEATURE
<222> LOCATION: (1)..(1)
<223> OTHER INFORMATION: 5-FAM label
<220> FEATURE:
<221> NAME/KEY: MOD_RES
<222> LOCATION: (13)..(13)
<223> OTHER INFORMATION: AMIDATION

<400> SEQUENCE: 3

Glu Phe Pro Ile Tyr Asp Phe Leu Pro Ala Lys Lys Lys
1               5                   10
```